(12) United States Patent
Hassig et al.

(10) Patent No.: US 11,596,637 B2
(45) Date of Patent: Mar. 7, 2023

(54) CHK1 (SRA737)/PARPI COMBINATION METHODS OF INHIBITING TUMOR GROWTH

(71) Applicant: SIERRA ONCOLOGY, INC., Plymouth, MI (US)

(72) Inventors: Christian Andrew Hassig, San Diego, CA (US); Bryan William Strouse, Ann Arbor, MI (US); Ryan James Hansen, San Diego, CA (US); Kenna Lynn Anderes, Poway, CA (US)

(73) Assignee: Sierra Oncology, Inc., Plymouth, MI (US)

( * ) Notice: Subject to any disclaimer, the term of this patent is extended or adjusted under 35 U.S.C. 154(b) by 14 days.

(21) Appl. No.: 16/604,116

(22) PCT Filed: Apr. 10, 2018

(86) PCT No.: PCT/US2018/026917
§ 371 (c)(1),
(2) Date: Oct. 9, 2019

(87) PCT Pub. No.: WO2018/191277
PCT Pub. Date: Oct. 18, 2018

(65) Prior Publication Data
US 2021/0077499 A1 Mar. 18, 2021

Related U.S. Application Data

(60) Provisional application No. 62/650,185, filed on Mar. 29, 2018, provisional application No. 62/635,394, filed on Feb. 26, 2018, provisional application No. 62/614,268, filed on Jan. 5, 2018, provisional application No. 62/552,364, filed on Aug. 30, 2017, provisional application No. 62/483,888, filed on Apr. 10, 2017.

(51) Int. Cl.
| | | |
|---|---|---|
| A61K 31/5377 | (2006.01) |
| A61P 35/00 | (2006.01) |
| A61K 31/166 | (2006.01) |
| A61K 31/4184 | (2006.01) |
| A61K 31/4535 | (2006.01) |
| A61K 31/454 | (2006.01) |
| A61K 31/4709 | (2006.01) |
| A61K 31/496 | (2006.01) |
| A61K 31/497 | (2006.01) |
| A61K 31/501 | (2006.01) |
| A61K 31/502 | (2006.01) |
| A61K 31/5025 | (2006.01) |
| A61K 31/519 | (2006.01) |
| A61K 31/55 | (2006.01) |
| A61K 31/551 | (2006.01) |

(52) U.S. Cl.
CPC ........ *A61K 31/5377* (2013.01); *A61K 31/166* (2013.01); *A61K 31/4184* (2013.01); *A61K 31/454* (2013.01); *A61K 31/4535* (2013.01); *A61K 31/4709* (2013.01); *A61K 31/496* (2013.01); *A61K 31/497* (2013.01); *A61K 31/501* (2013.01); *A61K 31/502* (2013.01); *A61K 31/5025* (2013.01); *A61K 31/519* (2013.01); *A61K 31/55* (2013.01); *A61K 31/551* (2013.01); *A61P 35/00* (2018.01)

(58) Field of Classification Search
CPC .................................................. A61K 31/5377
See application file for complete search history.

(56) References Cited

U.S. PATENT DOCUMENTS

| | | | |
|---|---|---|---|
| 4,107,288 A | 8/1978 | Oppenheim et al. | |
| 5,145,684 A | 9/1992 | Liversidge et al. | |
| 9,663,503 B2 | 5/2017 | Collins et al. | |
| 10,259,806 B2 | 4/2019 | Collins et al. | |
| 2005/0250836 A1* | 11/2005 | Booth .................. | C07D 487/04 548/429 |
| 2010/0249112 A1 | 9/2010 | O'Conner et al. | |
| 2011/0054001 A1 | 3/2011 | Look et al. | |
| 2015/0126471 A1 | 5/2015 | Collins et al. | |
| 2016/0208339 A1 | 7/2016 | So et al. | |
| 2016/0289686 A1 | 10/2016 | Kemp et al. | |
| 2020/0157638 A1 | 5/2020 | Hassig et al. | |

FOREIGN PATENT DOCUMENTS

| | | |
|---|---|---|
| CN | 101743003 A | 6/2010 |
| WO | 2008146035 A1 | 12/2008 |
| WO | WO 2011/058367 A2 | 5/2011 |
| WO | WO 2012/074754 A1 | 6/2012 |
| WO | WO 2013/171470 A1 | 11/2013 |

(Continued)

OTHER PUBLICATIONS

Kim et al. Clin. Cancer Res., Jun. 2017, vol. 23, No. 12, pp. 3097-3108 (Published Online Dec. 19, 2016) (Year: 2017).*
Stover et al. Clinical Cancer Research, 2016, vol. 22, No. 23, pp. 5651-5660 (Published Online Sep. 27, 2016) (Year: 2016).*
Kim et al. Int. J. Biol. Sci. 2017, vol. 13, No. 2, pp. 198-208 (Published Feb. 17, 2017) (Year: 2017).*
Booth et al. Cancer Biology & Therapy 14:5, 458-465; May 2013 (Year: 2013).*

(Continued)

*Primary Examiner* — James D. Anderson
(74) *Attorney, Agent, or Firm* — Fish & Richardson P.C.

(57) ABSTRACT

Herein disclosed are combinations of Checkpoint Kinase 1 (Chk1) inhibitors and PARP inhibitors useful for inhibiting the growth of tumors such as those in patients with cancer. In particular, the combination demonstrates remarkable synergistic effects on cancer cells that are representative models for tumors. Also provided for are methods for treating disorders or diseases mediated or affected by Chk1 and/or PARP activity.

21 Claims, 74 Drawing Sheets

(56) References Cited

FOREIGN PATENT DOCUMENTS

| WO | WO 2013171470 | | 11/2013 |
|---|---|---|---|
| WO | WO 2014/062454 | A1 | 4/2014 |
| WO | WO 2018/191299 | A1 | 10/2018 |
| WO | WO 2018/222970 | A1 | 12/2018 |
| WO | WO 2019/165458 | A1 | 8/2019 |

OTHER PUBLICATIONS

Extended European Search Report issued in European Application No. 18784295.0 dated Dec. 9, 2020 (9 pages).

International Search Report and Written Opinion of International Application No. PCT/US2018/026917, dated Jul. 2, 2018 (11 pages).

Mitchell et al., "Poly (ADP-Ribose) Polymerase 1 Modulates the Lethality of CHKI Inhibitors in Carcinoma Cells," Mol. Pharmacol, 78:909-917 (2010).

Yin et al., "CHK1 inhibition potentiates the therapeutic efficacy of PARP inhibitor BMN673 in gastric cancer," AJ J Cancer Res 7(3):473-483 (2017).

PCT International Search Report & Written Opinion, International Application No. PCT/US2018/026917, dated Jul. 2, 2018, 17 pages.

Osborne, J.D., et al., "Multiparameter Lead Optimization to Give an Oral Checkpoint Kinase 1 (CHK1) Inhibitor Clinical Candidate: (R)-5-((4-((Morpholin-2-ylmethyl)amino)-5-(trifluoromethyl)pyridin-2-yl)amino)pyrazine-2-carbonitrile (CCT245737)," J. Med. Chem., 2016, vol. 59, No. 11, pp. 5221-5237.

Brill, E. et al., "Prexasertib, a cell cycle checkpoint kinases 1 and 2 inhibitor, increases in vitro toxicity of PARP inhibition by preventing Rad51 foci formation in BRCA wild type high-grade serous ovarian cancer," Oncotarget, Oct. 31, 2017, vol. 8, No. 67, pp. 111026-111040.

Karanika, S. et al., "DNA damage response and prostate cancer: defects, regulation and therapeutic implications," Oncogene, May 28, 2015, vol. 34, pp. 2815-2822.

Kaufman, B. et al., "Olaparib Monotherapy in Patients with Advanced Cancer and a Germline BRCA1/2 Mutation," Journal of Clinical Oncology, Jan. 20, 2015, vol. 33, No. 3, pp. 244-250.

Lee, J.M. et al., "Prexasertib, a cell cycle checkpoint kinase 1 and 2 inhibitor, in BRCA wild-type recurrent high-grade serous ovarian cancer: a first-in-class proof-of-concept phase 2 study," The Lancet Oncology, Jan. 11, 2018, vol. 19, No. 2, pp. 207-215.

Mateo, J. et al., "DNA-Repair Defects and Olaparib in Metastatic Prostate Cancer," The New England Journal of Medicine, Oct. 29, 2015, vol. 373, No. 18, pp. 1697-1708.

Mendes-Pereira, A.M. et al., "Synthetic lethal targeting of PTEN mutant cells with PARP inhibitors," EMBO Molecular Medicine, Sep. 1, 2009, vol. 1, pp. 315-322.

PCT International Search Report and Written Opinion, PCT Application No. PCT/US2018/026954, dated Jun. 28, 2018, 15 pages.

PCT International Search Report and Written Opinion, PCT Application No. PCT/US2018/035566, dated Oct. 11, 2018, 17 pages.

Altschul et al., Basic Local Alignment Search Tool, J. Mol. Biol., Oct. 1990, 215:403-410.

Berglind et al., "Analysis of p53 mutation status in human cancer cell lines: a paradigm for cell line cross-contamination," Cancer Biol, Ther. May 11, 2008, 7(5):699-708.

Chiaretti et al., "Evaluation of TP53 mutations with the AmpliChip p53 research test in chronic lymphocytic leukemia: Correlation with clinical outcome and gene expression profiling," Genes, Chrom. & Cancer, Jan. 13, 2011, 50:263-274.

Faustino-Rocha et al., "Estimation of rat mammary tumor volume using caliper and ultrasonography measurements," Lab Anim (NY), Jun. 2013, 42(6):217-24.

Jensen et al., "Tumor volume in subcutaneous mouse xenografts measured by microCT is more accurate and reproducible than determined by 18F-FDG-microPET or external caliper," BMC Medical Imaging, Oct. 16, 2008, 8:16, 9 pages.

Monga et al., "Intratumoral therapy of cisplatin/epinephrine injectable gel for palliation in patients with obstructive esophageal cancer," Am. J. Clin. Oncol., Aug. 2000, 23(4):386-392.

Needleman et al., "A general method applicable to the search for similarities in the amino acid sequence of two proteins," J. Mol. Biol., Mar. 28, 1970, 48(3):443-453.

Pearson et al., "Improved tools for biological sequence comparison," Proc. Nat'l. Acad. Sci., Apr. 1988, 85:2444-8.

Richtig et al., "Calculated tumour volume as a prognostic parameter for survival in choroidal melanomas," Eye, 2004, 18: 619-623.

Tomayko et al., "Determination of subcutaneous tumor size in athymic (nude) mice," Cancer Chemotherapy and Pharmacology, 1989, 24(3):448-154.

Wang et al., "Knockdown of Chk1, Wee1 and Myt1 by RNA Interference Abrogates G2 Checkpoint and Induces Apoptosis," Cancer Biology & Therapy, Aug. 12, 2003, 3(3):305-313.

Search Report issued in Chinese Application No. 201880024426.7, dated Dec. 17, 2021 (5 pages).

* cited by examiner

CAL-27

CAL-27

DU-145

DU-145

PC-3

PC-3

HT-29

HT-29

A673

A673

MDA-MB-231

BT-474

BT-474

MDA-MB-231

SK-BR-3

SK-BR-3

OVCAR-3

OVCAR-3

OVCAR-5

OVCAR-5

| | A673 | BT-474 | CAL-27 | DU-145 | HT-29 | MDA-MB-231 | OVCAR-3 | OVCAR-5 | PC-3 | SK-BR-3 |
|---|---|---|---|---|---|---|---|---|---|---|
| BMN 673 | 0.03 | 9.37 | 0.32 | 0.91 | 2.13 | 0.04 | 0.03 | 1.38 | 0.44 | 0.21 |
| Niraparib | 0.25 | 19.99 | 1.90 | 4.10 | 3.69 | 3.18 | 0.63 | 3.57 | 2.38 | 1.23 |
| Olaparib | 2.03 | 0.05 | 2.68 | 3.07 | 0.89 | 2.20 | 3.28 | 8.01 | 3.15 | 5.36 |
| Rucaparib | 1.46 | 9.00 | 3.92 | 5.20 | 7.82 | 4.47 | 3.11 | 9.32 | 3.25 | 3.91 |
| SRA737 | 1.29 | 9.20 | 10.22 | 1.49 | 1.02 | 3.23 | 1.07 | 0.65 | 2.05 | 0.37 |

GI50 (uM)

| | A673 | BT-474 | CAL-27 | DU-145 | HT-29 | MDA-MB-231 | OVCAR-3 | OVCAR-5 | PC-3 | SK-BR-3 |
|---|---|---|---|---|---|---|---|---|---|---|
| BMN 673 | 0.03 | | 0.41 | 0.98 | | | | | 2.48 | 0.28 |
| Niraparib | 0.35 | | 3.03 | 4.55 | | | | 8.29 | 7.15 | 2.15 |
| Olaparib | 1.53 | | 4.07 | | | | | | | |
| Rucaparib | 2.63 | | | | | | 12.20 | | | 17.28 |
| SRA737 | 2.29 | | | 2.46 | 1.31 | | 7.94 | 0.45 | | 0.34 |

Note: The absence of a value indicates that 50% growth inhibition was not reached

Observed Max Response (%)

| | A673 | BT-474 | CAL-27 | DU-145 | HT-29 | MDA-MB-231 | OVCAR-3 | OVCAR-5 | PC-3 | SK-BR-3 |
|---|---|---|---|---|---|---|---|---|---|---|
| BMN 673 | 93 | 10 | 88 | 95 | 36 | 36 | 40 | 54 | 61 | 89 |
| Niraparib | 86 | 11 | 61 | 80 | 32 | 29 | 12 | 22 | 51 | 62 |
| Olaparib | 117 | 22 | 71 | 26 | 5 | 21 | 48 | 30 | 25 | 39 |
| Rucaparib | 72 | 12 | 36 | 18 | 13 | 23 | 39 | 17 | 39 | 49 |
| SRA737 | 70 | 6 | 15 | 72 | 79 | 20 | 55 | 135 | 25 | 139 |

Current Study:

Previous Study:

Figure 10

Synergy scores:

| | | Breast | | Ovary | | Prostate | | Ewing Sarcoma | Colorectal | Head and Neck |
|---|---|---|---|---|---|---|---|---|---|---|
| | | BT-474 | MDA-MB-231 | SK-BR-3 | OVCAR-3 | OVCAR-5 | DU-145 | PC-3 | A673 | HT-29 | CAL-27 |
| Compound 1 | BMN 673 | 0.0738 | 1.84 | 3.56 | 36.4 | 3.71 | 8.58 | 5.57 | 2.32 | 5.81 | 20.3 |
| | Nirapirib | 0.192 | 0.92 | 1.68 | 7.83 | 0.165 | 1.59 | 2.66 | 8.64 | 0.944 | 7.18 |
| | Olaparib | 0.0144 | 1.69 | 1.73 | 9.39 | 1.02 | 1.66 | 1.89 | 2.59 | 0.928 | 8.55 |
| | Rucaparib | 0.377 | 0.374 | 1.23 | 3.92 | 0.111 | 0.758 | 1.24 | 2.88 | 0.277 | 3.44 |

Loewe Volumes:

| | | Breast | | Ovary | | Prostate | | Ewing Sarcoma | Colorectal | Head and Neck |
|---|---|---|---|---|---|---|---|---|---|---|
| | | BT-474 | MDA-MB-231 | SK-BR-3 | OVCAR-3 | OVCAR-5 | DU-145 | PC-3 | A673 | HT-29 | CAL-27 |
| Compound 1 | BMN 673 | -5.49 | 5.44 | -1.08 | 25.1 | 2.13 | 6.32 | 6.58 | -0.239 | 7.14 | 17.5 |
| | Nirapirib | -2.2 | 1.43 | -5.22 | 7.11 | -6.87 | 0.143 | 1.96 | 3.97 | 1 | 6.81 |
| | Olaparib | -10.1 | 4.47 | -2.33 | 10.5 | -2.15 | 1.06 | 1.28 | -1.29 | -1.58 | 9.29 |
| | Rucaparib | -2.3 | 0.138 | -3.55 | 6.54 | -11 | 2.02 | 2.06 | 0.313 | -2.48 | 5.4 |

DU-145:

CAL-27:

MDA-MB-231:

BT-474:

SK-BR-3:

OVCAR-3:

OVCAR-5:

HT-29:

DU-145:

CAL-27:

MDA-MB-231:

BT-474:

SK-BR-3:

OVCAR-3

OVCAR-5:

HT-29:

DU-145:

MDA-MB-231:

BT-474:

SK-BR-3:

OVCAR-5:

HT-29:

CAL-27:

3.44

A673:

MDA-MB-231:

BT-474:

SK-BR-3:

OVCAR-3:

OVCAR-5:

0.11

Current Study:
OVCAR-3:

Previous Study: OVCAR-3

CHK1 (SRA737)/PARPI COMBINATION METHODS OF INHIBITING TUMOR GROWTH

CROSS REFERENCE TO RELATED APPLICATIONS

This application claims the benefit of U.S. Provisional Application Nos. 62/483,888 filed Apr. 10, 2017; 62/352,364 filed Aug. 30, 2017; 62/614,268 filed Jan. 5, 2018; 62/635,394 filed Feb. 26, 2018; and 62/650,185 filed Mar. 29, 2018; the contents of each of which are incorporated herein by reference in their entirety.

BACKGROUND OF THE INVENTION

Field of the Invention

The invention relates to methods, compositions and kits useful for inhibiting tumor growth. In particular, disclosed herein are combinations of Checkpoint kinase 1 (Chk1) inhibitors and poly ADP ribose polymerase (PARP) inhibitors useful for pharmaceutical compositions, kits and methods of inhibiting tumor growth, e.g., tumor growth relating to cancer.

Description of the Related Art

Cells activate a signal transduction pathway when DNA is damaged. Signals activate the cell-cycle machinery to induce DNA repair and/or cell death to mitigate propagation. Checkpoint kinase 1 (Chk1) is an important bridge in cells when sensing DNA damage. See Cancer Biology & Therapy (2004) 3:3, 305-313, incorporated herein by reference. Chk1 plays a role in regulating numerous and wide-ranging cellular functions including: immune and inflammation responses, spindle formation, DNA damage signal transduction and generally, cellular apoptosis. Chk1 inhibitors abrogate DNA damage-induced cell cycle arrest in S and/or G 2/M phases. Currently, there are no Chk1 inhibitors that are approved therapies for treatment of inhibition of tumor growth. One Chk1 inhibitor is SRA737. SRA737 is described in international patent application number PCT/GB2013/051233 and U.S. Pat. No. 9,663,503.

SUMMARY OF THE INVENTION

In an aspect, described herein is a method of inhibiting a tumor growth in a subject in need thereof, comprising administering to the subject a first effective amount of a Chk1 inhibitor and a second effective amount of a poly ADP ribose polymerase (PARP) inhibitor. In an aspect, described herein is a method of inhibiting a tumor growth in a subject in need thereof, comprising administering to the subject a first effective amount of an SRA737 and a second effective amount of a poly ADP ribose polymerase (PARP) inhibitor. In an embodiment, the SRA737 and the PARP inhibitor (PARPi) are administered separately.

In an embodiment, the SRA737 is administered at least twenty-four (24) hours after the administration of the PARPi. In an embodiment, the SRA737 and the PARPi are administered; and subsequently both SRA737 and the PARPi are administered intermittently for at least twenty-four (24) hours. In an embodiment, the SRA737 and the PARPi are administered on a non-overlapping every other day schedule. In an embodiment, the SRA737 and the PARPi are administered on a non-overlapping every 3 day alternating schedule. In an embodiment, the SRA737 and the PARPi are administered on a non-overlapping every 7 day alternating schedule. In an embodiment, the PARPi is selected from the group consisting of: Olaparib, Rucaparib, Veliparib, Niraparib, Iniparib, Talazoparib, Veliparib, Fluzoparib, BGB-290, CEP-9722, BSI-201, EZ449, PF-01367338, AZD2281, INO-1001, MK-4827, SC10914, and 3-aminobenzamine. In an embodiment, the PARPi is Olaparib. In an embodiment, the PARPi is Niraparib. In an embodiment, the PARPi is Rucaparib. In an embodiment, the PARPi is Talazoparib.

In certain embodiments of the methods described herein, the subject has a condition or disorder selected from the group consisting of: bladder cancer, breast cancer, cervical cancer, colorectal cancer, gastric cancer, endometrial cancer, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, head and neck cancer, metastatic castration-resistant prostate cancer (mCRPC), HRR-proficient mCRPC, and high grade serous ovarian cancer (HGSOC). In an embodiment, the subject has a cancer that is resistant to chemotherapeutic therapy. In an embodiment, the subject has a cancer that is resistant to platinum therapy. In an embodiment, the subject has a cancer that is resistant to PARPi therapy.

In certain embodiments of the methods described herein, the subject has a cancer that has a mutation in at least one gene involved in the DNA Damage Response (DDR). In certain embodiments, the subject has a cancer that has a mutation in at least one gene selected from the group consisting of: BRIP1, HDAC2, ATM, BLM, BRCA1, BRCA2, CHEK2, FANCA, FANCC, FANCD2, FANCE, FANCF, FANCG, FANCI, FANCL, FANCM, MLH1, MSH2, MSH6, PALB2, POLD1, POLE, PMS2, POLE, RAD50, RAD51, RAD51B, RAD51C, RAD51D, RAD52, RAD54L, RPA1, SETD2 SMARCA4, TP53BP1, XRCC2, XRCC3, KMT2D and ARID1A. In certain embodiment, the subject has a cancer with a mutation or altered expression in REV7, SCHLFN-11, or combinations thereof. In an embodiment, the subject has a cancer that does not have a mutation or altered expression in BRCA, other homologous recombination genes, or combinations thereof. In an embodiment, the subject has a cancer that is proficient in the homologous recombination pathway. In an embodiment, the subject has a cancer with a mutation or altered expression in BRCA, other homologous recombination genes, or combinations thereof. In an embodiment, the subject has a cancer with a reversion mutation in BRCA1 or BRCA2. In an embodiment, the subject has a cancer with a deficiency in the homologous recombination pathway.

In certain embodiments of the methods described herein, the route of administration is selected from the group consisting of intravenous, subcutaneous, cutaneous, oral, intramuscular, and intraperitoneal. In an embodiment, the first effective amount is 0.001 mg/kg to 15 mg/kg and the second effective amount is 0.001 mg/kg to 15 mg/kg. In an embodiment, the first effective amount is 0.1 mg/kg to 1.5 mg/kg and the second effective amount is 0.1 mg/kg to 1.5 mg/kg. In an embodiment, the first effective amount is 10 mg to 1000 mg. In an embodiment, tumor growth is reduced in the subject. In an embodiment, tumor growth is reduced by at least 1% after administration. In an embodiment, administration results in tumor growth of no more than 5% of the original tumor volume as measured after administration. In an embodiment, the subject is human.

In certain aspects, described herein are methods of reducing cellular proliferation of a cell, comprising contacting the cell with a first effective amount of SRA737 and a second effective amount of a PARPi. In certain aspects, described herein are methods of inhibiting a Chk1 activity in a cell, the method comprising contacting the cell with a first effective amount of SRA737 and a second effective amount of a PARPi. In certain aspects, described herein are methods of inhibiting a PARP activity in a cell, the method comprising contacting the cell with a first effective amount of SRA737 and a second effective amount of a PARPi. In certain embodiments, the cell is a tumor cell. In certain embodiments, the method is performed in vitro. In an embodiment, the SRA737 and the PARPi are administered simultaneously. In an embodiment, the SRA737 and the PARPi are administered sequentially. In an embodiment, the SRA737 and the PARPi are administered; and subsequently both SRA737 and the PARPi are administered intermittently for at least twenty-four (24) hours. In an embodiment, the SRA737 and the PARPi are administered on a non-overlapping every other day schedule. In an embodiment, the SRA737 and the PARPi are administered on a non-overlapping every 3 day alternating schedule. In an embodiment, the SRA737 and the PARPi are administered on a non-overlapping every 7 day alternating schedule.

In an aspect, described herein is a combination comprising SRA737 and a PARPi. In an embodiment, the PARPi is selected from the group consisting of: Olaparib, Rucaparib, Veliparib, Niraparib, Iniparib, Talazoparib, Veliparib, Fluzoparib, BGB-290, CEP-9722, BSI-201, EZ449, PF-01367338, AZD2281, INO-1001, MK-4827, SC10914, and 3-aminobenzamine. In certain aspects, described herein is a pharmaceutical composition comprising the combination and at least one pharmaceutically acceptable carrier or excipient. In certain aspects, described herein is an SRA737 for use in inhibiting a tumor growth in a subject in need thereof by co-administration with a PARPi. In certain aspects, described herein is a PARPi for use in inhibiting a tumor growth in a subject in need thereof by co-administration with SRA737. In certain aspects, described herein is a product comprising SRA737 and a PARPi for simultaneous, separate or sequential use in the inhibition of a tumor growth in a subject in need thereof. In certain aspects, described herein are kits comprising the combination comprising SRA737 and a PARPi, or the pharmaceutical composition and instructions for use. In certain aspects, described herein are kits comprising a pharmaceutical composition comprising SRA737 and a pharmaceutical composition comprising a PARPi.

In certain aspects, described herein are methods of inhibiting a tumor growth in a subject in need thereof, comprising administering to the subject a first effective amount of a Chk1 inhibitor and a second effective amount of a poly ADP ribose polymerase (PARP) inhibitor. In certain embodiments, the PARPi is selected from the group consisting of: Olaparib, Rucaparib, Veliparib, Niraparib, Iniparib, Talazoparib, Veliparib, Fluzoparib, BGB-290, CEP-9722, BSI-201, EZ449, PF-01367338, AZD2281, INO-1001, MK-4827, SC10914, and 3-aminobenzamine. In certain embodiments, the subject has a condition or disorder selected from the group consisting of: bladder cancer, breast cancer, cervical cancer, colorectal cancer, gastric cancer, endometrial cancer, hepatocellular cancer, leukemia, lymphoma, myeloma, non-small cell lung cancer, ovarian cancer, prostate cancer, pancreatic cancer, brain cancer, sarcoma, small cell lung cancer, neuroblastoma, head and neck cancer, metastatic castration-resistant prostate cancer (mCRPC), HRR-proficient mCRPC, and high grade serous ovarian cancer (HGSOC). In certain embodiments, the subject has a cancer that has a mutation in at least one gene selected from the group consisting of: BRIP1, HDAC2, ATM, BLM, BRCA1, BRCA2, CHEK2, FANCA, FANCC, FANCD2, FANCE, FANCF, FANCG, FANCI, FANCL, FANCM, MLH1, MSH2, MSH6, PALB2, POLD1, POLE, PMS2, POLE, RAD50, RAD51, RAD51B, RAD51C, RAD51D, RAD52, RAD54L, RPA1, SETD2 SMARCA4, TP53BP1, XRCC2, XRCC3, KMT2D and ARID1A. In certain aspects, disclosed herein is a Chk1 inhibitor for use in inhibiting a tumor growth in a subject in need thereof by co-administration with a PARPi. In certain aspects, disclosed herein is a PARPi for use in inhibiting a tumor growth in a subject in need thereof by co-administration with a Chk1 inhibitor. In certain aspects, disclosed herein is a product comprising a Chk1 inhibitor and a PARPi for simultaneous, separate or sequential use in the inhibition of a tumor growth in a subject in need thereof. In certain aspects, disclosed herein are methods for use of a Chk1 inhibitor in the manufacture of a medicament for treatment tumor growth in a subject in need thereof by co-administration of a PARPi. In certain aspects, disclosed herein are methods for use of a PARPi in the manufacture of a medicament for treatment tumor growth in a subject in need thereof by co-administration of a Chk1 inhibitor. In certain embodiments, the Chk1 inhibitor is selected from the group consisting of Prexasertib (LY2606368), PF-477736, AZD7762, Rabusertib (LY2603618), MK-8776 (SCH 900776), CHIR-124, SAR-020106 and CCT245737. In an embodiment, the Chk1 inhibitor is Prexasertib (LY2606368). In an embodiment, the Chk1 inhibitor is PF-477736. In an embodiment, the Chk1 inhibitor is AZD7762. In an embodiment, the Chk1 inhibitor is Rabusertib (LY2603618). In an embodiment, the Chk1 inhibitor is MK-8776 (SCH 900776). In an embodiment, the Chk1 inhibitor is CHIR-124. In an embodiment, the Chk1 inhibitor is SAR-020106. In an embodiment, the Chk1 inhibitor is CCT245737.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5 shows a summary of single agent activity ($EC_{50}$), ($GI_{50}$) and Observed Maximum Response of SRA737 in the ten cell lines tested.

FIG. 10 shows synergy scores and Lowe volume values obtained for ten cell lines treated with "Compound 1" (SRA737) and either BMN 673, Niraparib, Olaparib and Rucaparib.

DETAILED DESCRIPTION OF THE INVENTION

Figure 1:
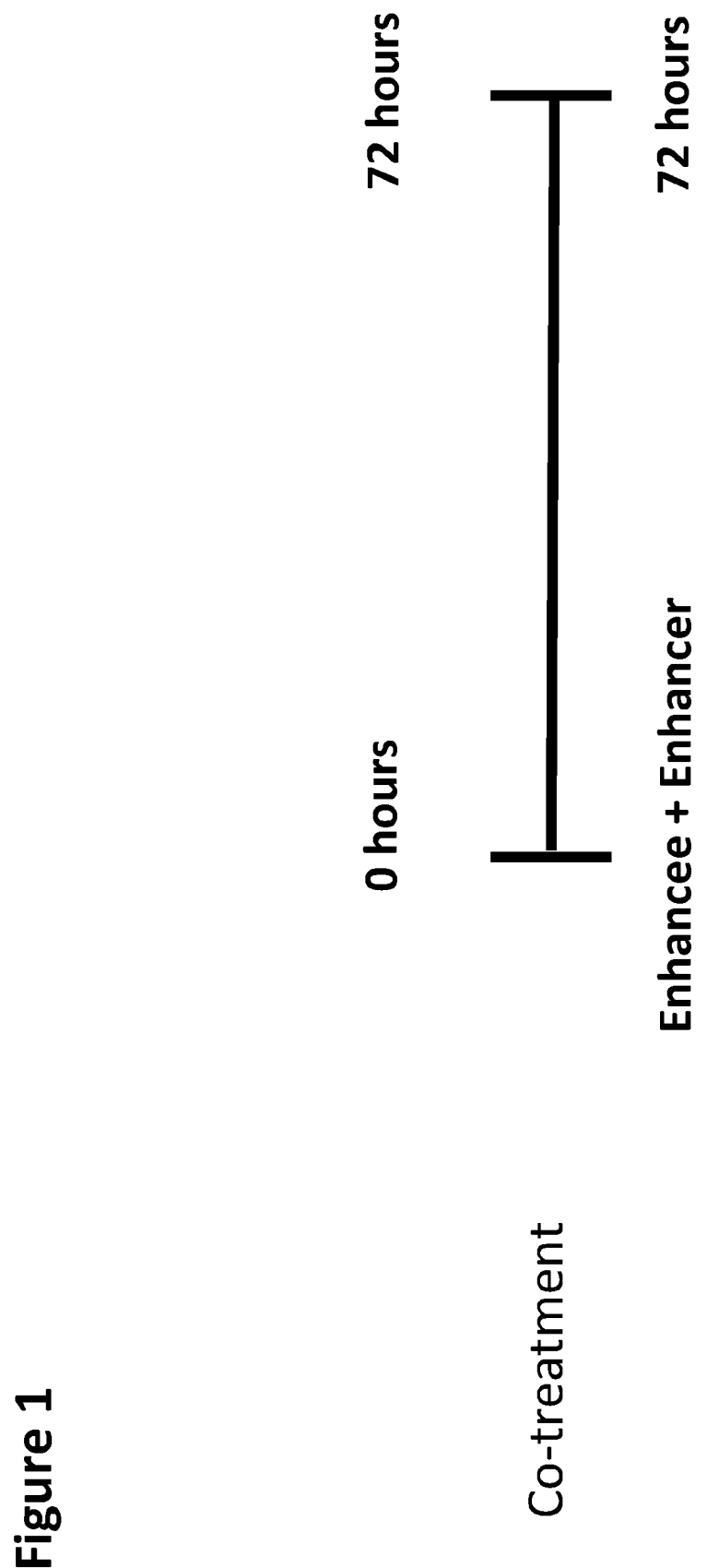
FIG. 1 is a diagram of the dosage schedule used for experiments performed to identify PARPi compounds that synergize with the Chk1 inhibitor, SRA737 (Sierra Compound 1 or ProNAi Compound 1).

Disclosed herein are methods of inhibiting tumor growth in a subject, e.g., a human, by administration of a combination of a Chk1 inhibitor (e.g., SRA737) and a PARP inhibitor to the subject. Also disclosed herein are combinations of a Chk1 inhibitor and a PARP inhibitor in, e.g., pharmaceutical compositions and/or kits, useful for practicing the methods of inhibiting tumor growth. Also disclosed herein are methods of reducing expression of a marker gene in a cell, of inhibiting a Chk1 activity in a cell, and of inhibiting PARP in a cell by administration of a combination of a Chk1 inhibitor and a PARP inhibitor to the cell, either in vivo or in vitro.

Described herein is the surprising result that pharmacological inhibition of PARP activity potentiates the efficacy of a Chk1 inhibitor when administered in accordance with the methods of the invention. The combination of a Chk1 inhibitor and a PARP inhibitor displays unexpected and synergistic effects useful for inhibiting tumor growth and for treating disorders such as cancer.

As described in detail below, in vitro cell viability screening assays were performed by detection of ATP metabolism using an ATP monitoring luminescence detection assay, and the screens demonstrated the synergistic anti-tumor activity of the combination of a Chk1 inhibitor, SRA737, and a PARP inhibitor. SRA737 activity was significantly enhanced by a PARP inhibitor in PC-3, DU-145, HT-29, CAL-27, A673, MDA-MB-231, SK-BR-3, OVCAR-3 and OVCAR-5 cancer cell lines. Finally, PARP inhibitors, in combination with SRA737 demonstrated significantly increased anti-cancer efficacy across a broad range of cell line panels representative of tumor types that include, but certainly are not limited to: bladder, colorectal, lung, ovary, pancreas and head and neck cancer cell lines.

Apropos, a Chk1 inhibitor and a PARP inhibitor combination is significantly more potent and effective for inhibiting tumor growth, for inhibiting cancer cell replication, e.g. inhibiting the growth of tumor cells, inhibiting Chk1 and PARP activity than either a Chk1 inhibitor or a PARP inhibitor alone.

Definitions

Terms used in the claims and specification are defined as set forth below unless otherwise specified.

The practice of the present invention includes the use of conventional techniques of organic chemistry, molecular biology (including recombinant techniques), microbiology, cell biology, biochemistry and immunology, which are within the skill of the art.

In this application, reference will be made to a number of technical designations. All numerical designations, e.g., pH, temperature, time, concentration, and weight, including ranges of each thereof, are approximations that typically may be varied (+) or (−) by increments of 0.1, 1.0, or 10.0, as appropriate. Reagents described herein are exemplary and equivalents of such may be known in the art.

Compounds utilized in the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example, and without limitation, tritium ($^3H$), iodine-125 ($^{125}I$), or carbon-14 ($^{14}C$). All isotopic variations of the compounds of the present invention, whether radioactive or not, are intended to be encompassed within the scope of the present invention.

The term "subject" refers to any mammal including humans, and so includes mammals such as those animals of veterinary and research interest that are including, but not limited to: simians, cattle, horses, dogs, cats, and rodents with a tumor or cancer.

The term "administering" or "administration" of a drug and/or therapy to a subject (and grammatical equivalents of this phrase) refers to both direct or indirect administration, which may be administration to a subject by a medical professional, may be self-administration, and/or indirect administration, which may be the act of prescribing or inducing one to prescribe a drug and/or therapy to a subject.

The term "treating" or "treatment of" a disorder or disease refers to taking steps to alleviate the symptoms of the disorder or disease, or otherwise obtain some beneficial or desired results for a subject, including clinical results. Any beneficial or desired clinical results may include, but are not limited to, alleviation or amelioration of one or more symptoms of cancer or conditional survival and reduction of tumor load or tumor volume; diminishment of the extent of the disease; delay or slowing of the tumor progression or disease progression; amelioration, palliation, or stabilization of the tumor and/or the disease state; or other beneficial results.

The term "in situ" or "in vitro" refers to processes that occur in a living cell growing separate from a living organism, e.g., growing in tissue culture.

The term "in vivo" refers to processes that occur in a living organism.

The term "Chk1" or "CHEK1" or "Checkpoint kinase 1" refers to serine/threonine-protein kinase that is encoded by the CHEK gene. CHEK can also be referred to as Cell Cycle Checkpoint Kinase, CHK1 Checkpoint Homolog, EC 2.7.11.1 and EC 2.7.11. Chk1 refers to all alternatively spliced analogues and comprises Homo sapiens Chk1 isoforms encoded by amino acid sequences and nucleotide sequences according to National Center for Biotechnology Information (NCBI) accession numbers: NP_001107594.1, NP_001107593.1, NP 001265.2, NP_001231775.1, NP_001317356.1, NP 001317357.1, XP_016872635.1, XP_024304105.1, and XP_011540862.1, NM 001114122, NM_001114121.2, NM 001274.5, NM 001244846.1, NM_001330427.1, NM_001330428.1, and XM_017017146.2.

The term "PARP" refers to poly ADP-ribose polymerase. The term "PARP" refers to all members of the PARP family, including: PARP1, PARP2, VPARP (ParP4), Tankyrase-1 and -2 (PARP-5a or TNKS, and PARPa5b or TNKS2), PARP3, PARP6, TIPARP (or PARP7), PARP8, PARP9, PARP10, PARP11, PARP12, PARP14, PARP15, PARP16, and any alternatively spliced analogues.

The term "PARP inhibitor" or "PARPi" refers to an inhibitor of PARP. A PARPi may be a small molecule, an antibody or a nucleic acid. A PARPi may reduce the expression of PARP, inhibit the activity or function of PARP in cells, or combinations thereof. PARPi include inhibitors that do or do not alter the binding of PARP to DNA. PARPi may inhibit any members of the PARP family. PARPi include, but are not limited to: Olaparib (AZD2281) (commercially available from Chemietek, catalog number CT-A2281, LC Laboratories®, catalog number O-9201 and Selleckchem catalog number, S1060), Rucaparib (PF-01367338) (commercially available from Chemietek, catalog number CT-AG01, LC Laboratories® catalog number, R-6399 and Selleckchem, catalog number S1098), Veliparib (ABT-888) (commercially available from Chemietek, catalog number CT-A888, LC Laboratories®, catalog number V-4703 and Selleckchem, catalog number S1004), Niraparib (MK-4827) (commercially available from Chemietek, catalog number CT-MK4827, Selleckchem, catalog number S7625), Iniparib (BSI-201) (commercially available from Chemietek, catalog number CT-BS1201, Selleckchem, catalog number S1087), Talazoparib (BMN673) (commercially available from Selleckchem, catalog number S7048), 3-aminobenzamine (INO-1001) (commercially available from Selleckchem, catalog number S1132), Fluzoparib, BGB-290 (commercially available from MedKoo Biosciences, Inc. catalog number 206852), CEP-9722 (commercially available from MedKoo Biosciences, Inc. catalog number 204910), and SC-10914.

The term "Chk1 inhibitor" refers to and inhibitor of Chk1 or CHEK1. A Chk1 inhibitor may be a small molecule, an antibody or a nucleic acid. A Chk1 inhibitor may reduce the expression of CHEK1, inhibit the activity or function of Chk1 in cells, or combinations thereof. Chk1 inhibitors include, but are not limited to: SRA737, Prexasertib (LY2606368) (Commercially available from Sellechchem, Catalog No. S7178), PF-477736 (Commercially available from Sellechchem, Catalog No. S2904), AZD7762 (Commercially available from Sellechchem, Catalog No. S1532), Rabusertib (LY2603618) (Commercially available from Sellechchem, Catalog No. S2626), MK-8776 (SCH 900776) (Commercially available from Sellechchem, Catalog No. S2735), CHIR-124 (Commercially available from Sellechchem, Catalog No. S2683), SAR-020106 (Commercially available from Sellechchem, Catalog No. S7740) and CCT245737 (Commercially available from Sellechchem, Catalog No. S8253).

The term "effective amount" means an amount sufficient to produce a desired effect, e.g., an amount sufficient to inhibit tumor growth.

The term "coadministration" refers to two or more compounds administered in a manner to exert their pharmacological effect during the same period of time. Such coadministration can be achieved by either simultaneous, contemporaneous, or sequential administration of the two or more compounds.

The term "QnD or qnd" refers to drug administration once every "n" days. For example, QD (or qd) refers to once every day or once daily dosing, Q2D (or q2d) refers to a dosing once every two days, Q7D refers to a dosing once every 7 days or once a week, Q5D refers to dosing once every 5 days, and so on.

The term "reduction" of a symptom or symptoms (and grammatical equivalents of this phrase) refers to decreasing the severity or frequency of the symptom(s), or elimination of the symptom(s).

The term "tumor suppressor gene" refers to any gene that increases a "hallmark of tumor growth or cancer" when inhibited, deleted, reduced in expression, or otherwise has reduced function in a cell. "Hallmarks of tumor growth or cancer" include, but are not limited to, sustained or increased proliferation of a cell, sustained or increased proliferative signaling in a cell, replicative immortality, resisting cell death (e.g., apoptosis), evasion of growth suppression, avoidance of immune destruction, induction of angiogenesis, activation of invasive or metastatic potential, promotion of inflammation, deregulated cellular energetics, genome instability, and combinations thereof. Tumor suppressor genes include, but are not limited to, the following genes: CDKN1A, CDKN1B, CDKN2A, CDKN2B, CDKN2C, RB1, TP53, and any alternatively spliced analogues. CDKN1A can also be referred to as: Cyclin Dependent Kinase Inhibitor 1A, CDK-interacting Protein 1, CDKN1, CAP20, MDA-6, CIP1, SDI, WAFi and P21. CDKN1B can also be referred to as: Cyclin Dependent Kinase 1B, P27KIP1, KIP1, Cyclin Dependent Kinase Inhibitor P27, CDKN4, MEN1B, and MEN4. CDKN2A can also be referred to as: Cyclin Dependent Kinase Inhibitor 2A, Cyclin-Dependent Kinase 4 Inhibitor A, Multiple Tumor Suppressor 1, P16-INK4A, P14ARF, CDKN2, CDK4I, MTS-1, MTS1 and MLM. CDKN2B can also be referred to as: Cyclin Dependent Kinase Inhibitor 2B, Cyclin-Dependent Kinase 4 Inhibitor B, Multiple Tumor Suppressor 2, P14-INK4b, P15-INK4b, MTS-2, MTS2, P14 CDK Inhibitor, P15 CDK Inhibitor, CDK4B inhibitor, INK4B, TP15 and P15. CDKN2C can also be referred to as: Cyclin Dependent Kinase Inhibitor 2C, P18-INK4C, P18-INK6, Cyclin-Dependent Kinase 6 Inhibitor P18, Cyclin-Dependent Kinase 4 Inhibitor C, CDK6 inhibitor P18, CDKN6, INK4C and P18. RB1 can also be referred to as: RB, Retinoblastoma 1, Retinoblastoma-Associated Protein, RB Transcriptional Corepressor, Protein Phosphatase 1Regulatory Subunit 130, P105-Rb, Pp110, and PRb. TP53 can also be referred to as: P53, Tumor Protein 53, Phosphoprotein P53, P53 Tumor Suppressor, Tumor Suppressor P53, TRP53, Antigen NY-CO-13, BCC7, and LFS1. CDKN1A comprises *Homo sapiens* CDKN1A encoded by amino acid sequences and nucleotide sequences according to NCBI accession numbers: NP_001207707 and NM_001220778.1. CDKN1B comprises *Homo sapiens* CDKN1B encoded by amino acid sequences and nucleotide sequences according to NCBI accession numbers: NP_004055 and NM_004064. CDKN2A comprises *Homo sapiens* CDKN2A encoded by amino acid sequences and nucleotide sequences according to National Center for Biotechnology Information (NCBI) accession numbers: NP_478102 and NM_058195.3. CDKN2B comprises *Homo sapiens* CDKN2B encoded by amino acid sequences and nucleotide sequences according to NCBI accession numbers: NP_004927 and NM_004936.3. CDKN2C comprises *Homo sapiens* CDKN2C encoded by amino acid sequences and nucleotide sequences according to NCBI accession numbers: NP_001253 and NM_001262.2. RB1 comprises *Homo sapiens* RB1 encoded by amino acid sequences and nucleotide sequences according to NCBI accession numbers: NP_000312 and NM_000321.2. TP53 comprises *Homo sapiens* TP53 encoded by amino acid sequences and nucleotide sequences according to NCBI accession numbers: NP_000537 and NM_000546.5.

The term "DNA damage repair (DDR) gene" or "DNA damage repair pathway gene" refers to any gene that directly or indirectly promotes repair of DNA mutations, breaks or other DNA damage or structural changes. DNA damage repair genes include, but are not limited to, the following genes: ATM, BLM, BRCA1, BRCA2, CHEK2, MLH1, MSH2, PALB2, POLD1, RAD50, RAD51, RAD51B, RAD51C, RAD51D, MSH6, PMS2, RAD52, RAD54L, RPA1, SETD2, SMARCA4, TP53BP1, XRCC2, XRCC3, POLE, KMT2D, ARID1A and any alternatively spliced analogues. DDR genes also include genes in the Fanconi anemia (FA) pathway. Genes in the FA pathway include, but are not limited to, Fanconi anemia complementation group (FANC) genes, such as FANCA, FANCC, FANCD2, FANCE, FANCF, FANCG, FANCI, FANCL, FANCM and any alternatively spliced analogues. ATM can also be referred to as: ATM Serine/Threonine Kinase, Ataxia Telangiectasia Mutated, A-T mutated, TELO1, TEL1, ATDC, AT1, ATE, ATA, ATC and ATD. BLM can also be referred to as: Bloom Syndrome RecQ Like Helicase, DNA Helicase RecQ-like Type 2, RecQ Protein-like 3, RECQL3, RECQL2, RECQ2, and Bloom Syndrome Protein. BRCA1 is also referred to as: BRCA/BRCA1-Contining Complex Subunit 1, Protein Phosphatase 1 Regulatory Subunit 53, Fanconi Anemia Complementation Group S, RING Finger Protein 53, BROVCA1, PPP1R53, BRCA1 and BRCC1. BRCA2 can also be referred to as: BRCA/BRCA1-Contining Complex Subunit 2, Fanconi Anemia Group D1 Protein, Fanconi Anemia complementation Group D1, Breast Cancer 2 Tumor Suppressor, Breast and Ovarian Cancer Susceptibility Protein 2, FANCD1, FACD, FANCD, FAD1, GLM3 and FAD. CHEK2 is also referred to as: Checkpoint Kinase 2, CHK2 Checkpoint Homolog, CHK2, CDS1, Cds1 Homolog, HCds1, RAD53, PP1425 and LFS2. MLH1 can also be referred to as: MutL Homolog 1, DNA Mismatch Repair Protein Mlh1, COCA2, HNPCC, HNPCC, HMLH1 and FCC2. MSH2 can also be referred to as: MutS Homolog 2, HMSH2, DNA Mismatch Repair Protein Msh2, MutS Protein Homolog 2, HNPCC1, HNPCC, LCFS2, COCA1 and FCC1. PALB2 can also be referred to as: Partner and Localizer of BRACA2, FANCN, Fanconi Anemia Complementation Group N and PNCA3. POLD1 can also be referred to as DNA Polymerase Delta 1 Catalytic Subunit, DNA Polymerase Subunit Delta P125, PPOLD, CDC2 Homolog, CRCS10, CDC2 and MDPL. RAD50 can also be referred to as: RAD50 Double Strand Break Repair Protein, HRad50, DNA Repair Protein RAD50, RAD502 and NBSLD. RAD51 can also be referred to as: RAD51 Recombinase, RAD51 Homolog A, HRAD51, RAD51A, RECA, Rec-A like protein, Recombination Protein A, HsT16930, BRCC5, FANCR and MRMV2. RAD51B can also be referred to as: RAD51 Paralog B, RAD51 Homolog B, RAD51 Homolog 2, RAD51L1, REC2, DNA Repair Protein RAD51 Homolog B, RAD51-Like 1 and RAD51-Like Protein 1. RAD51C can be referred to as: RAD51 Paralog C, RAD51-Like Protein 2, RAD51 Homolog 3, RAD51L2, R51H2, DNA Repair Protein RAD51 Homolog 3, BROVCA3 and FANCO. RAD51D can also be referred to as: RAD51 Paralog D, RAD51 Homolog 4, RAD51-Like Protein 3, RAD51L3, R51H3, DNA Repair Protein RAD51 Homolog 4, TRAD and BROVCA4. MSH6 can also be referred to as: MutS Homolog 6, G/T Mismatch-Binding Protein, MutS Protein Homolog 6, DNA Mismatch Repair Protein Msh6, GTMBP, GTBP, P160, HNPCC5, HMSH6 and HSAP. PMS2 can also be referred to as: PMS1 Homolog 2 Mismatch Repair Protein, DNA Mismatch Repair Protein PMS2, PMS1 Protein Homolog 2, PMSL2, PMS2 Postmeiotic Segregation Increased 2, HNPCC4, PMS2CL and MLH4. RAD52 can also be referred to as: RAD52 Homolog DNA Repair Protein. RAD54L can also be referred to as: RAD54 Homolog, RAD54 Like, RAD54A, HRAD54, HHR54, HR54 and DNA Repair and Recombination Protein RAD54-Like. RPA1 can also be referred to as: Replication Protein A1, Single-Stranded DNA-Binding Protein, Replication Factor A Protein 1, RF-A Protein 1, REPA1, RPA70, MSTP075, MST075, HSSB, RF-A and RP-A. SETD2 can also be referred to as: SET Domain Containing 2, Protein-Lysine N-Methyltransferase SETD2, Huntingtin-Interacting Protein B, Lysine N-Methyltransferase 3A, P231HBP, HIP-1, HIF-1, KMT3A, HYPB, SET2, Histone-Lysine N-Methyltransferase SETD2, Huntington Interacting Protein 1, SET Domain-Containing Protein 2, KIAA1732, HSPC069, HBP231, HSET2, HIF1 and LLS. SMARCA4 can also be referred to as: SWI/SNF Related Matrix Associated Actin Dependent Regulator of Chromatin Subfamily A Member 4, Mitotic Growth and Transcription Activator, ATP-Dependent Helicase SMARCA4, BRG-1 Associated Factor 190A, Protein Brahma Homolog 1, BRM/SWI2-Related Gene, Homeotic Gene Regulator, Brahma Protein-Like 1, Nuclear Protein GRB1, Protein BRG-1, SNF2-Like 4, SNF2-Beta, BAF 190A, BRG1, SNF2LB, BAF190, HSNF2b, MRD16, RTPS2, SNF2B, SWI2, SNF2 and CSS4. TP53BP1 can also be referred to as: Tumor Protein P53 Binding Protein 1, P53-Binding Protein 1, P53BP1, 53BP1, Tumor Suppressor P53-Binding Protein 1, Tumor Protein P53-Binding Protein 1, Tumor Protein 53-Binding Protein, TP53-Binding Protein 1, TDRD30 and P202. XRCC2 can also be referred to as: X-RAY Repair Cross Complementing 2, X-Ray Repair Complementing Protein 2, DNA Repair Protein XRCC2, and FANCU. XRCC3 can also be referred to as: X-RAY Repair Cross Complementing 3, X-Ray Repair Complementing Protein 3, DNA Repair Protein XRCC3 and CMM6. POLE can also be referred to as: DNA Polymerase Epsilon Catalytic Subunit, DNA Polymerase Epsilon Catalytic Subunit A, DNA Polymerase II Subunit A, POLE1, CRCS12 and FILS. KMT2D can also be referred to as: MLL2, Lysine Methyltransferase 2D, Myeloid/Lymphoid or Mixed-Lineage Leukemia 2, Lysine-Specific Methyltransferase 2D, Lysine-N-Methyltransferase 2D, ALL-Related Protein, Histone-Lysine N-Methyltransferase 2D, Kabuki Mental Retardation Syndrome, MLL4, ALR, CAGL114, KABUKI, TNRC21, AAD10 and KMS. ARID1A can also be referred to as: AT-Rich Interaction Domain 1A, SWI/SNF-Related Matrix-Associated Actin Dependent Regulator of Chromatin Subfamily F Member 1, AT Rich Interactive Domain 1A, ARID Domain-Containing Protein 1A, SWI/SNF Complex Protein P270, BRG-1 Associated Factor 250a, BRG-1 Associated Factor 250, SWI-Like Protein, OsaHomolog 1, BAF250a, SMARCF1, BAF250, HOSA1, B120, OSA1, Chromatin Remodeling Factor P250, BM029, MRD14, CSS2, P270 and ELD. ATM comprises *Homo sapiens* ATM encoded by amino acid sequences and nucleotide sequences according to NCBI accession numbers: NP_000042 and NM_000051.3. BLM comprises *Homo sapiens* BLM encoded by amino acid sequences and nucleotide sequences according to NCBI accession numbers: NP_000048 and NM_000057.3. BRCA1 comprises *Homo sapiens* BRCA1 encoded by amino acid sequences and nucleotide sequences according to NCBI accession numbers: NP_009225 and NM_007294.3. BRCA2 comprises *Homo sapiens* BRCA2 encoded by amino acid sequences and nucleotide sequences according to NCBI accession numbers: NP_000050 and NM_000059.3. CHEK2 comprises *Homo sapiens* CHEK2 encoded by amino acid sequences and nucleotide sequences according to NCBI accession numbers: NP_009125 and NM_007194.3. MLH1 comprises *Homo sapiens* MLH1 encoded by amino acid sequences and nucleotide sequences according to NCBI accession numbers: NP_000240 and NM_000249.3. MSH2 comprises *Homo sapiens* MSH2 encoded by amino acid sequences and nucleotide sequences according to NCBI accession numbers: NP_000242 and NM_000251.2. PALB2 comprises *Homo sapiens* PALB2 encoded by amino acid sequences and nucleotide sequences according to NCBI accession numbers: NP_078951 and NM_024675.3. POLD1 comprises *Homo sapiens* POLD1 encoded by acid sequences and nucleotide sequences according to NCBI accession numbers: NP_002682 and NM_002691.3. RAD50 comprises *Homo sapiens* RAD50 encoded by amino acid sequences and nucleotide sequences according to NCBI accession numbers: NP_005723 and NM_005732.3. RAD51 comprises *Homo sapiens* RAD51 encoded by amino acid sequences and nucleotide sequences according to NCBI accession numbers: NP_002866 and NM_002875.4. RAD51B comprises *Homo sapiens* RAD51B encoded by amino acid sequences and nucleotide sequences according to NCBI accession numbers: NP_002868.1 and NM_002877.5. RAD51C comprises *Homo sapiens* RAD51C encoded by amino acid sequences and nucleotide sequences according to NCBI accession numbers: NP_478123 and NM_058216.2. RAD51D comprises *Homo sapiens* RAD51D encoded by amino acid sequences and nucleotide sequences according to NCBI accession numbers: NP_002869 and NM_002878.3. MSH6 comprises *Homo sapiens* MSH6 encoded by amino acid sequences and nucleotide sequences according to NCBI accession numbers: NP_000170 and NM_000179.2. PMS2 comprises *Homo sapiens* PMS2 encoded by amino acid sequences nucleotide sequences according to NCBI accession numbers: NP_000526 and NM_000535.6. RAD52 comprises *Homo sapiens* RAD52 encoded by amino acid sequences and nucleotide sequences according to NCBI accession numbers: NP_602296 and NM_134424.3. RAD54L comprises *Homo sapiens* RAD54L encoded by amino acid sequences and nucleotide sequences according to NCBI accession numbers: NP_003570 and NM_003579.3. RPA1 comprises *Homo sapiens* RPA1 encoded by amino acid sequences and nucleotide sequences according to NCBI accession numbers: NP_002936 and NM_002945.4. SETD2 comprises *Homo sapiens* SETD2 encoded by amino acid sequences and nucleotide sequences according to NCBI accession numbers: NP_054878 and NM_014159.6. SMARCA4 comprises *Homo sapiens* SMARCA4 encoded by amino acid sequences and nucleotide sequences according to NCBI accession numbers: NP_003063, NM_003072.3, NP_001122321 and NM_001128849.1. TP53BP1 comprises *Homo sapiens* TP53BP1 encoded by amino acid sequences and nucleotide sequences according to NCBI accession numbers: NP_001135452 and NM_001141980.2. XRCC2 comprises *Homo sapiens* XRCC2 encoded by amino acid sequences and nucleotide sequences according to NCBI accession numbers: NP_005422 and NM_005431.1. XRCC3 comprises *Homo sapiens* XRCC3 encoded by amino acid sequences and nucleotide sequences according to NCBI accession numbers: NP_005423 and NM_005432.3. POLE comprises *Homo sapiens* POLE encoded by amino acid sequences and nucleotide sequences according to NCBI accession numbers: NP_006222 and NM_006231.3. KMT2D comprises *Homo sapiens* KMT2D encoded by amino acid sequences and nucleotide sequences according to NCBI accession numbers: NP_003473 and NM_003482.3. ARID1A comprises *Homo sapiens* ARID1A encoded by amino acid sequences and nucleotide sequences according to NCBI accession numbers: NP_006006 and NM_006015.5.

FANCA can also be referred to as: Fanconi Anemia Complementation Group A, FANCH, FACA, FAA, Fanconi Anemia Type 1, FA-H, FA1, FAH and FA. FANCC can also be referred to as: Fanconi Anemia Complementation Group C, FACC, FAC, Fanconi Anemia Group C Protein, and FA3. FANCD2 is also referred to as Fanconi Anemia Complementation Group D2, Fanconi Anemia Group D2 Protein, FANCD, FA-D2, FAD2, FA4. FANCE can also be referred to as: Fanconi Anemia Complementation Group E, Fanconi Anemia Group E Protein, FACE and FAE. FANCF can also referred be to as: Fanconi Anemia Complementation Group F, Fanconi Anemia Group F Protein, FACF and FAF. FANCG can also be referred to as: Fanconi Anemia Complementation Group G, Fanconi Anemia Group G Protein, DNA Repair Protein XRCC9, XRCC9 Truncated Fanconi Anemia Group G Protein, FACG and FAG. FANCI can also be referred to as: Fanconi Anemia Complementation Group I, Fanconi Anemia Group I Protein, KIAA1794 and FACI. FANCL can also be referred to as: Fanconi Anemia Complementation Group L, Fanconi Anemia Group L Protein, RING-Type E3 Ubiquitin Transferase FANCL, PHD Finger Protein 9, FAAP43, PHF9, E3 Ubiquitin-Protein Ligase FANCL and POG. FANCM can also be referred to as: Fanconi Anemia Complementation Group M, Fanconi Anemia Group M Protein, ATP-Dependent RNA Helicase FANCM, KIAA1596, Protein Hef Ortholog, FAAP250 and Protein FACM. FANCA comprises *Homo sapiens* FANCA encoded by acid sequences and nucleotide sequences according to NCBI accession numbers: NP_000126 and NM_000135.3. FANCC comprises *Homo sapiens* FANCC encoded by amino acid sequences and nucleotide sequences according to NCBI accession numbers: NP_000127 and NM_000136.2. FANCD2 comprises *Homo sapiens* FANCD2 encoded by amino acid sequences and nucleotide sequences according to NCBI accession numbers: NP_149075, NM_033084.4, NP_001306913 and NM_001319984.1. FANCE comprises *Homo sapiens* FANCE encoded by amino acid sequences and nucleotide sequences according to NCBI accession numbers: NP_068741 and NM_021922.2. FANCF comprises *Homo sapiens* FANCF encoded by amino acid sequences and nucleotide sequences according to NCBI accession numbers: NP_073562 and NM_022725.3. FANCG comprises *Homo sapiens* FANCG encoded by amino acid sequences and nucleotide sequences according to NCBI accession numbers: NP_004620 and NM_004629.1. FANCI comprises *Homo sapiens* FANCI encoded by amino acid sequences and nucleotide sequences according to NCBI accession numbers: NP_001106849 and NM_001113378.1. FANCL comprises *Homo sapiens* FANCL encoded by amino acid sequences and nucleotide sequences according to NCBI accession numbers: NP_001108108, NM_001114636.1, NP_060532 and NM_018062.3. FANCM comprises *Homo sapiens* FANCM encoded by amino acid sequences and nucleotide sequences according to NCBI accession numbers: NP_065988 and NM_020937.3.

The term "replication stress gene" refers to any gene that is induced or activated upon exposure of a cell increased DNA replication, increased initiation of replication (i.e., entry into S phase of cell cycle) increased mitosis, increased cell proliferation, increased DNA damage, excessive compacting of chromatin, over-expression of oncogenes or combinations thereof, and mediate the response to the stress, such as a stalled replication fork. Replication stress genes include, but are not limited to, the following genes: ATR, CHEK1 and any alternatively spliced analogues. ATR can also be referred to as: ATR Serine/Threonine Kinase, Ataxia Telangiectasia and RAD3-Related Protein, FRP1, MEC1 Mitosis Entry Checkpoint 1, FRAP Related Protein 1, FCTCS, SCKL1, MEC1 and SCKL. ATR comprises *Homo sapiens* ATR encoded by amino acid sequences and nucleotide sequences according to NCBI accession numbers: NP_001175 and NM_001184.3.

The term "oncogenic driver gene" or "oncogene" refers to any gene that when activated, over-expressed or otherwise increased in activity or abundance, leads to increased one or more hallmarks of tumor growth or cancer in a cell. Oncogenic driver genes include, but are not limited to, the following genes: CCNE1, KRAS, MYC, MYCN, MDM2, and any alternatively spliced analogues. In addition, negative regulators of oncogenic drivers, such as FBXW7, can also be viewed as oncogenic if mutation results in loss-of-function or reduced function. CCNE1 can also be referred to as: Cyclin E1, CCNE, G1/S-Specific Cyclin E1, Cyclin Es, Cyclin Et and PCCNEL. KRAS can also be referred to as KRAS Proto-Oncogene GTPase, V-Ki-Ras2 Kirsten Rat Sarcoma Viral Oncogene Homolog, V-Ki-Ras2 Kirsten Rat Sarcoma Viral Oncogene Homolog, Kirsten Rat Sarcoma Viral Proto-Oncogene, Cellular C-Ki-Ras2 Proto-Oncogene, Transforming Protein P21, C-Kirsten-Ras Protein, KRAS2A, K-RAS2B, K-RAS4A, K-RAs4B, K-Ras, KRAS1, C-Ki-Ras, K-Ras 2, C—K—RAS, CFC2, RALD, NS3 and NS. Myc can also be referred to as: C-Myc, MYC Proto-Oncogene BHLH Transcription Factor, V-Myc Avian Myelocytomatosis Viral Oncogene Homolog, Class E Basic Helix-Loop-Helix Protein 39, Proto-Oncogene C-Myc, BHLHe39, Avian Myelocytomatosis Viral Oncogene Homolog, Myc Proto-Oncogene Protein, MRTL and MYCC. MYCN can also be referred to as: N-MYC, MYCN Proto-Oncogene BHLH Transcription Factor, V-Myc Avian Myelocytomatosis Viral Oncogene Neuroblastoma Derived Homolog, Class E Basic Helix-Loop-Helix Protein 37, BHLHe37, NMYC, Neuroblastoma-Derived V-Myc Avian Myelocytomatosis Viral Related Oncogene, N-Myc Proto-Oncogene Protein, Neuroblastoma Myc Oncogene, Oncogene NMYC and ODED. MDM2 can also be referred to as: MDM2 Proto-Oncogene, MDM2 Proto-Oncogene E3 Ubiquitin Protein Ligase, Oncoprotein Mdm2, Hdm2, Mdm2 Transformed 3T3 Cell Double Minute 2 P53 Binding Protein, Double Minute 2 Human Homolog of P53-Binding Protein, RING-Type E3 Ubiquitin Transferase Mdm2, P53-Binding Protein Mdm2, Double Minute 2 Protein, ACTFS and HDMX. FBXW7 can also be referred to as: F-Box and WD Repeat Domain Containing 7, F-Box and WD Repeat Domain Containing 7, E3 Ubiquitin Protein Ligase, F-BOX Protein FBX30, Fbx30, SEL-10, SEL10, HCdc4, FBW7, HAgo, Archipelago Homolog, F-Box Protein SEL-10, Archipelago, FBXO30, FBXW6, CDC4, FBW6 and AGO. CCNE1 comprises *Homo sapiens* CCNE1 encoded by amino acid sequences and nucleotide sequences according to NCBI accession numbers: NP_001229 and NM_001238.3. KRAS comprises *Homo sapiens* KRAS encoded by amino acid sequences and nucleotide sequences according to NCBI accession numbers: NP_203524 and NM_033360.3. MYC comprises *Homo sapiens* MYC encoded by amino acid sequences and nucleotide sequences according to NCBI accession numbers: NP_002458, NM_002467.5 and ABW69847. MYCN comprises *Homo sapiens* MYCN encoded by amino acid sequences and nucleotide sequences according to NCBI accession numbers: NP_005369 and NM_005378.5. MDM2 comprises *Homo sapiens* MDM2 encoded by amino acid sequences and nucleotide sequences according to NCBI accession numbers: NP_002383, NM_002392.5 and Q00987.

The term "homologous recombination gene" refers to a gene that either directly or indirectly promotes, activates or is important for homologous recombination in cells. Homologous recombination genes include, but are not limited to, genes involved in double strand break repair (e.g., BRCA1 and BRCA2).

It must be noted that, as used in the specification and the appended claims, the singular forms "a," "an" and "the" include plural referents unless the context clearly dictates otherwise.

Recitation of ranges herein includes the recited endpoints and all points there between.

Methods of the Invention

Disclosed herein are methods of inhibiting tumor growth in a subject, e.g., a human, by administration of both a Chk1 inhibitor (e.g., SRA737) and a PARP inhibitor. A detailed description of the two compounds, kits comprising the compounds, and methods of use thereof are found below.

Tumor Inhibition

The present disclosure is directed to methods using combinations of the compound a Chk1 inhibitor (e.g., SRA737) and a PARP inhibitor to inhibit the progression of, reduce the size of, reduce the aggregation of, reduce the volume of, and/or otherwise inhibit the growth of a tumor. Also provided herein are methods of treating the underlying disease, e.g., cancer, and extending the survival of the subject.

In one embodiment provided for is a method of inhibiting the growth of a tumor in a subject in need thereof, the method comprising administering to the subject a first effective amount of a Chk1 inhibitor and a second effective amount of a PARP inhibitor. In some aspects, the disclosure provides for a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by tumor volume. In some aspects, the disclosure provides for a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the absolute size of the tumor. In some aspects, the disclosure provides for a method of inhibiting the growth of a tumor, wherein tumor growth is reduced by 1%, 2%, 3%, 4%, 5%, 6%, 7%, 8%, 9%, 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, or 100% as measured by the expression levels of tumor markers for that type of tumor.

Additional Methods

The present disclosure provides for a method of inhibiting Chk1 activity in a cell, the method comprising contacting the cell with a first effective amount of a Chk1 inhibitor (e.g., SRA737) and a second effective amount of a PARP inhibitor. The present disclosure also provides for a method of inhibiting a CDC25 activity in a cell, the method comprising contacting the cell with a first effective amount of a Chk1 inhibitor and a second effective amount of a PARP inhibitor. The present disclosure also provides for a method of inhibiting a CDK1/2 activity in a cell, the method comprising contacting the cell with a first effective amount of a Chk1 inhibitor and a second effective amount of a PARP inhibitor. In some aspects, the disclosure provides for a method of inhibiting Chk1 or PARP activity in a cell, wherein the first effective amount and second effective amount is an amount that produces an $IC_{50}$ value of no more than 0.001 µM, no more than 0.01 µM, no more than 0.1 µM, no more than 1 µM, no more than 2 µM, no more than 3 µM, no more than 5 µM, no more than 6 µM, no more than 8 µM, no more than 10 µM, no more than 12 µM, no more than 14 µM, no more than 16 µM, no more than 18 µM, no more than 20 µM, no more than 25 µM, no more than 30 µM, no more than 35 µM, no more than 40 µM, no more than 50 µM, no more than 75 µM or no more than 100 µM.

In Vitro Methods

In an aspect, the present disclosure provides for methods for inhibiting the growth of a tumor by slowing or stopping cancerous tumor cells from replicating and/or surviving. Herein disclosed the combination of a Chk1 inhibitor (e.g., SRA737) and a PARP inhibitor are shown to arrest the cellular proliferation of cancer cell lines indicative of bladder, colorectal, lung, ovary, pancreas and head and neck cancers. Accordingly, provided for are methods for inhibiting the growth of a tumor, the method comprising contacting cancerous tumor cells with a combination of Chk1 inhibitor and a PARP inhibitor, where the cancerous tumor cells include: bladder cancer, breast cancer, colorectal cancer, cervical cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck cancerous cells.

Provided for are methods for reducing cellular proliferation of a cell, the method comprising contacting cancerous tumor cells with a combination of a Chk1 inhibitor (e.g., SRA737) and a PARP inhibitor, where the cancerous tumor cells include: bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck cancerous cells.

Provided for are methods for inducing a marker of DNA damage and/or replication stress and/or inducing apoptosis, the method comprising contacting cancerous tumor cells with a combination of a Chk1 inhibitor (e.g., SRA737) and a PARP inhibitor, where the cancerous tumor cells include: bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck cancerous cells.

Further, the present disclosure also provides methods of inhibiting Chk1 activity, inhibiting PARP activity, and/or reducing expression of a marker gene in a cell, the method comprising contacting the cell with a first effective amount of Chk1 inhibitor (e.g., SRA737) and a second effective amount of a PARP inhibitor. In each of these aspects, i.e. for any and all such methods described herein foe methods of inhibiting tumor growth, inhibiting Chk1 activity, inhibiting PARP activity, and/or activating cell cycle progression in a cell, the cell can be in a subject, but also the cell can be outside a biological context. And so methods are provided for in vitro where the cell is growing separate from a living organism, e.g. growing in tissue culture. In the course of using said methods to inhibit the growth of tumor cells, it may be that some cells of the tumor or even cells in the microenvironment, or in the vicinity of the tumor, are not yet cancerous cells, but are pre-cancerous cells. Accordingly, the present disclosure provides for methods where the cell is cancerous and methods where the cell is not cancerous. With regard to methods in vitro where the cell is a cancer cell, the present disclosure provides for methods wherein the cancer is bladder cancer, breast cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck.

In an aspect, the present disclosure provides for methods wherein the cell is a PC-3 cancer cell. In some aspects, the present disclosure provides for methods wherein the cell is a DU-145 cancer cell. In some aspects, the present disclosure provides for methods wherein the cell is a HT-29 cancer cell. In some aspects, the present disclosure provides for methods wherein the cell is a Cal-27 cancer cell. In some aspects, the present disclosure provides for methods wherein the cell is an A673 cancer cell. In some aspects, the present disclosure provides for methods wherein the cell is an OV-90 cancer cell. In some aspects, the present disclosure provides for methods wherein the cell is a MDA-MB-231 cancer cell. In some aspects, the present disclosure provides for methods wherein the cell is an OVCAR-3 cancer cell. In some aspects, the present disclosure provides for methods wherein the cell is an OVCAR-5 cancer cell. In some aspects, the present disclosure provides for methods wherein the cell is a SK-BR-3 cancer cell.

In an aspect, the present disclosure provides for methods wherein the cell is from a subject after administration of a combination as described herein. In an aspect, the present disclosure provides for methods wherein the cell is from a subject that has not been administered any anti-cancer treatment for at least one day, one week, one month, two months, three months, six months, or one year. In an aspect, the present disclosure provides for methods wherein the cell is from a human subject that has not been administered any anti-cancer treatment for at least one day, one week, one month, two months, three months, six months, or one year.

In some aspects, the present disclosure provides for methods that are performed in vivo. In some aspects, the present disclosure provides for methods that are performed in vivo with a human subject.

Types of Tumors

In some aspects, the present disclosure provides for methods of inhibiting the growth of a tumor wherein the tumor is from a cancer that is bladder cancer, breast cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, small cell lung cancer, brain cancer, sarcoma, neuroblastoma, or squamous cell carcinoma of the head and neck.

In some embodiments, the tumor is from a cancer that is metastatic castration-resistant prostate cancer (mCRPC), HRR-proficient mCRPC, or high grade serous ovarian cancer (HGSOC).

Accordingly, the present disclosure also provides for methods of treating a cancer in a subject in need thereof, the method comprising administering a first effective amount of Chk1 inhibitor (e.g., SRA737) and a second effective amount of a PARP inhibitor to the subject. In some aspects, methods are disclosed for the treatment of cancer wherein the cancer is bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck.

In some embodiments, the cancer is metastatic castration-resistant prostate cancer (mCRPC), HRR-proficient mCRPC, or high grade serous ovarian cancer (HGSOC).

In further aspects, methods of reducing expression of a marker gene in a cell, methods of inhibiting Chk1 and/or methods of inhibiting PARP are provided for wherein the of Chk1, the inhibition of PARP, and/or the expression of a marker gene is in a cancer cell that is bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck.

In some embodiments, cancer cell is from a cancer that is metastatic castration-resistant prostate cancer (mCRPC), HRR-proficient mCRPC, or high grade serous ovarian cancer (HGSOC).

Cellular Assays

In some aspects, the present disclosure includes using assays to measure the anti-tumor and anti-cancer activity of the compounds alone, and then in combination. In some aspects, the assays comprise contacting cancer cell lines grown in culture with the compounds of the invention and then assaying the cells for cell number, cell proliferation, cell survival and cell apoptosis. In some aspects, the cells are assayed for expression of markers of DNA damage or apoptosis. In certain embodiments, the assay comprises measuring ATP levels of treated cells. In certain embodiments the assay is an MTT assay. In certain embodiments, cell lines are contacted with combinations of compounds to identify powerful combinations that demonstrate selective, synergistic killing of tumor cells.

In some aspects, the present disclosure provides methods wherein the clinical endpoint is identified by Synergy Score, Growth Inhibition Score or Loewe Volume Score scoring.

In one aspect, the endpoint is identified by Synergy Score as measured by the assays and formulas described herein.

In one aspect, the present disclosure provides for methods wherein the combination has a Loewe Volume score of no more than −40, −30, −20, −10, −5, or −1.

In one aspect, the present disclosure provides for methods wherein the combination has a Synergy Score of at least 2.8, 3.1, 3.5, 3.8, 4.2, 4.5, 5, 7, 10, 12, or 15.

Clinical Endpoints

Provided herein are methods for inhibiting the growth of a tumor in a subject and/or cell, wherein the conditions of said methods are such that the method results in a clinically relevant endpoint.

Tumor growth occurs when one or more biological cells grow and divide much more rapidly resulting in an increase in the number of cells in comparison to the normal and healthy process of cells division. This phenomenon is an indication that the cells are in a disease state such as cancer or pre-cancer. Moreover, tumor growth oftentimes comes about in discrete stages prior to the agglomerated cells forming a tumor.

There are several methods the skilled artisan can use to measure cell replication rates. The overall metabolic activity inside a cell can be measured via a labeled biological product. For example, there are several commercially available dyes (e.g., MTT) that can penetrate the cell and interact with certain enzymes and other factors to produce a detectable product. Also, cellular biomarkers can be measured in a cell. For example a BrdU assay can incorporate a thymidine derivative into cellular DNA and be detected with an antibody. Proliferating cell nuclear antigen (PCNA) is another such biomarker for detection. Besides tagging techniques, the skilled artisan can also use for example, microscopy or flow cytometry to allow for cell counts.

In an aspect, cellular replication is measured by a clinical endpoint that includes: a quality of life (QOL) score, duration of response (DOR, clinical benefit rate (CBR), patient reported outcomes (PRO), an objective response rate (ORR) score, a disease-free survival (DFS) or progression-free survival (PFS), a time to progression (TTP), an Overall Survival, a time-to-treatment failure (TTF), RECIST criteria, and/or a Complete Response. The clinical endpoints can be determined using methods well known to one of skill in the art.

In some aspects, the present disclosure provides methods wherein the growth of the tumor is reduced no more than 5, 10, 20, 40, 50, 60, 80, 90, 95, 97, 99, or 99.9% after administration of the first effective amount of a Chk1 inhibitor, but before the administration of the second effective amount of a PARP inhibitor. In some aspects, the present disclosure provides methods wherein the growth of the tumor is reduced no more than 5, 10, 20, 40, 50, 60, 80, 90, 95, 97, 99, or 99.9% after administration of the second effective amount of a PARP inhibitor but before the administration of the first effective amount of SRA737.

In some aspects, the present disclosure provides methods wherein the % reduction is calculated based on measurement(s) of one or more clinical endpoints.

In some aspects, the present disclosure provides methods wherein the growth of the tumor is reduced as measured by an increase or a decrease in total cell count in a MTT assay, or by change in genetic profile as measured by a ctDNA assay, by no more than or at least 5, 10, 20, 40, 50, 60, 80, 90, 95, 97, 99, or 99.9% after administration of the first effective amount of SRA737, but before the administration of the second effective amount of a PARP inhibitor. In some aspects, the present disclosure provides methods wherein the growth of the tumor is reduced as measured by an increase or a decrease in total cell count in a MTT assay, or by change in genetic profile as measured by a ctDNA assay, by no more than or at least 5, 10, 20, 40, 50, 60, 80, 90, 95, 97, 99, or 99.9% after administration of the second effective amount of a PARP inhibitor but before the administration of the first effective amount of SRA737.

In some general aspects, the present disclosure provides methods wherein the growth of the tumor is reduced at least 5, 10, 20, 40, 50, 60, 80, 90, 95, 97, 99, or 99.9% after administration of the combination. In some aspects, the present disclosure provides methods wherein the growth of the tumor is reduced as measured by an increase or a decrease in total cell count in a MTT assay, or by change in genetic profile as measured by a ctDNA assay, by at least 5, 10, 20, 40, 50, 60, 80, 90, 95, 97, 99, or 99.9% after administration of the combination.

In some aspects, the present disclosure provides methods wherein administration results in an $IC_{50}$ value below 10 μM and/or a $GI_{50}$ value below 1 μM. In some aspects, the present disclosure provides methods wherein administration results in an $IC_{50}$ value below 10 μM and/or a $GI_{50}$ value below 1 μM at twenty-four (24) hours after administration. In some aspects, the present disclosure provides methods wherein administration results in an $IC_{50}$ value below 10 μM and/or a $GI_{50}$ value below 1 μM at forty-eight (48) hours after administration.

In some aspects, the present disclosure provides methods wherein the administration results in an AUC of at least 1, 10, 25, 50, 100, 200, 400, 600, 800, or 1000.

In some aspects, the present disclosure provides methods wherein the administration results in an $IC_{50}$ value of no more than 0.001, 0.005, 0.01, 0.05, 0.1, 1, 3, 5, 10, 20, 40, 50, 60, 80, 90, 100, 200, 250, 300, 350, or 400 μM.

In some aspects, the present disclosure provides methods wherein the administration results in an $EC_{50}$ value of at least 0.01, 0.1, 1, 3, 5, 10, 20, 40, 50, 60, 80, 90, 100, 200, 250, 300, 350, or 400 μM.

In some aspects, the present disclosure provides methods wherein the administration results in an therapeutic index (TI) value ranging from about 1.001:1 to about 50:1, about 1.1:1 to about 15:1, about 1.2:1 to about 12:1, about 1.2:1 to about 10:1, about 1.2:1 to about 5:1, or about 1.2:1 to about 3:1.

In some aspects, the present disclosure provides methods wherein the administration results in an $GI_{50}$ value of at least 0.1 μM, 0.3 μM, 0.5 μM, 0.7 μM, 1 μM, 1.5 μM, 2 μM, 2.5 μM, 3 μM, 4 μM, 5 μM, or 10 μM.

In some aspects, the present disclosure provides methods wherein the administration results in a Maximum Response Observed (Max Response) value of no more than 0.1, 0.5, 1, 2 μM, 2.5 μM, 3 μM, 4 μM, 5 μM, or 10 μM.

Tumor growth can be expressed in terms of total tumor volume. There exist formulas, both generally speaking and specific to certain tumor models, that the skilled artisan can use to calculate tumor volume based upon the assumption that solid tumors are more or less spherical. In this regard, the skilled artisan can use experimental tools such as: ultrasound imaging, manual or digital calipers, ultrasonography, computed tomographic (CT), microCT, $^{18}$F-FDG-microPET, or magnetic resonance imaging (MRI) to measure tumor volume. See for example Monga S P, Wadleigh R, Sharma A, et al. Intratumoral therapy of cisplatin/epinephrine injectable gel for palliation in patients with obstructive esophageal cancer. Am. J. Clin. Oncol. 2000; 23(4):386-392; Mary M. Tomayko C., Patrick Reynolds, 1989. Determination of subcutaneous tumor size in athymic (nude) mice. Cancer Chemotherapy and Pharmacology, Volume 24, Issue 3, pp 148-154; E Richtig, G Langmann, K Müllner, G Richtig and J Smolle, 2004. Calculated tumour volume as a prognostic parameter for survival in choroidal melanomas. Eye (2004) 18, 619-623; Jensen et al. BMC Medical Imaging 2008. 8:16; Tomayko et al. Cancer Chemotherapy and Pharmacology September 1989, Volume 24, Issue 3, pp 148-154; and Faustino-Rocha et al. Lab Anim (NY). 2013 June; 42(6):217-24, each of which are hereby incorporated by reference in their entirety.

In some aspects, the present disclosure provides methods wherein administration results in a reduction in tumor volume of at least 5, 10, 20, 40, 50, 60, 80, 90, 95, 97, 99 or 99.9% after administration of the combination. In some aspects, the present disclosure provides methods wherein administration results in a reduction in tumor size, as measured by medical imaging techniques, of at least 5, 10, 20, 40, 50, 60, 80, 90, 95, 97, 99 or 99.9% after administration of the combination.

In some aspects, the present disclosure provides methods wherein administration results in method where administration results in a reduction in tumor volume of at least 5% after one (1), two (2), three (3), four (4), six (6), eight (8), twelve (12), sixteen (16), twenty (20), twenty four (24), thirty six (36), or fifty two (52) weeks.

Indications and Genetic Markers

Subjects with highest probability for effective tumor inhibition or cancer treatment include those which have cancer cells that carry mutations. Often tumor cells or otherwise cancer cells that are TP53-deficient display this kind of sensitivity. To increase the odds of successful treatment, scientists may determine the degree to which a tumor cell gene is mutated, the case of the former being the degree to which TP53 is mutated, or the degree to which the gene (TP53 former), or its penultimate gene product, is over-expressed (amplified) or under-expressed in the cancer cells, or inactivated via an amplification in MDM2. These scientific measurements are determined via methods well known to a skilled artisan, such as immunohistochemistry and reverse transcriptase polymerase chain reaction (RTPCR). For example, suitable methods for assessing p53 status are described in Chiaretti et al., 2011, Genes, Chrom. & Cancer 50: 263-274; and Berglind et al., 2008, Cancer Biol. & Ther. 7: 5, 699-708, each of which is incorporated herein by reference. Moreover, commercially available test kits, like the AmpliChip Test, are available to the skilled artisan for such purposes and do not take an overabundance of time or training to utilize.

The inventors observed that certain cancer cell lines, with pre-specified genetic mutations are 'more prone' to the strong combination activities of Chk1 inhibitors (e.g., SRA737) & PARP inhibitors, demonstrating comparatively high Synergy Scores across the compound library.

In some aspects, the present disclosure provides for methods wherein the genetic marker is identified using a cancer cell that has a mutated gene for that marker. In some aspects, the genetic marker is identified by comparison with the genetic profile of non-cancerous cells, i.e. healthy cells. Apropos in some aspects, the present disclosure provides for methods wherein the genetic marker is identified using both cancer cells and non-cancer cells to determine one or more mutated genes, optionally where both the cancer cells and non-cancer cells are from a single human subject.

In some aspects, the present disclosure provides for methods of inhibiting the growth of a tumor where tumor cells have an identified genetic mutation when compared to the genetic sequence of matched control eukaryotic cells.

In some aspects, the present disclosure provides for methods wherein the tumor is a tumor from a cancer with a genetic mutation in a gene that is a tumor suppressor gene, a DNA damage repair gene, a replication stress gene, or an oncogenic driver gene and the cancer is bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck.

In some aspects, the methods described herein are used to treat a subject that has a mutation in at least one gene selected from the group consisting of BRIP1, HDAC2, ATM, BLM, BRCA1, BRCA2, CHEK2, FANCA, FANCC, FANCD2, FANCE, FANCF, FANCG, FANCI, FANCL, FANCM, MLH1, MSH2, MSH6, PALB2, POLD1, POLE, PMS2, POLE, RAD50, RAD51, RAD51B, RAD51C, RAD51D, RAD52, RAD54L, RPA1, SETD2 SMARCA4, TP53BP1, XRCC2, XRCC3, KMT2D and ARID1A.

In some aspects, the present disclosure provides for methods wherein the cancer is TP53 deficient cancer.

In certain aspects, the cancer has a mutation or altered expression in REV7, SCHLFN-11, or combinations thereof.

In certain aspects, the cancer with a mutation or altered expression in BRCA, other homologous recombination genes, or combinations thereof.

In certain aspects, the cancer has a deficiency in the homologous recombination pathway.

In certain aspects, the cancer does not have a mutation or altered expression in BRCA, other homologous recombination genes, or combinations thereof.

In certain aspects, the cancer is proficient in the homologous recombination pathway.

In certain aspects, the cancer has a reversion mutation in BRCA1 or BRCA2 resulting in partial recovery of homologous recombination pathway and PARPi resistance.

In certain aspects, the cancer is resistant to PARPi therapy.

In certain aspects, the present disclosure provides for methods wherein the subject is suffering from a tumor and/or cancer that has cells that overexpress the biomarker ORC1, CLSPN, or USP1. In some aspects, the present disclosure provides for methods wherein the subject is suffering from a tumor and/or cancer that has cells that under-express the marker gene RAD50.

In some aspects, the present disclosure provides for using high throughput genetic sequencing to select subjects suffering from cancer that have cells that provide a Synergy Score above 2.5. In some aspects, the present disclosure provides for using high throughput genetic sequencing to select subjects suffering from cancer that have cells that provide a Loewe Volume Score above 8.0.

In some aspects, the present disclosure provides for 2D genetic screening of tumor cell lines and/or isogenic cell lines.

In some aspects, the present disclosure provides for methods wherein the genetic marker is identified by next generation sequencing.

In some aspects, the present disclosure provides for methods wherein the subject is screened to determine if their tumor and/or cancer provides a Synergy Score above 3.0 prior to administration of the combination of SRA737 and a PARP inhibitor. In some aspects, the present disclosure provides for methods wherein the subject is screened both before and after administration of the combination of SRA737 and a PARP inhibitor to determine one or more clinically relevant endpoints and to determine Synergy Score and/or Loewe Volume Score.

Subjects

The term "subject" is interchangeable with the term "patient." The present disclosure provides for administering the combination of SRA737 and a PARP inhibitor to a subject or a patient that is in need thereof. In some aspects, the tumor from a subject is screened with genetic testing and/sequencing prior to administration. In some aspects, the tumor from a subject is screened with genetic testing and/sequencing after administration. In some aspects, the tumor from a subject is screened both after and before administration. In some aspects, healthy cells from the subject are screened with genetic testing and/sequencing prior to administration, after administration, or both. In some aspects, the tumor from a subject is screened with other biological tests or assays to determine the level of expression of certain biomarkers. In some aspects, the tumor from a subject is screened with both genetic testing and/sequencing and other biomarker tests or assays.

In some aspects, the present disclosure provides for methods wherein the subject is a mammal. In some aspects, the present disclosure provides for methods wherein the subject is a primate.

In some aspects, the present disclosure provides for methods wherein the subject is a mouse.

In some aspects, the present disclosure provides for methods wherein the subject is a human.

In some aspects, the present disclosure provides for methods wherein the subject is a human that has a tumor having a genetic mutation in one or more of the following genes: a tumor suppressor gene, a DNA damage repair gene, a replication stress gene, or an oncogenic driver gene. In some aspects, the present disclosure provides for methods wherein the subject is a human that has a tumor that is TP53 deficient. In some aspects, the present disclosure provides for methods wherein the subject is a human that has a tumor that has a mutation in the CCNE1 gene. In some aspects, the present disclosure provides for methods wherein the subject is a human that has a tumor that has a mutation in the MYC gene. In some aspects, the present disclosure provides for methods wherein the subject is a human that has a tumor that has a mutation in the MYCN gene. In some aspects, the present disclosure provides for methods wherein the subject is a human that has a tumor that has a mutation in the CHEK1 gene. In some aspects, the present disclosure provides for methods wherein the subject is a human that has a tumor that has a mutation in the CHEK2 gene. In some aspects, the present disclosure provides for methods wherein the subject is a human that has a tumor that has a mutation in the KRAS gene.

In some aspects, the present disclosure provides for methods wherein the tumor is in a human suffering from cancer that is selected from the group consisting of: bladder cancer, breast cancer, cervical cancer, colorectal cancer, esophageal cancer, gastric cancer, head and neck cancer, hepatocellular cancer, leukemia, lung cancer, lymphoma, mesothelioma, melanoma, myeloma, ovarian cancer, endometrial cancer, prostate cancer, pancreatic cancer, renal cell cancer, non-small cell lung cancer, small cell lung cancer, brain cancer, sarcoma, neuroblastoma, or squamous cell carcinoma of the head and neck.

In some aspects, the present disclosure provides for methods wherein the subject is suffering from cancer in which the cancer cells have a genetic mutation in one or more of the following genes: a tumor suppressor gene, a DNA damage repair gene, a replication stress gene, or an oncogenic driver gene. In some aspects, the present disclosure provides for methods wherein the subject is a human suffering from cancer that is TP53 deficient cancer. In some aspects, the present disclosure provides for methods wherein the subject is a human suffering from cancer that is a cancer with a mutation in the NRAS gene. In some aspects, the present disclosure provides for methods wherein the subject is a human suffering from cancer that is a cancer with a mutation in the BRCA1 gene. In some aspects, the subject is a human suffering from a cancer with a mutation or altered expression in REV7, SCHLFN-11, or combinations thereof. Rev7 can also be referred to as: MAD2B, Mitotic Arrest Deficient Like 2, MAD2, Polymerase Zeta 2 Accessory Subunit, MAD2-Like Protein 2, HREV7, Mitotic Spindle Assembly Checkpoint Protein MAD2B, FANCV and POLZ2. REV7 comprises Homo sapiens REV7 encoded by amino acid sequences and nucleotide sequences according to NCBI accession numbers: NP_006332 and NM_006341.3. SCHLFN-11 can also be referred to as: SLFN11, Schlafen Family Member 11 and SLFN8/9. SCHLFN-11 (SLFN11) comprises Homo sapiens SLFN11 encoded by amino acid sequences and nucleotide sequences according to NCBI accession numbers: NP_689483 and NM_152270.3. In some aspects, the subject has a cancer with a mutation or altered expression in BRCA, other homologous recombination genes, or combinations thereof. In some aspects, the subject has a cancer with a deficiency in the homologous recombination pathway. In certain aspects, the cancer does not have a mutation or altered expression in BRCA genes, other homologous recombination genes, or combinations thereof. In certain aspects, the cancer is proficient in the homologous recombination pathway.

In certain aspects, the cancer has a reversion mutation in BRCA or other HR gene resulting in a partial recovery of homologous recombination pathway thereby rendering the tumor cell PARPi resistant.

In certain aspects, the cancer is resistant to PARPi therapy.

In some aspects, the present disclosure provides for methods wherein the subject is a human suffering from cancer in which the cancer cells overexpress/or underexpress one or more biomarkers including: Myc, N-Myc, CCNE1, FBW7, TP53, BRAC1 and Rb1.

Administration

As disclosed herein, the methods of the invention include coadministration of the combination of a Chk1 inhibitor and a PARP inhibitor. As disclosed herein, the methods of the invention include coadministration of the combination of SRA737 and a PARP inhibitor. Coadministered encompasses methods where a Chk1 inhibitor (e.g., SRA737) and a PARP inhibitor are given simultaneously, where a Chk1 inhibitor and a PARP inhibitor are given sequentially, and where either one of, or both of, a Chk1 inhibitor and a PARP inhibitor are given intermittently or continuously, or any combination of: simultaneously, sequentially, intermittently and/or continuously. The skilled artisan will recognize that intermittent administration is not necessarily the same as sequential because intermittent also includes a first administration of an agent and then another administration later in time of that very same agent. Moreover, the skilled artisan understands that intermittent administration also encompasses sequential administration in some aspects because intermittent administration does include interruption of the first administration of an agent with an administration of a different agent before the first agent is administered again. Further, the skilled artisan will also know that continuous administration can be accomplished by a number of routes including i.v. drip or feeding tubes, etc.

Furthermore, and in a more general way, the term "coadministered" encompasses any and all methods where the individual administration of a Chk1 inhibitor and the individual administration of a PARP inhibitor to a subject overlap during any timeframe.

The frequency of administration of a Chk1 inhibitor or a PARP inhibitor to a subject is known in the art as Qnd or qnd where n is the frequency in days for successive administration of that agent. For example, Q3d would be an administration of an agent once every three (3) days. Herein the present disclosure provides for methods comprising administering either one of, or both of, or any combinations thereof, a Chk1 inhibitor and/or a PARP inhibitor to a subject for Q1d, Q2d, Q3d, Q4d, Q5d, Q6d, Q7d, Q8d, Q9d, Q10d, Q14d, Q21d, Q28d, Q30d, Q90d, Q120d, Q240d, or Q365d.

In an aspect, the present disclosure provides for methods where either one of or both of or any combination thereof a Chk1 inhibitor and/or a PARP inhibitor are administered intermittently. In an aspect, the present disclosure provides for methods comprising administering either one of, or both of, or any combinations thereof, a Chk1 inhibitor or a PARP inhibitor, to a subject with at least ten (10) minutes, fifteen (15) minutes, twenty (20) minutes, thirty (30) minutes, forty (40) minutes, sixty (60) minutes, two (2) hours, three (3) hour, four (4) hours, six (6) hours, eight (8) hours, ten (10) hours, twelve (12) hours, fourteen (14) hours, eighteen (18) hours, twenty-four (24) hours, thirty-six (36) hours, forty-eight (48) hours, three (3) days, four (4) days, five (5) days, six (6) days, seven (7) days, eight (8) days, nine (9) days, ten (10) days, eleven (11) days, twelve (12) days, thirteen (13) days, fourteen (14) days, three (3) weeks, or four (4) weeks, delay between administrations. In such aspects, the administration with a delay follows a pattern where one of or both of or any combination thereof a Chk1 inhibitor and/or a PARP inhibitor are administered continuously for a given period of time from about ten (10) minutes to about three hundred and sixty five (365) days and then is not administered for a given period of time from about ten (10) minutes to about thirty (30) days. In an aspect, the present disclosure provides for methods where either one of or any combination of a Chk1 inhibitor and/or a PARP inhibitor are administered intermittently while the other is given continuously.

In an aspect, the present disclosure provides for methods where the combination of the first effective amount of a Chk1 inhibitor is administered sequentially with the second effective amount of a PARP inhibitor.

In an aspect, the present disclosure provides for methods where a Chk1 inhibitor and a PARP inhibitor are administered simultaneously. In one aspect, the present disclosure provides for methods where the combination of the first effective amount of a Chk1 inhibitor is administered sequentially with the second effective amount of a PARP inhibitor. In such aspects, the combination is also said to be "coadministered" since the term includes any and all methods where the subject is exposed to both components in the combination. However, such aspects are not limited to the combination being given just in one formulation or composition. It may be that certain concentrations of a Chk1 inhibitor and the PARP inhibitor are more advantageous to deliver at certain intervals and as such, the first effective amount and second effective amount may change according to the formulation being administered.

In some aspects, the present disclosure provides for methods where a Chk1 inhibitor and the PARP inhibitor are administered simultaneously or sequentially. In some aspects, the present disclosure provides for methods where the first effective amount of a Chk1 inhibitor is administered sequentially after the second effective amount of a PARP inhibitor. In some aspects, the present disclosure provides for methods where the second effective amount of a PARP inhibitor is administered sequentially after the first effective amount of a Chk1 inhibitor.

In some aspects, the present disclosure provides for methods where the combination of a Chk1 inhibitor (e.g., SRA737) and a PARP inhibitor is administered in one formulation. In some aspects, the present disclosure provides for methods where the combination is administered in two (2) compositions where the first effective amount of a Chk1 inhibitor (e.g., SRA737) is administered in a separate formulation from the formulation of the second effective amount of a PARP inhibitor. In some aspects, the present disclosure provides for methods where the combination is administered in two (2) compositions where the first effective amount of the Chk1 inhibitor is administered in a separate formulation from the formulation of the second effective amount of a PARP inhibitor.

In some aspects, the present disclosure provides for methods where the first effective amount of a Chk1 inhibitor is administered sequentially after the second effective amount of a PARP inhibitor. In some aspects, the present disclosure provides for methods where the first effective amount of a Chk1 inhibitor is administered sequentially after the second effective amount of a PARP inhibitor. In some aspects, the present disclosure provides for methods where the second effective amount of a PARP inhibitor is administered sequentially after the first effective amount of a Chk1 inhibitor. In some aspects, a Chk1 inhibitor and the PARPi are administered; and subsequently both the Chk1 inhibitor and the PARPi are administered intermittently for at least twenty-four (24) hours. In some aspects, the Chk1 inhibitor and the PARPi are administered on a non-overlapping every other day schedule.

In some aspects, the present disclosure provides for methods where the first effective amount of a Chk1 inhibitor is administered no less than four (4) hours after the second effective amount of a PARP inhibitor. In an aspect, the present disclosure provides for methods where the first effective amount of a Chk1 inhibitor is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the second effective amount of a PARP inhibitor. In an aspect, the present disclosure provides for methods where the second effective amount of a PARP inhibitor is administered no less than ten (10) minutes, no less than fifteen (15) minutes, no less than twenty (20) minutes, no less than thirty (30) minutes, no less than forty (40) minutes, no less than sixty (60) minutes, no less than one (1) hour, no less than two (2) hours, no less than four (4) hours, no less than six (6) hours, no less than eight (8) hours, no less than ten (10) hours, no less than twelve (12) hours, no less than twenty four (24) hours, no less than two (2) days, no less than four (4) days, no less than six (6) days, no less than eight (8) days, no less than ten (10) days, no less than twelve (12) days, no less than fourteen (14) days, no less than twenty one (21) days, or no less than thirty (30) days after the first effective amount of a Chk1 inhibitor.

In some aspects, the present disclosure provides for methods where either one of, or both of, or any combination thereof, a Chk1 inhibitor (e.g., SRA737) and/or PARP inhibitor are administered by a route selected from the group consisting of intravenous, subcutaneous, cutaneous, oral, intramuscular, and intraperitoneal. In some aspects, the present disclosure provides for methods where either one of, or both of, or any combination thereof, a Chk1 inhibitor and/or PARP inhibitor are administered by intravenously. In some aspects, the present disclosure provides for methods where either one of, or both of, or any combination thereof, a Chk1 inhibitor and/or PARP inhibitor are administered orally.

It is understood by the skilled artisan that the unit dose forms of the present disclosure may be administered in the same or different physicals forms, i.e. orally via capsules or tablets and/or by liquid via i.v. infusion, and so on. Moreover, the unit dose forms for each administration may differ by the particular route of administration. Several various dosage forms may exist for either one of, or both of, the combination of a Chk1 inhibitor and PARP inhibitors. Because different medical conditions can warrant different routes of administration, the same components of the combination described herein may be exactly alike in composition and physical form and yet may need to be given in differing ways and perhaps at differing times to alleviate the condition. For example, a condition such as persistent nausea, especially with vomiting, can make it difficult to use an oral dosage form, and in such a case, it may be necessary to administer another unit dose form, perhaps even one identical to other dosage forms used previously or afterward, with an inhalation, buccal, sublingual, or suppository route instead or as well. The specific dosage form may be a requirement for certain combinations of a Chk1 inhibitor and PARP inhibitor, as there may be issues with various factors like chemical stability or pharmacokinetics.

Therapeutically Effective Amount and Unit Dose Form

The methods of the invention include administration of a first effective amount of a Chk1 inhibitor (e.g., SRA737) and a second effective amount of the PARP inhibitor. The term "therapeutically effective amount" is refers to an amount that is effective to ameliorate a symptom of a disease, e.g., an amount that is effective to inhibit the growth of a tumor.

A therapeutically effective amount can be the same or different than either one of, or both of, the first effective amount and the second effective amount. This is because the present disclosure provides that the methods, as described herein, are effective even where neither of the first or second effective amounts must be an amount that, alone, will ameliorate a symptom of a disease. However, the present disclosure does provide that a therapeutically effective amount of the combination must be provided, i.e. the combination does at least affect a treatment of a symptom of a disease.

A unit dose form is a term that is generally understood by the skilled artisan. A unit dose forms is a pharmaceutical drug product that is marketed for a specific use. The drug product includes the active ingredient(s) and any inactive components, most often in the form of pharmaceutically acceptable carriers or excipients. It is understood that multiple unit dose forms are distinct drug products. Accordingly, one unit dose form may be e.g., the combination of SRA737 and a PARP inhibitor of 250 mg at a certain ratio of each component, while another completely distinct unit dose form is e.g., the combination of SRA737 and a PARP inhibitor of 750 mg at the same certain ratio of each component referred to above. So from one unit dose form to another, the first effective amount and the second effective amount may both remain the same. Of course, when the either one of the first effective amount or the second effective amount changes, the unit dose form is distinct.

In some aspects, the first effective amount is unique to the Chk1 inhibitor compound, i.e. it is different than the second effective amount. In some aspects, the first effective amount is an amount that is equivalent to a "therapeutically effective amount" or an amount that brings about a therapeutic and/or beneficial effect. In some aspects, the first effective amount is a "therapeutically effective amount." In some aspects, the second effective amount is a "therapeutically effective amount." In some aspects, both the first and second effective amounts are not a "therapeutically effective amount." In some aspects, the second effective amount is unique to the PARP inhibitor compound, i.e. the second effective amount is a different amount for different PARP inhibitor compounds. In some aspects, the second effective amount is not sensitive to the identity of the PARP inhibitor and is a given amount no matter which a PARP inhibitor are in the combination.

In some aspects, the Chk1 inhibitor and a PARP inhibitor combination is formulated in one (1) unit dose form. In some aspects, the same unit dose form is administered for at least four (4) hours, six (6) hours, eight (8) hours, twelve (12) hours, twenty four (24) hours, one (1) day, two (2) days, three (3) days, seven (7) days, ten (10) days, fourteen (14) days, twenty one (21) days, or thirty (30) days.

In some aspects, the Chk1 inhibitor and a PARP inhibitor combination is formulated in at least two (2) separately distinct unit dose forms. In some aspects, the first effective amount is different in the first unit dose form than in the second unit dose form. In some aspects, the first effective amount is the same in the first unit dose form as it is in the second unit dose form.

In some aspects, the first unit dose form is the same as the second unit dose form. In some aspects, the first unit dose form is the same as the second and third unit dose forms. In some aspects, the first unit dose form is the same as the second, third, and fourth unit dose forms.

Compounds of the Invention

In one aspect, the present disclosure provides for the combination of the compound a Chk1 inhibitor (e.g., SRA737) and PARP inhibitor compound(s), and methods of use.

Chk1 Inhibitors

Chk1 inhibitors include, but are not limited to: SRA737, Prexasertib (LY2606368) (Commercially available from Sellechchem, Catalog No. S7178), PF-477736 (Commercially available from Sellechchem, Catalog No. S2904), AZD7762 (Commercially available from Sellechchem, Catalog No. S1532), Rabusertib (LY2603618) (Commercially available from Sellechchem, Catalog No. S2626), MK-8776 (SCH 900776) (Commercially available from Sellechchem, Catalog No. S2735), CHIR-124 (Commercially available from Sellechchem, Catalog No. S2683), SAR-020106 (Commercially available from Sellechchem, Catalog No. S7740) and CCT245737 (Commercially available from Sellechchem, Catalog No. S8253).

SRA737

SRA737 is interchangeable with the terms "Sierra Compound 1" and "ProNAi Compound 1" as used herein. The compound SRA737 is also identified by the chemical name: 5-[[4-[[morpholin-2-yl]methylamino]-5-(trifluoromethyl)-2-pyridyl]amino]pyrazine-2-carbonitrile. Each of the enantiomers of SRA737 is useful for compositions, methods and kits disclosed herein.

SRA737 is a compound that is disclosed in international patent application no. PCT/GB2013/051233 and U.S. Pat. No. 9,663,503, which are herein incorporated by reference in their entirety. The skilled artisan will find enabling methods for synthesizing SRA737 in international patent application no. PCT/GB2013/051233 and U.S. Pat. No. 9,663,503. The synthesis of an enantiomer of SRA737 is found in the Examples section of PCT/GB2013/051233 on pages 40-42 (Syntheses 1A-1C).

In an aspect, the SRA737 structures are as shown in the table below.

| Description | Structure |
|---|---|
| SRA737 structure | 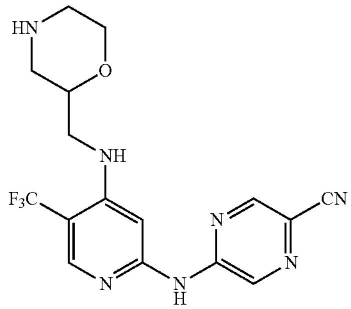 [SMILES: N#Cc1cnc(Nc2cc(NCC3CNCCO3)c(C(F)(F)F)cn2)cn1] |

PARP Inhibitors

The PARP family comprises at least 17 members, including PARP1, PARP2, VPARP (ParP4), Tankyrase-1 and -2 (PARP-5a or TNKS, and PARPa5b or TNKS2), PARP3, PARP6, TIPARP (or PARP7), PARP8, PARP9, PARP10, JPARP11, PARP12, PARP14, PARP15 and PARP16. In certain aspects, the PARP inhibitor inhibits the activity of one or more of the PARP family members. In certain aspects, the PARP inhibitor is selected from the group consisting of Olaparib, Rucaparib, Veliparib, Niraparib, Iniparib, Talazoparib, Veliparib, Fluzoparib, BGB-290, CEP-9722, BSI-201, EZ449, PF-01367338, AZD2281, INO-1001, MK-4827, SC10914, and 3-aminobenzamine. In an aspect, the PARPi is Olaparib. In an aspect, the PARPi is Niraparib. In an aspect, the PARPi is Rucaparib. In an aspect, the PARPi is Talazoparib. In an aspect, the PARPi is BGB-290.

Effective Amount

The present disclosure also provides for the combination of a Chk1 inhibitor (e.g., SRA737) and a PARP inhibitor. The present disclosure further provides for the combination of a first effective amount of a Chk1 inhibitor and a second effective amount of a PARP inhibitor. The present disclosure further provides for a pharmaceutical composition comprising a first effective amount of a Chk1 inhibitor and a second effective amount of a PARP inhibitor and at least one pharmaceutically acceptable carrier or excipient. In some aspects, the present disclosure further provides for combinations where the first effective amount and the second effective amount are each an amount from about 0.001 mg/kg to about 15 mg/kg. In some embodiments the first effective amount of a Chk1 inhibitor and/or the second effective amount of a PARP inhibitor is 0.001, 0.005, 0.010, 0.020, 0.050, 0.1, 0.2, 0.5, 1.0, 2.0, 5.0, 10.0 or 15.0 mg/kg.

Pharmaceutical Compositions of the Invention

Methods for inhibiting the growth of a tumor, inhibiting the progression of or treating cancer are described herein. Said methods of the invention include administering a therapeutically effective amount or first effective amount of Chk1 inhibitor (e.g., SRA737) and therapeutically effective amount or second effective amount of a PARP inhibitor. The Chk1 inhibitor and the PARP inhibitor can each be formulated in pharmaceutical compositions. These pharmaceutical compositions may comprise, in addition to the active compound(s), a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

A composition can be administered alone or in combination with other treatments, either simultaneously or sequentially dependent upon the condition to be treated.

In general, the compounds of the present technology will be administered in a therapeutically effective amount by any of the accepted modes of administration for agents that serve similar utilities. The actual amount of the compound of the present technology, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the present technology, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present technology is not limited to any particular composition or pharmaceutical carrier, as such may vary. In general, compounds of the present technology will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present technology is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, therapeutic agent is formulated with an excipient such as lactose. A measured amount of therapeutic agent is stored in a capsule form and is dispensed with each actuation.

Pharmaceutical dosage forms of a compound of the present technology may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present technology can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present technology in combination with at least one pharmaceutically acceptable excipient. Acceptable excipients are non-toxic, aid administration, and do not adversely affect therapeutic benefit of the claimed compounds. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the present technology in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

In some embodiments, the pharmaceutical compositions include a pharmaceutically acceptable salt. The term "pharmaceutically acceptable salt" refers to salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in Stahl and Wermuth (Eds.), Handbook of Pharmaceutical Salts Properties, Selection, and Use; 2002.

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the present technology formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present technology based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations containing the Chk1 inhibitor (e.g., SRA737) and a PARP inhibitor, either alone or in combination.

Formulation Example 1—Tablet Formulation

The following ingredients are mixed intimately and pressed into single scored tablets.

| Ingredient | Quantity per tablet (mg) |
| --- | --- |
| compound of this the present technology | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per tablet (mg) |
| --- | --- |
| compound of this the present technology | 200 |
| lactose, spray-dried | 148 |
| magnesium stearate | 25 |

Formulation Example 3—Suspension Formulation

The following ingredients are mixed to form a suspension for oral administration.

| Ingredient | Quantity per tablet (mg) |
| --- | --- |
| compound of this the present technology | 1000 |
| fumaric acid | 500 |
| sodium chloride | 2000 |
| methyl paraben | 150 |
| propyl paraben | 50 |
| granulated sugar | 25 |
| sorbitol (70% solution) | 13 |
| Veegum K (Vanderbilt Co.) | 1000 |
| flavoring | 0.035 mL |
| colorings | 500 |
| distilled water | q.s. to 100 mL |

Formulation Example 4—Injectable Formulation

The following ingredients are mixed to form an injectable formulation.

| Ingredient | Quantity per tablet (mg) |
| --- | --- |
| compound of this the present technology | 1000 |
| sodium acetate buffer solution, 0.4M | 2 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Quantity per tablet (mg) |
| --- | --- |
| compound of this the present technology | 500 |
| Witepsol ® H-15 | balance |

A composition can be administered alone or in combination with other treatments, either simultaneously or sequentially dependent upon the condition to be treated.

Kits

The present disclosure also provides for a kit comprising the combination of a Chk1 inhibitor (e.g., SRA737) and a PARP inhibitor and instructions for use. The present disclosure further provides for a kit comprising one or more pharmaceutical compositions where the pharmaceutical composition(s) comprise a Chk1 inhibitor and a PARP inhibitor, and instructions for use, optionally the combination includes at least one pharmaceutically acceptable carrier or excipient.

Individual components of the kit can be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the antigen-binding construct.

In some aspects, the disclosure provides for a kit comprising a combination of a Chk1 inhibitor (e.g., SRA737) and a PARP inhibitor and at least one pharmaceutically acceptable carrier or excipient.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits described herein also may comprise an instrument for assisting with the administration of the composition to a patient. Such an instrument may be an inhalant, nasal spray device, syringe, pipette, forceps, measured spoon, eye dropper or similar medically approved delivery vehicle.

In another aspect described herein, an article of manufacture containing materials useful for the treatment, prevention and/or diagnosis of the disorders described herein, e.g., inhibition of tumor growth is provided. The article of manufacture comprises a container and a label or package insert on or associated with the container. Suitable containers include, for example, bottles, vials, syringes, iv. solution bags, etc. The containers may be formed from a variety of materials such as glass or plastic. The container(s) holds a composition which is by itself or combined with another composition effective for treating, preventing and/or diagnosing the disorder and may have a sterile access port (for example the container may be an intravenous solution bag or a vial having a stopper pierceable by a hypodermic injection needle).

The article of manufacture in this embodiment described herein may further comprise a label or package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Polypeptide and Nucleic Acid Sequences

Described herein are polypeptide and nucleic acid sequences of genes useful for the invention, e.g., genes for CHK1. In some embodiments, polypeptide and nucleic acid sequences useful for the invention are at least 95, 96, 97, 98, or 99% identical to sequences described herein or referred to herein by a database accession number. In some embodiments, polypeptide and nucleic acid sequences useful for the invention are at least 95, 96, 97, 98, or 99% identical to any alternatively spliced analog sequences described herein or referred to herein by a database accession number. In some embodiments, polypeptide and nucleic acid sequences useful for the invention are 100% identical to sequences described herein or referred to herein by a database accession number.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Screening Methods

Briefly, cell lines were preserved in liquid nitrogen and thawed and expanded in growth media containing full serum. As the cells reached expected doubling times, the screening assay began. Cells were seeded in growth media and equilibrated via centrifugation. The cell cultures were placed in incubators and then underwent treatment. Assay plates were collected and ATP levels were measured. Assay plates were incubated with combinations for seventy two (72) or ninety six (96) hours in simultaneous and sequential dosing schedules.

As a control, SRA737 ("Sierra Compound 1" or "ProNAi Compound 1") was tested alone to quantify its single agent activity against the same cancer lines, and then again in combination with PARP inhibitors so as to compare the synergistic activity of the two. A clustered analysis of their respective activity was correlated for an analysis of the target or mode-of-action. This analysis proved to be a useful method that results in an observed pattern of enhanced SRA737 activity of activity across the cell line panel.

The assays determine a comparative score based on the inhibition of cell growth as can be measured in numerous ways, for example ATP production or by MTT assay.

Potency shifting was evaluated using an isobologram, which demonstrates how much less drug is required in combination to achieve a desired effect level, when compared to the single agent doses needed to reach that effect. The isobologram was drawn by identifying the locus of concentrations that correspond to crossing the indicated inhibition level. This is done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X, C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z-\sigma_Z(C_X, C_Y)$ and $Z+\sigma_Z(C_X, C_Y)$ cross $I_{cut}$, where $\sigma_Z$ is the standard deviation of the residual error on the effect scale.

These assays were used to assess the combination of SRA737 and enhancers for synergy were performed in a panel of fifteen (15) human cancer cell lines. The goal of the screen was to identify powerful combinations that demonstrate selective, synergistic killing of tumor cells. SRA737 was combined with PARP inhibitor compounds and tested across a cell line panel that included bladder, colorectal, lung, ovary, pancreas and head and neck cancer cell lines. The enhancer compounds chosen for inclusion in the combination with SRA737 were selected broadly amongst oncology therapeutics. The screen is also informative on the effects of dosing schedules for the compounds. Simultaneous dosing, as well as sequential dosing, was performed for each combination across the cell line panel. The screen used the ATPlite™ endpoint created forty eight (48) unique combinations.

Scoring

The results of the anti-tumor/anti-cancer assay screen were analyzed and scores were developed to compare different combinations and assess the ability of each combination to surpass single agent activity.

Growth Inhibition (GI) as a measure of cell growth. GI percentages are calculated by applying the following test and equation:

$$\text{If } T < V_0: 100 * \left(1 - \frac{T - V_0}{V_0}\right)$$

$$\text{If } T \geq V_0: 100 * \left(1 - \frac{T - V_0}{V - V_0}\right)$$

where T is the signal measure for a test article at 72 or 96 hours, V is the untreated/vehicle-treated control measure, and $V_o$ is the untreated/vehicle control measure at time zero (also colloquially referred to as $T_0$ plates). This formula is derived from the Growth Inhibition calculation used in the National Cancer Institute's NCI-60 high throughput screen.

Also, inhibition is a measure of cell viability. Inhibition levels of 0% represent no inhibition of cancer cell growth and 100% represents no doubling of cell numbers during treatment. Inhibition Percentage is calculated as the following:

$$I = 1 - T/U$$

where T is treated and U is untreated.

Synergy Score

The scalar Synergy Score was devised to quantify synergistic interactions for the combinations. The Synergy Score is calculated as:

$$\text{Synergy Score} = \log f_X \log f_Y \Sigma \max(0, I_{data})(I_{data} - I_{Loewe})$$

Loewe Volume Score

Loewe Volume Score is calculated to quantify the magnitude of the combination activity in excess of additivity observed by a single agent. Additivity is calculated:

$$I_{Loewe} \text{ that satisfies } (X/X_I) + (Y/Y_I) = 1$$

where XI and YI are the single agent effective concentrations for the observed combination effect I.

Single Agent Assessment

Cell lines that have been preserved in liquid nitrogen were thawed and expanded in growth media containing full serum. Once cells have reached expected doubling times, screening began. Cells were seeded in growth media in black 384-well tissue culture treated plates at cell densities as listed in Appendix 1 incorporated into and part of this specification. Cells were equilibrated in assay plates via centrifugation and placed in incubators (attached to the Dosing Modules) at 37° C. for 24 hours before treatment. At the time of treatment, a set of assay plates (which do not receive treatment) were collected and ATP levels were measured by detection of ATP metabolism using an ATP monitoring luminescence detection assay (ATPLite™ commercially available from Perkin Elmer). These Tzero ($T_0$) plates were read using ultra-sensitive luminescence on Envision plate readers. Assay plates were incubated with compounds for 72 and were then analyzed using ATPLite™.

Chalice Analyzer allows two ways of visualizing single agent dose response curves. The Logistics Curve fit modeling in Analyzer uses sigmoidal modeling of the data points. In most contexts, the Logistics Curve fit will accurately model the dose response curve. All subsequent analyses for the single agent and combination activities of SRA737 contained within the Examples use the Linear Interpolation Curve fit.

Combination Assessment

A high throughput screen for the inhibition of Chk1 with SRA737 in combination with PARP inhibitors was performed. SRA737 is interchangeable with the terms "Sierra Compound 1" and "ProNAi Compound 1" as used herein. PARP inhibitors are referred to as "partner compounds" and/or "enhancers" herein.

This combination screen was performed using the co-treatment dosing schedule for SRA737 and the partner compound (FIG. 1). Both enhance (SRA737) and enhancer (partner compound) were added at time zero (0h). Cells were exposed to SRA737 and the enhancer for the entire 72-hour treatment time. All data points were collected via automated processes and were subject to quality control and analyzed using proprietary software. Assay plates were accepted if they pass the following quality control standards: relative raw values were consistent throughout the entire experiment, Z-factor scores were greater than 0.6 and untreated/vehicle controls behaved consistently on the plate.

The Growth Inhibition (GI) was utilized as a measure of cell growth. GI percentages are calculated by applying the following test and equation:

$$\text{If } T < V_0: 100 * \left(1 - \frac{T - V_0}{V_0}\right)$$

$$\text{If } T \geq V_0: 100 * \left(1 - \frac{T - V_0}{V - V_0}\right)$$

where T is the signal measure for a test article at 72 or 96 hours, V is the untreated/vehicle-treated control measure, and $V_0$ is the untreated/vehicle control measure at time zero (also colloquially referred to as $T_0$ plates). This formula is derived from the Growth Inhibition calculation used in the National Cancer Institute's NCI-60 high throughput screen.

A GI reading of 0% represents no growth inhibition and would occur in instances where the T reading at 72 or 96 hours are comparable to the V reading at the respective time period. A GI 100% represents complete growth inhibition (cytostasis) and in this case cells treated with compound for 72 or 96 hours would have the same endpoint reading as T0 control cells. A GI of 200% represents complete death (cytotoxicity) of all cells in the culture well and in this case the T reading at 72 or 96 hours will be lower than the $T_0$ control (values near or at zero). These GI calculations were used in all single agent and combination data analysis for the combination screen.

Inhibition as a measure of cell viability: Inhibition levels of 0% represent no inhibition of cell growth by treatment. Inhibition of 100% represents no doubling of cell numbers during the treatment window. Both cytostatic and cytotoxic treatments can yield an Inhibition Percentage of 100%. Inhibition Percentage is calculated as the following: I=1−T/U, where T is treated and U is untreated.

Synergy Score Analysis

To measure combination effects in excess of Loewe additivity, a scalar measure was used to characterize the strength of synergistic interaction termed the Synergy Score. The Synergy Score is calculated as:

Synergy Score=log $f_X$ log $f_Y\Sigma$max$(0, I_{data})(I_{data} - I_{Loewe})$

The fractional inhibition for each component agent and combination point in the matrix is calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an Idata multiplier removes noise near the zero effect level, and biases results for synergistic interactions at that occur at high activity levels. Combinations with higher maximum Growth Inhibition (GI) effects or those which are synergistic at low concentrations will have higher Synergy Scores. Those combinations with Synergy Scores that statistically supersede baseline self-cross values can be considered synergistic. The magnitude of GI effects may be linked to the growth rate of cells which varies for each cell line examined.

Potency shifting was evaluated using an isobologram, which demonstrates how much less drug is required in combination to achieve a desired effect level, when compared to the single agent doses needed to reach that effect. The isobologram was drawn by identifying the locus of concentrations that correspond to crossing the indicated inhibition level. This is done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X, C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z-\sigma_Z(C_X, C_Y)$ and $Z+\sigma_Z(C_X, C_Y)$ cross $I_{cut}$, where $\sigma_Z$ is the standard deviation of the residual error on the effect scale.

Loewe Volume Score Analysis

Loewe Volume Score is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, as in the current dataset, the Loewe Volume is assessed to examine if there is any correlation between antagonism and a particular drug target-activity or cellular genotype. This model defines additivity as a non-synergistic combination interaction where the combination dose matrix surface is indistinguishable from either drug crossed with itself.

The calculation for additivity is: $I_{Loewe}$ that satisfies $(X/X_I)+(Y/Y_I)=1$ where $X_I$ and $Y_I$ are the single agent effective concentrations for the observed combination effect I. For example, if 50% inhibition is achieved separately by 1 µM of drug A or 1 µM of drug B, a combination of 0.5 µM of A and 0.5 µM of B should also inhibit by 50%.

Figure 2:
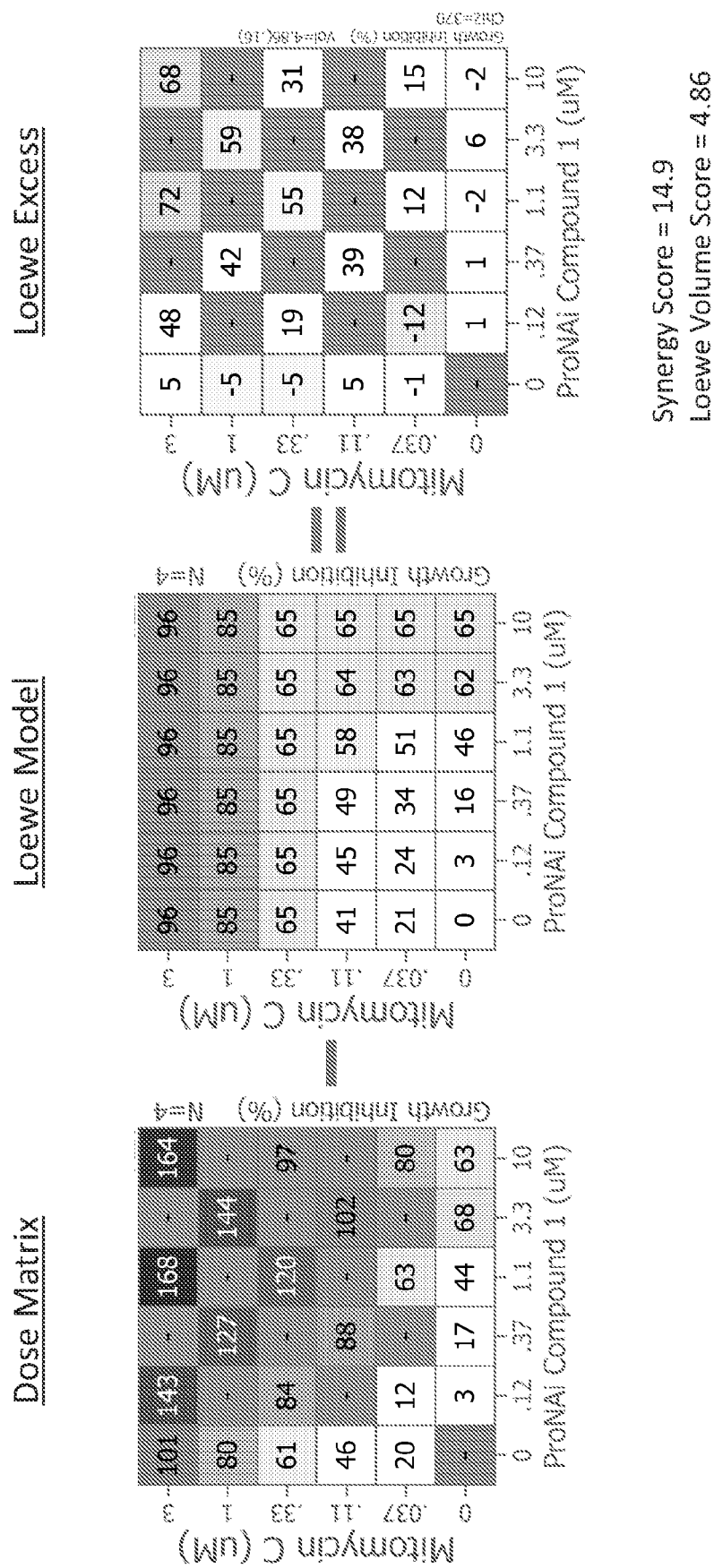
FIG. 2 illustrates dose matrix, Loewe model and Loewe excess values for determining synergy scores and Loewe volume scores for "ProNAi Compound 1" (SRA737) and Mitomycin C.
Figure 3:
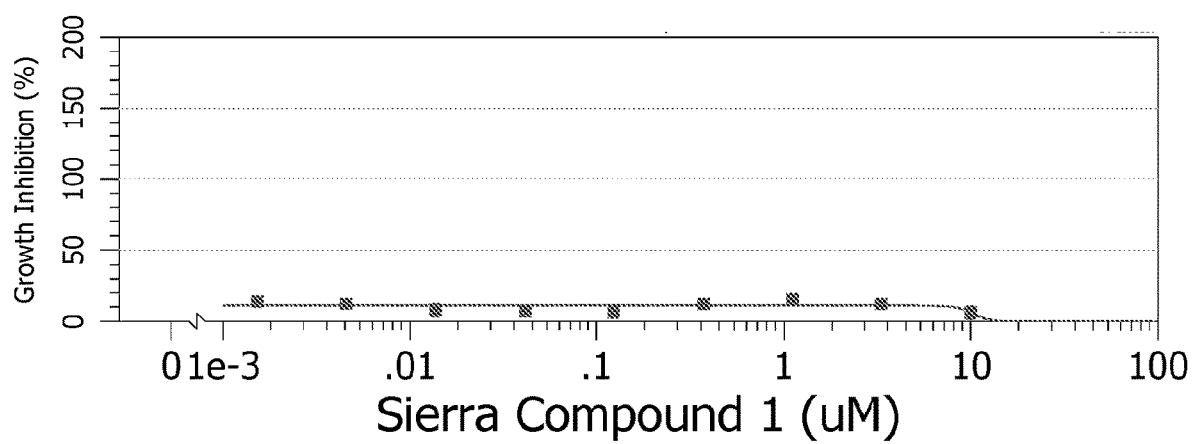
FIG. 3 shows single agent dose response profiles of CAL-27, DU-145, PC-3, HT-29 and A673 cell lines with BMN 673, Niraparib, Olaparib, Rucaparib and Sierra Compound 1 (SRA 737) agents.
Figure 3:
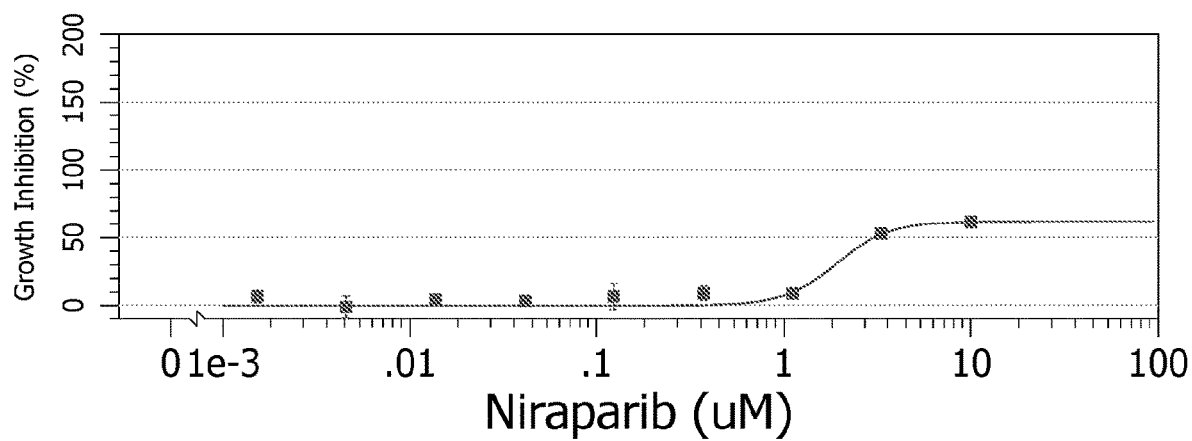
Figure 3:
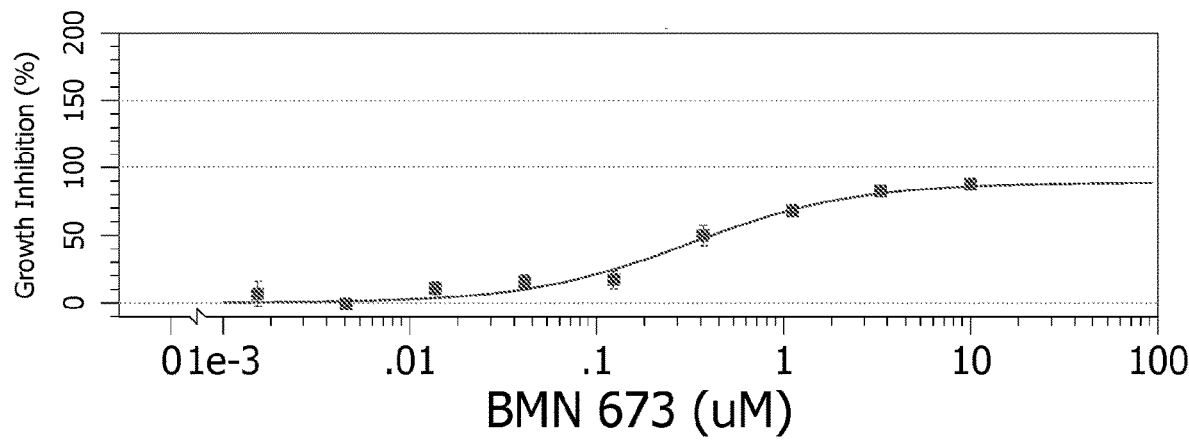
Figure 3:
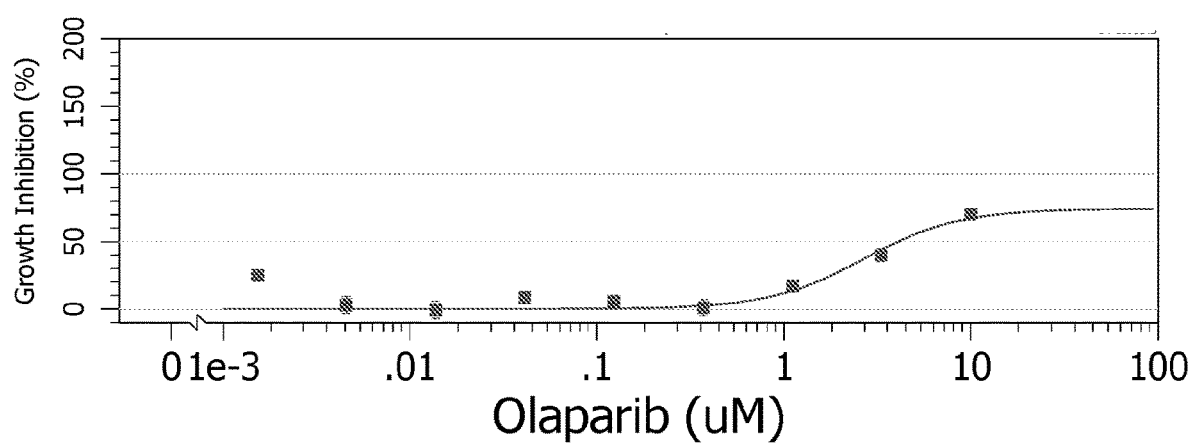
Figure 3:
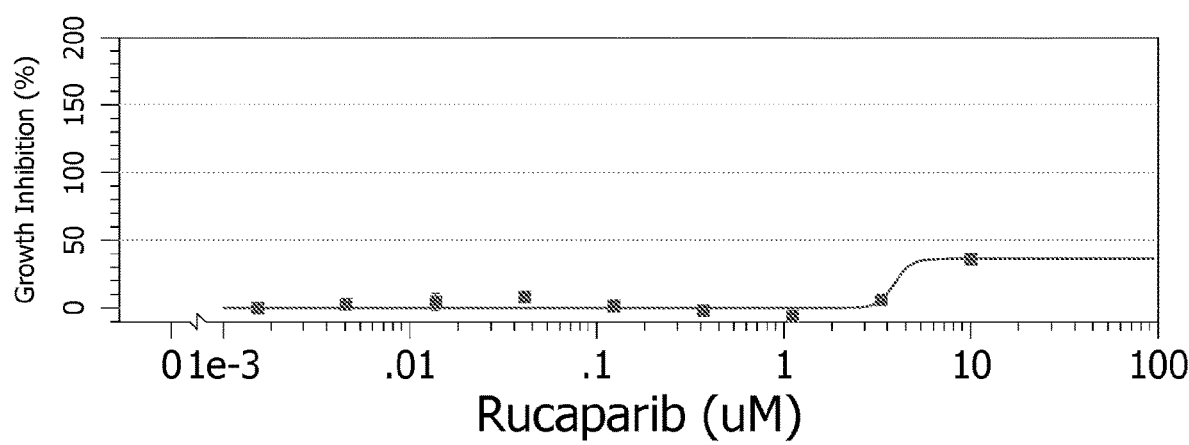
Figure 3:
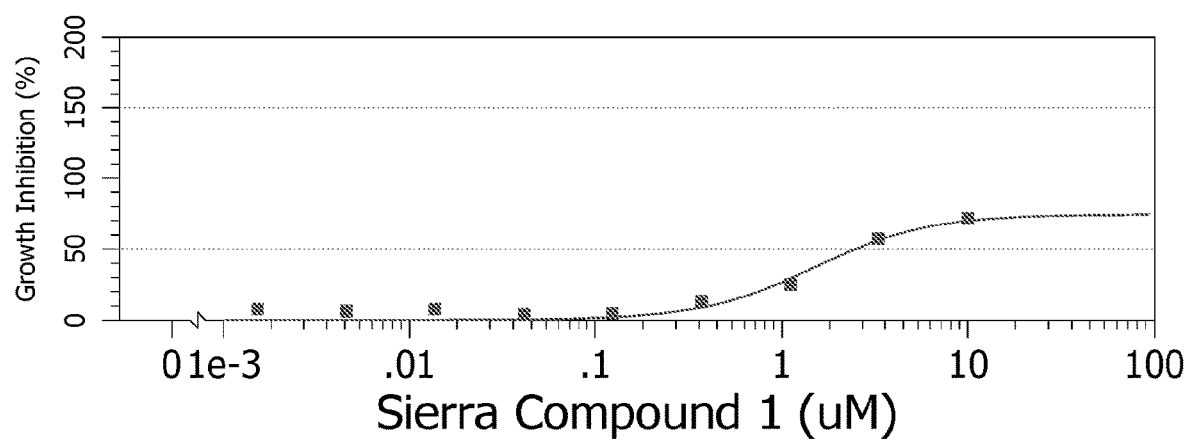
Figure 3:
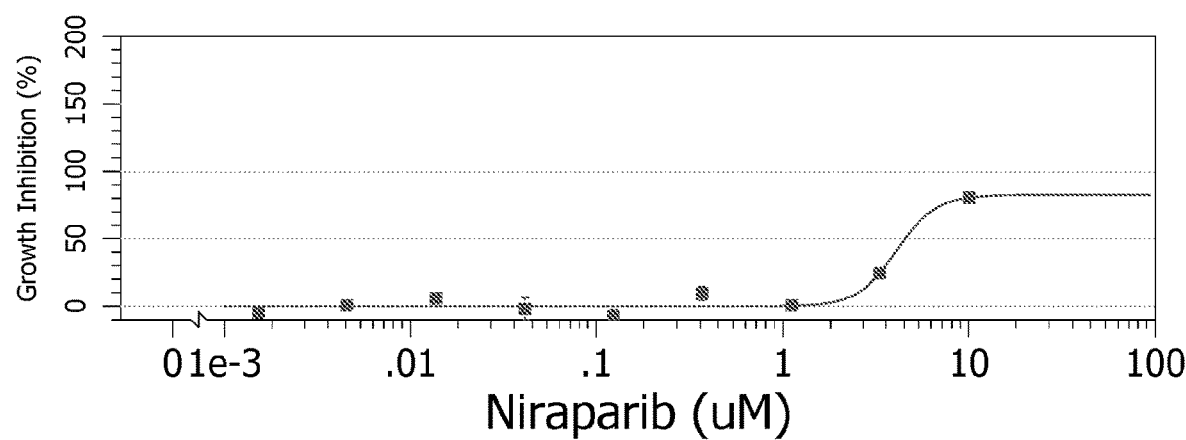
Figure 3:
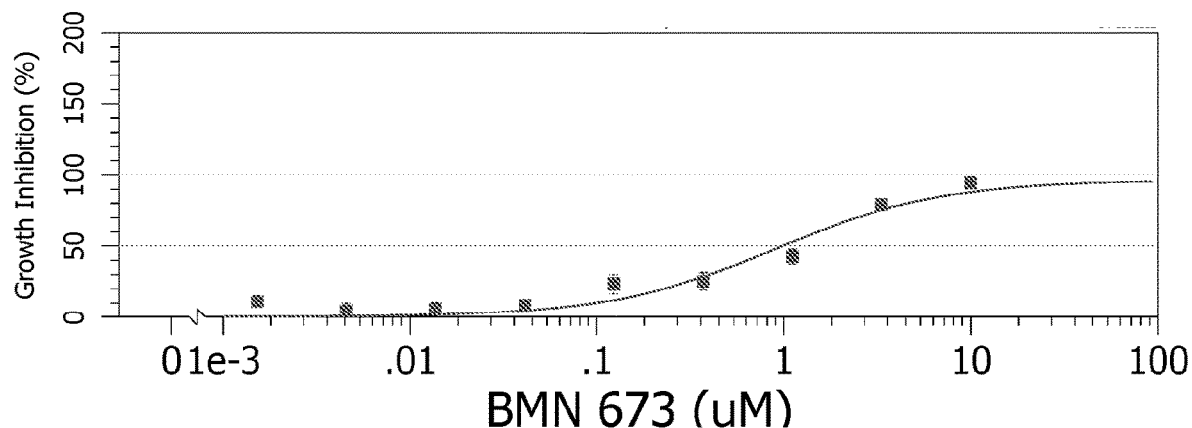
Figure 3:
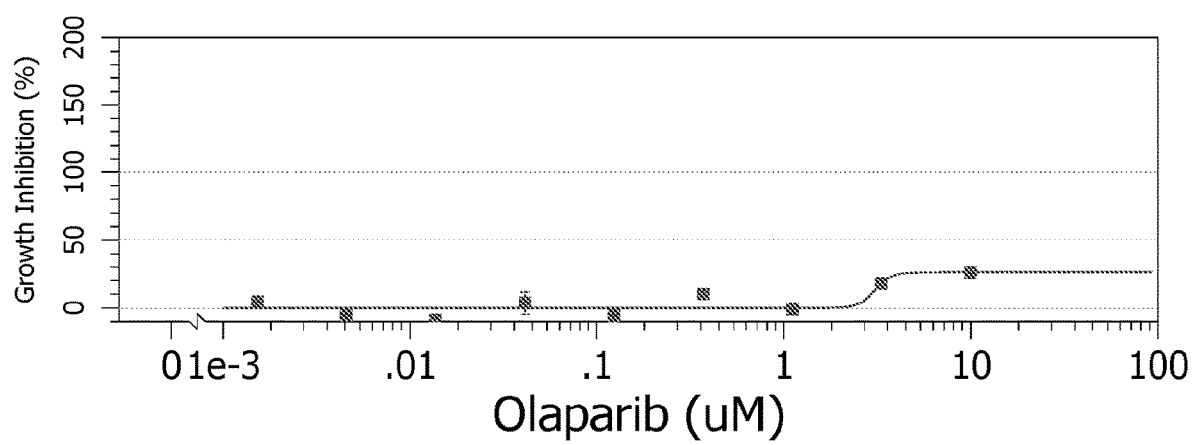
Figure 3:
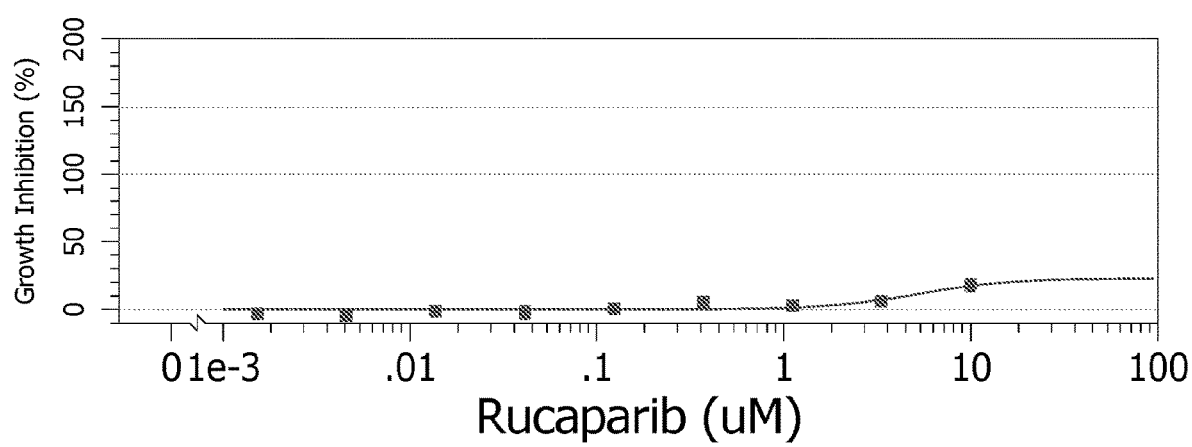
Figure 3:
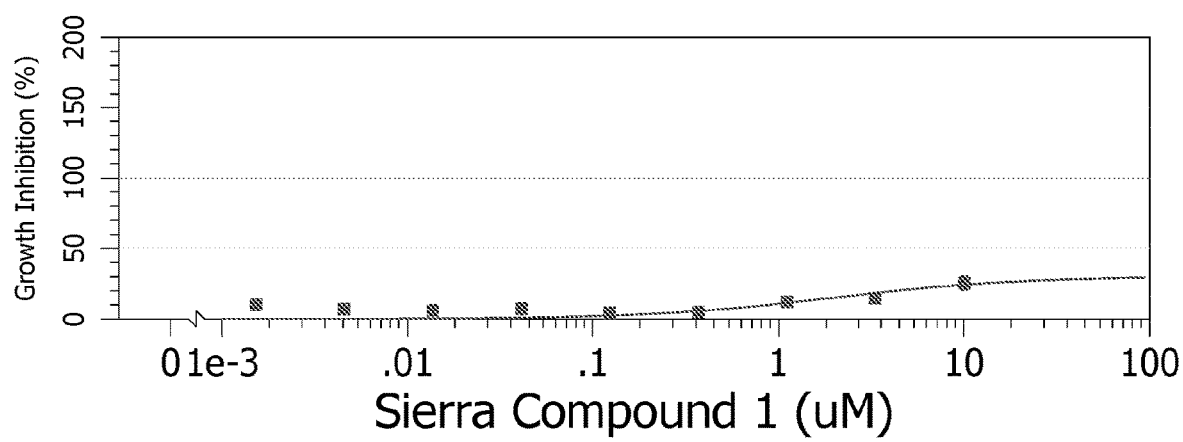
Figure 3:
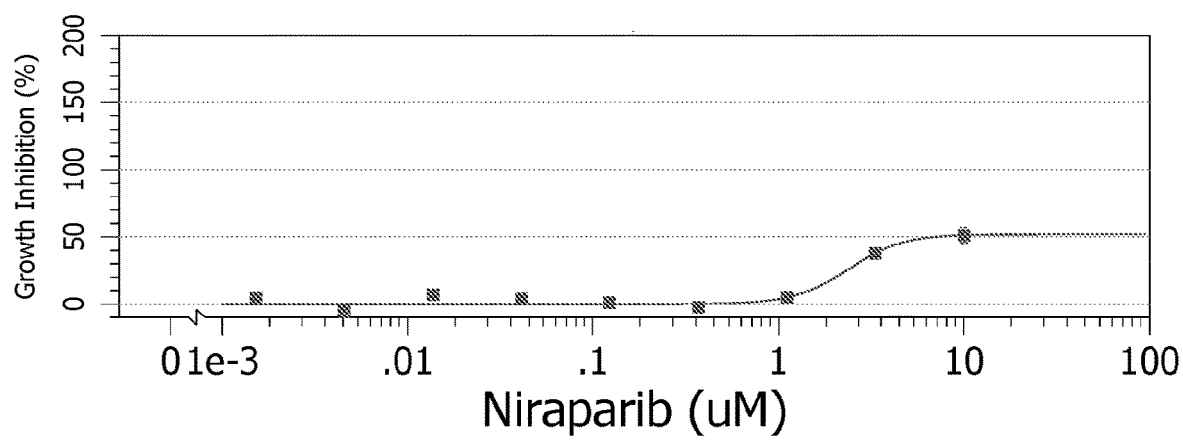
Figure 3:
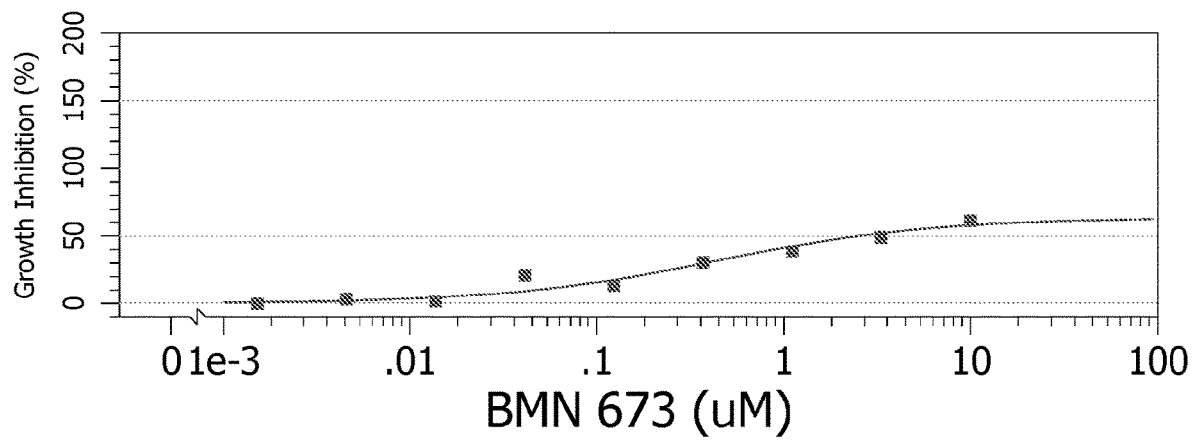
Figure 3:
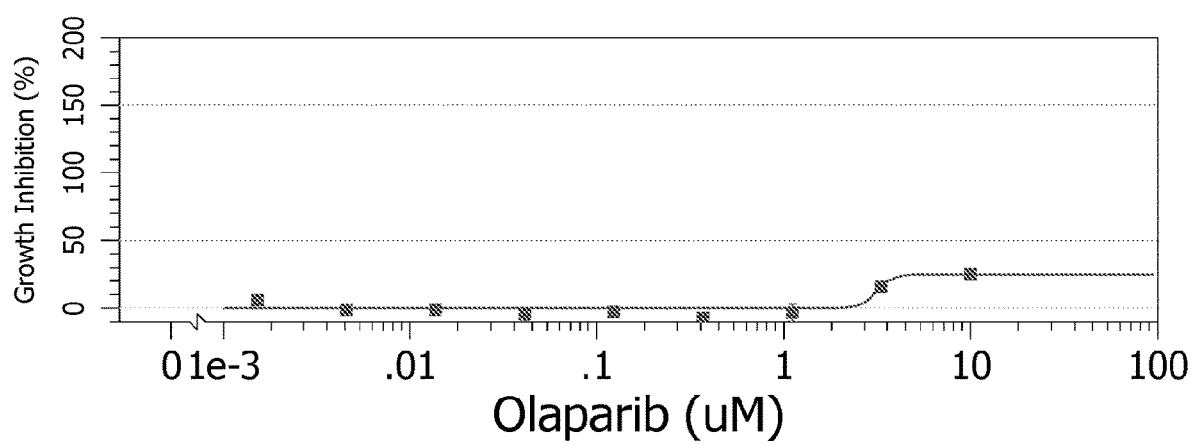
Figure 3:
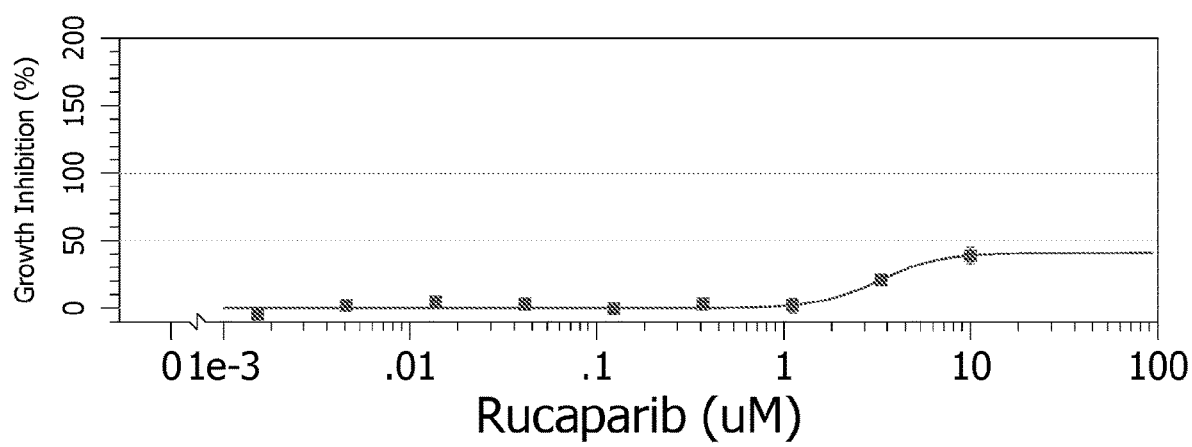
Figure 3:
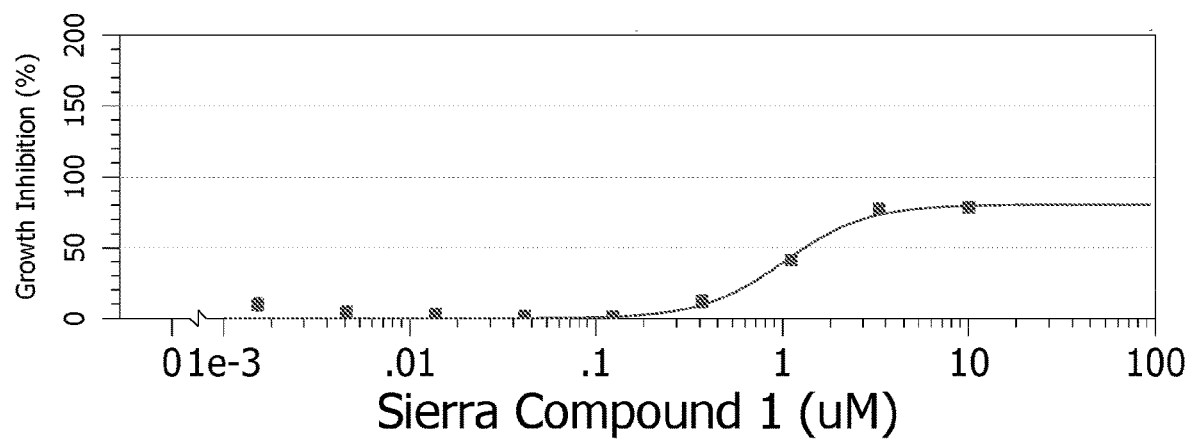
Figure 3:
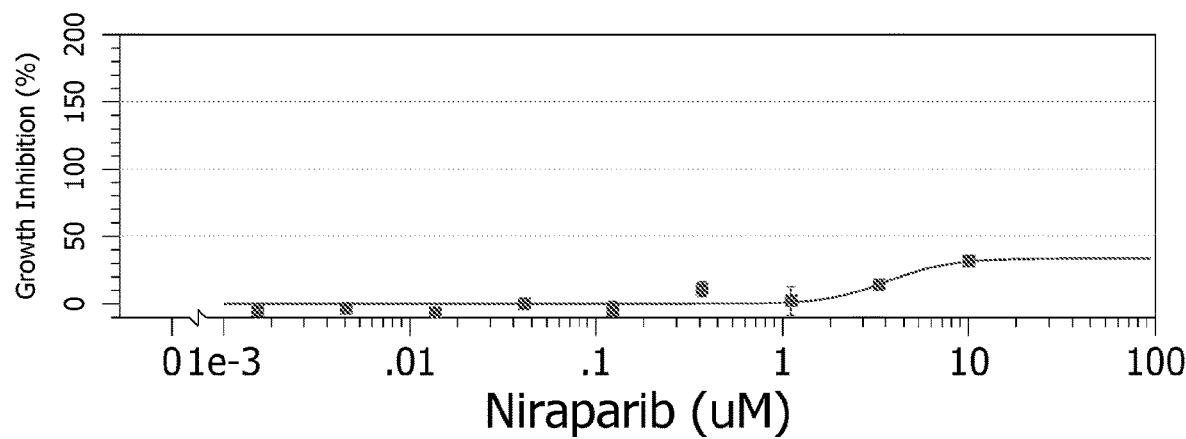
Figure 3:
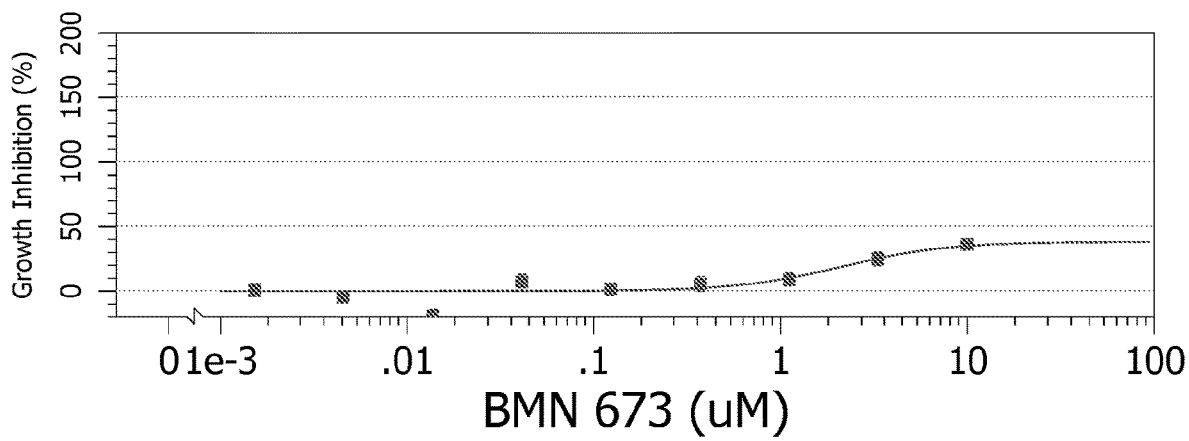
Figure 3:
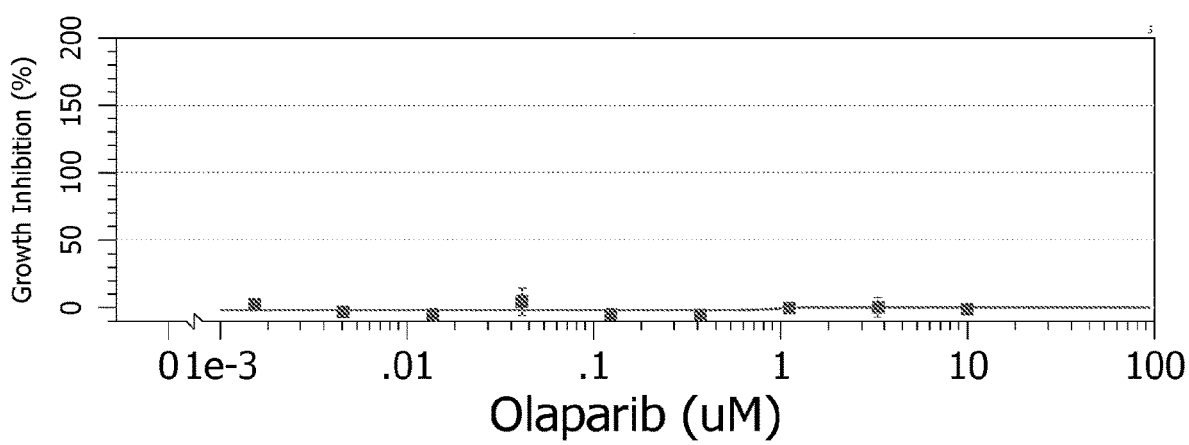
Figure 3:
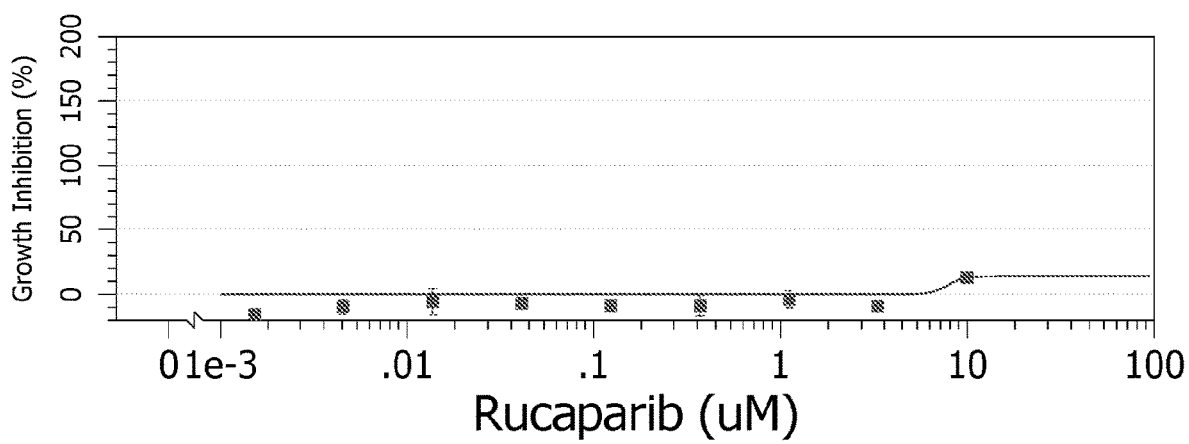
Figure 3:
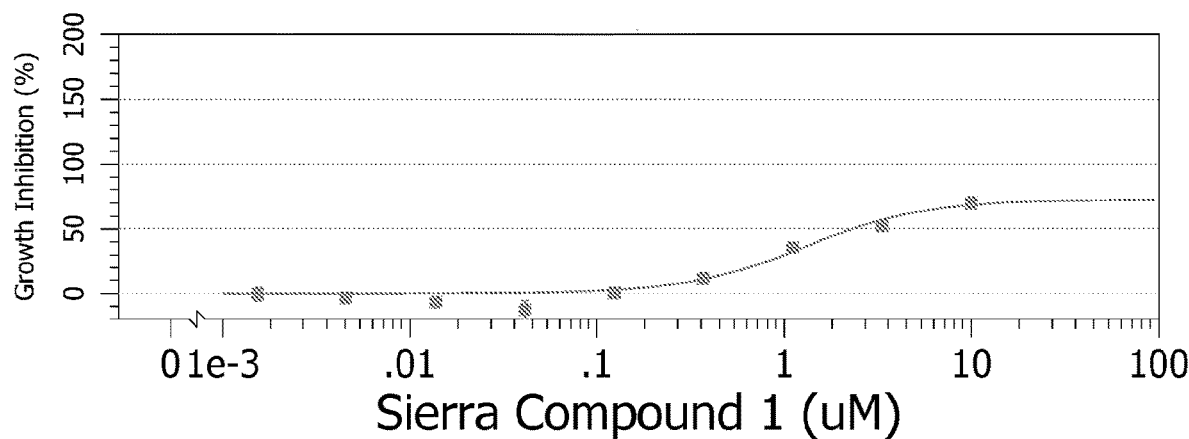
Figure 3:
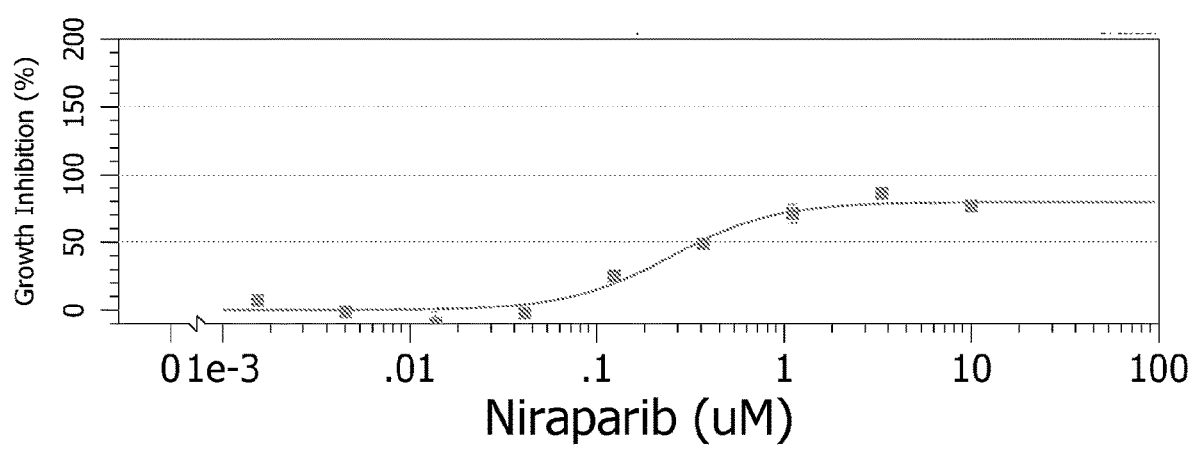
Figure 3:
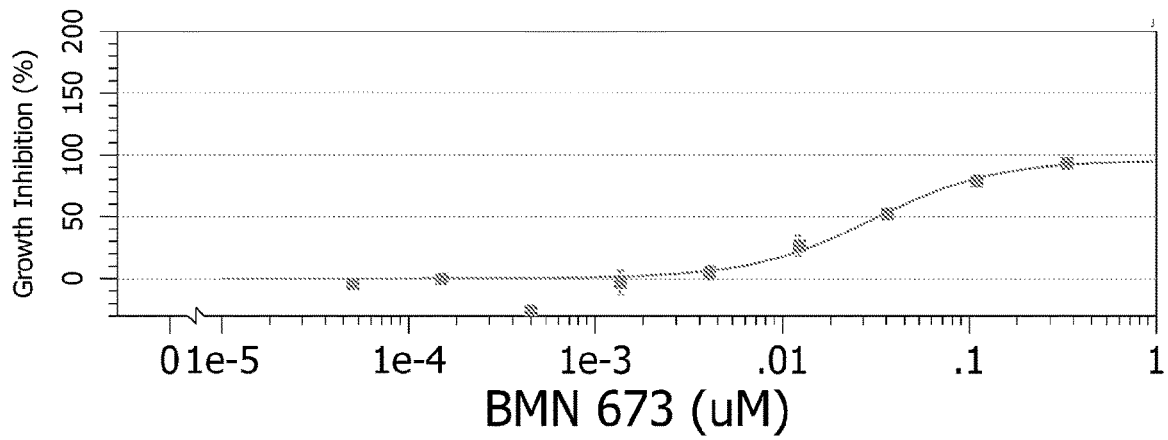
Figure 3:
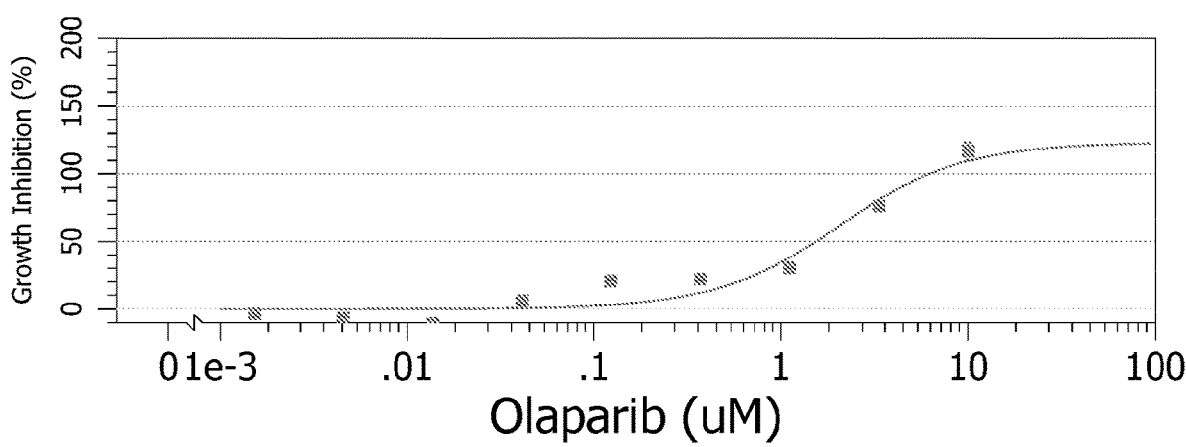
Figure 3:
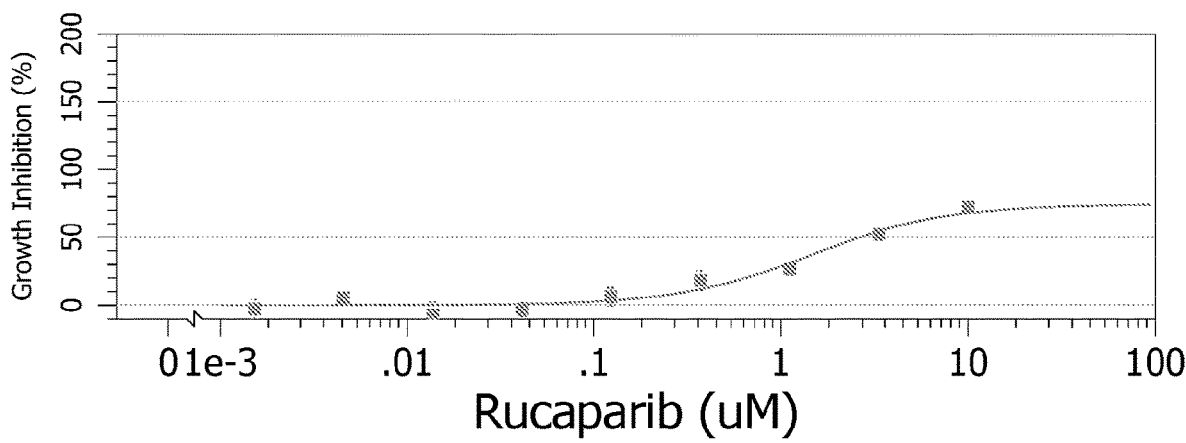
Figure 4:
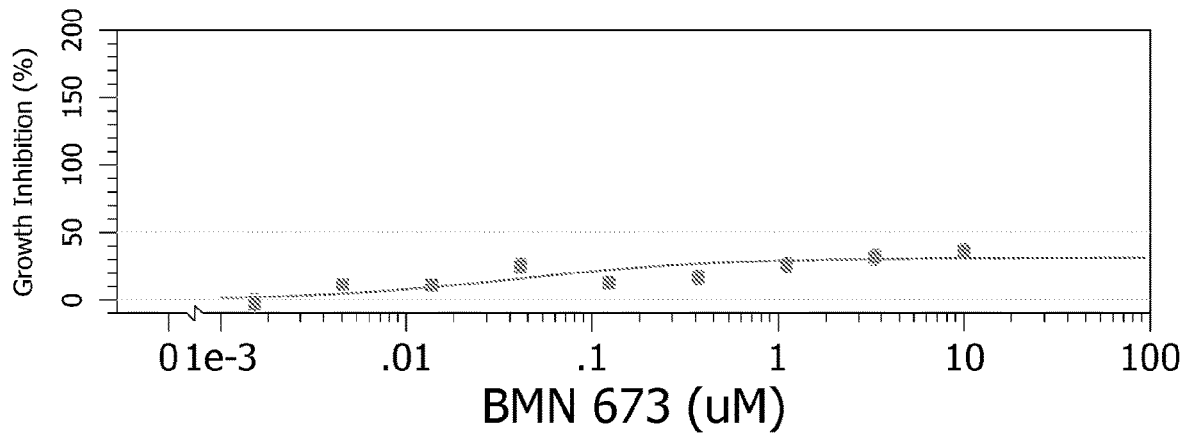
FIG. 4 shows single agent dose response profiles of BT-474, MDA-MB-231, SK-BR-3, OVCAR-3 and OVCAR-5 cell lines with BMN 673, Niraparib, Olaparib, Rucaparib and Sierra Compound 1 (SRA737) agents.
Figure 4:
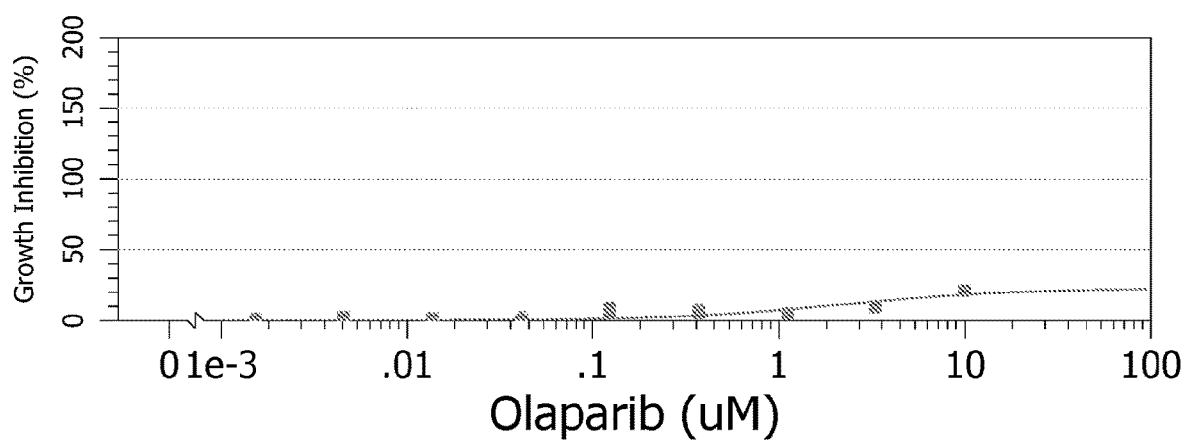
Figure 4:
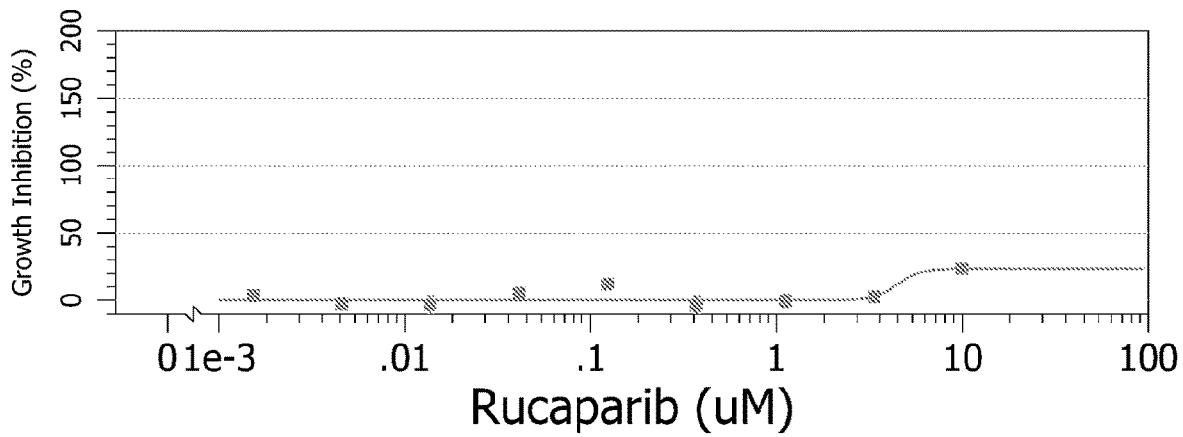
Figure 4:
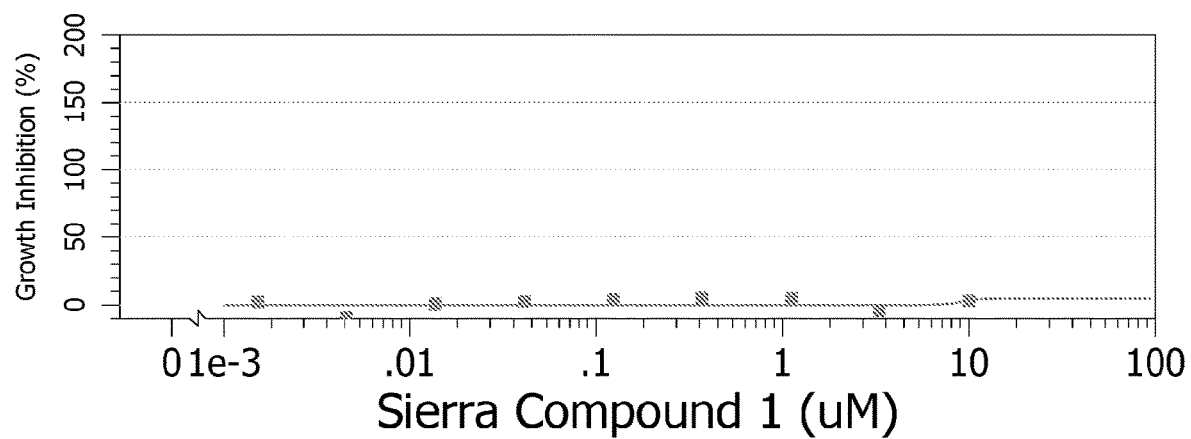
Figure 4:
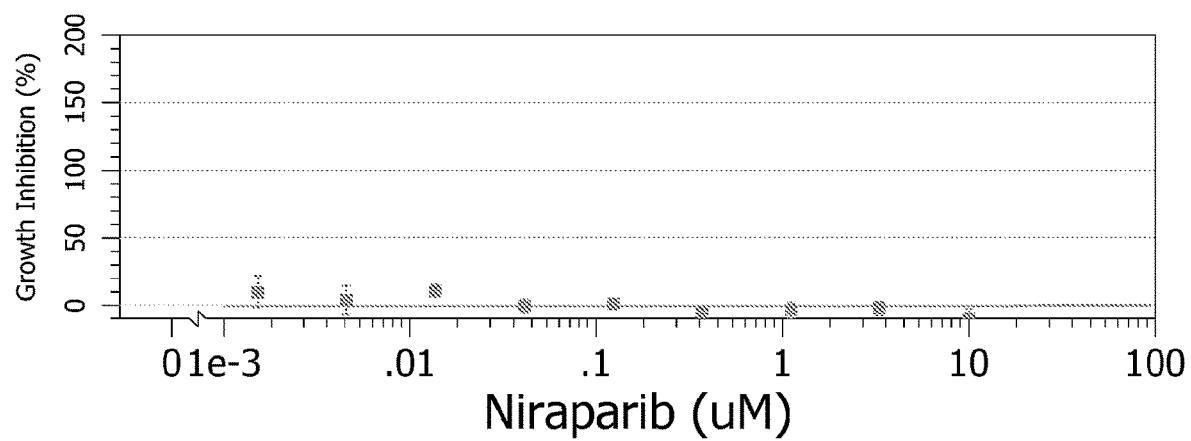
Figure 4:
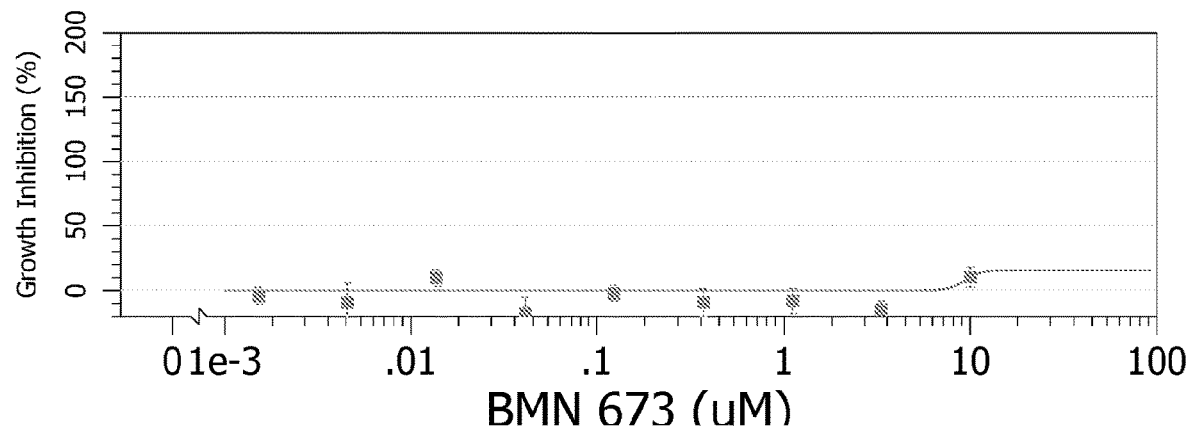
Figure 4:
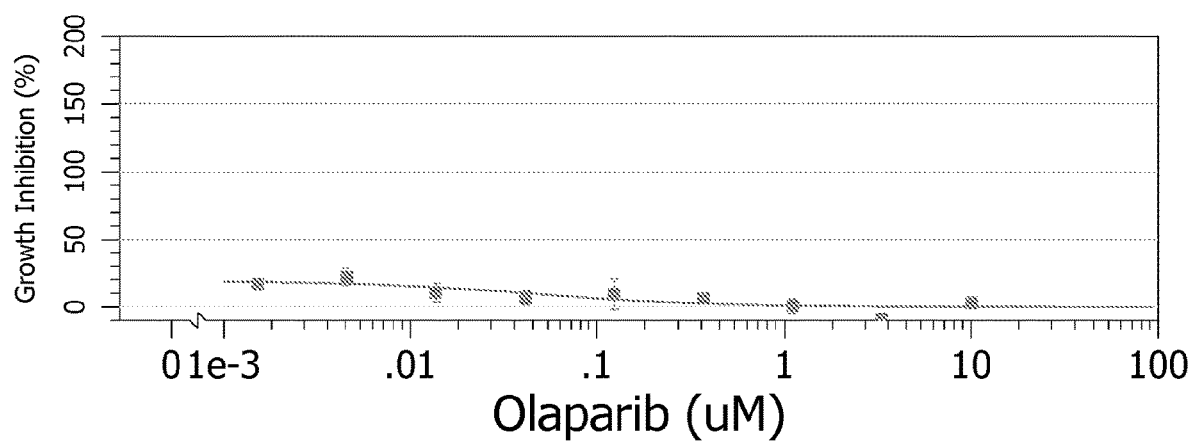
Figure 4:
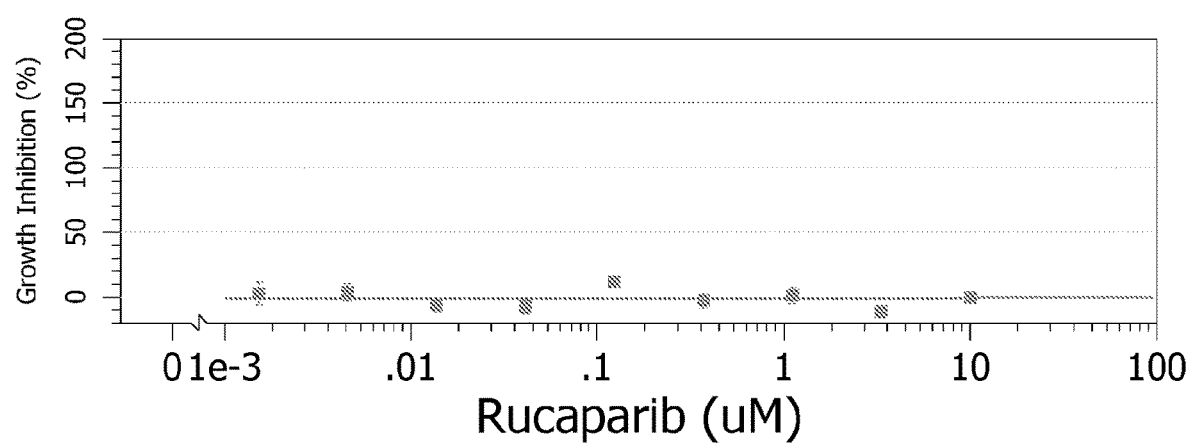
Figure 4:
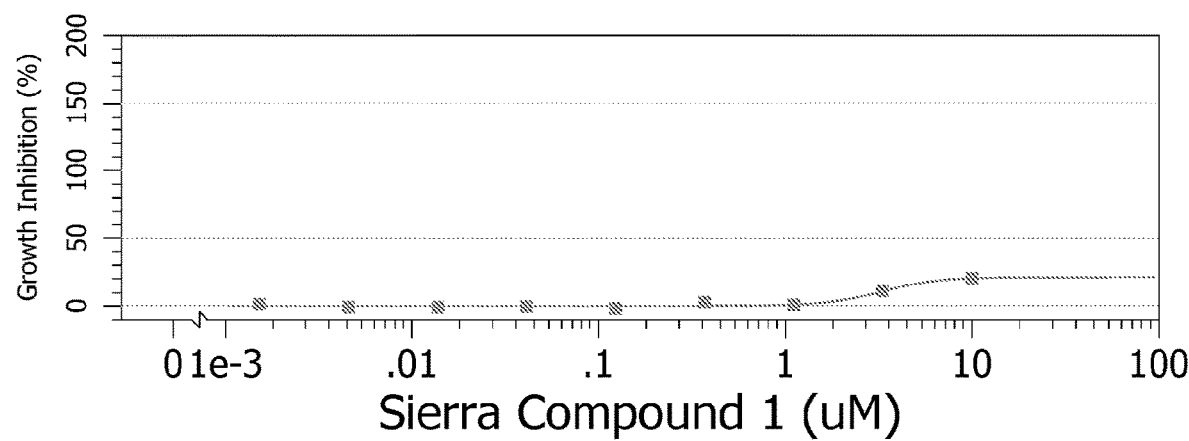
Figure 4:
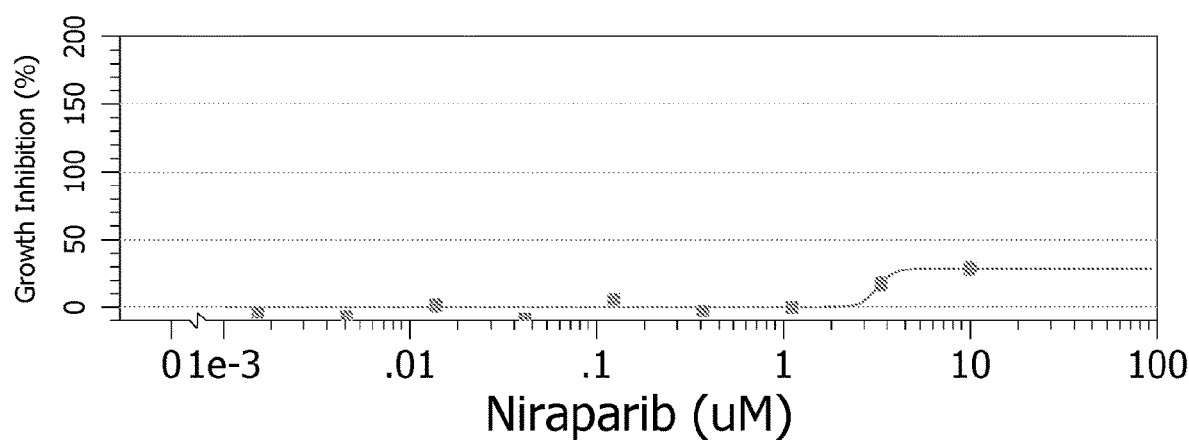
Figure 4:
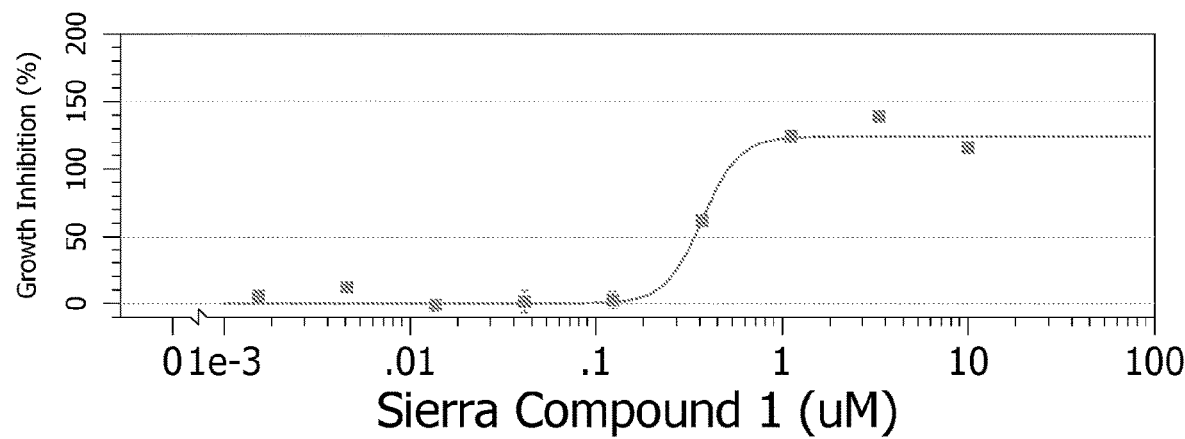
Figure 4:
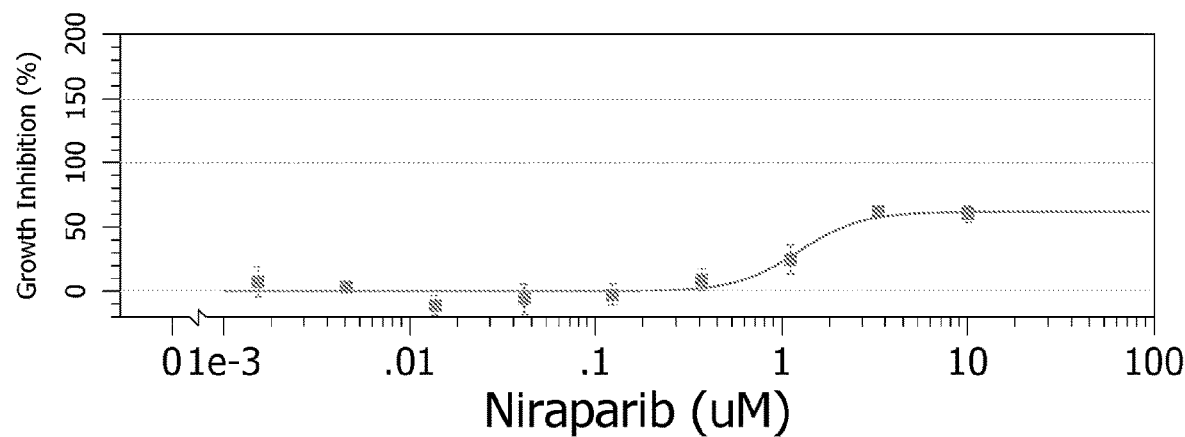
Figure 4:
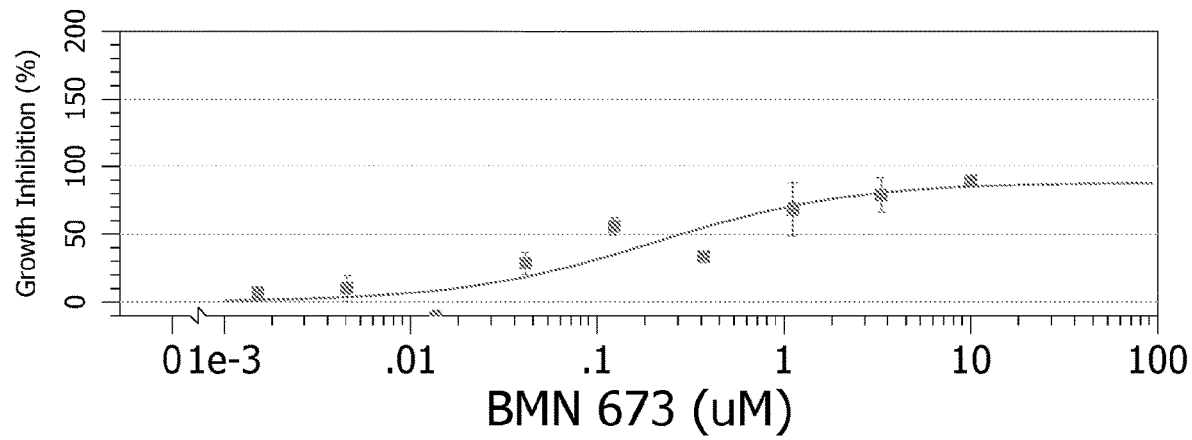
Figure 4:
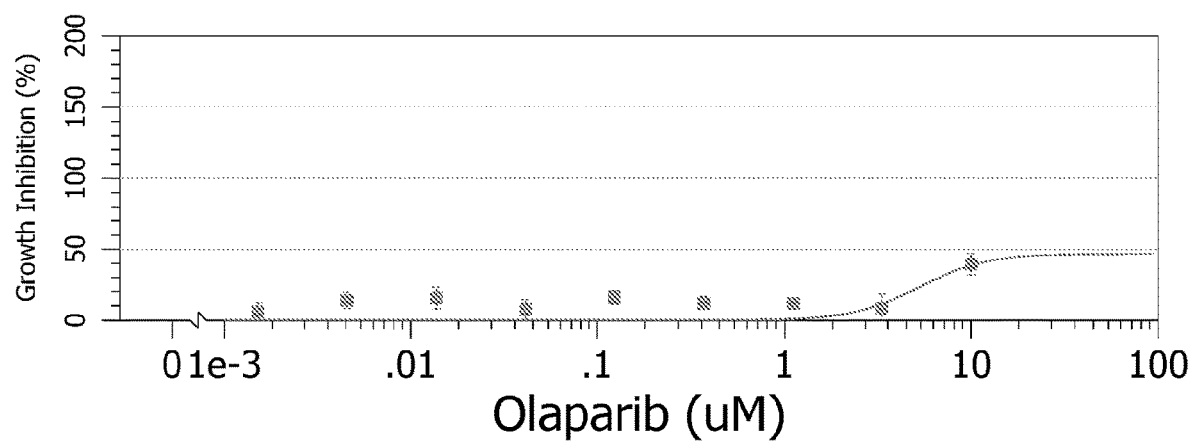
Figure 4:
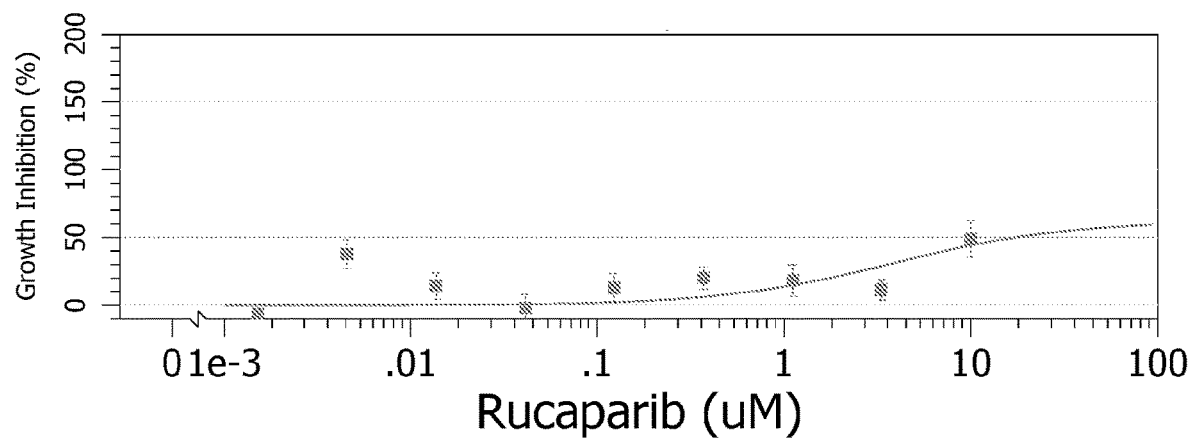
Figure 4:
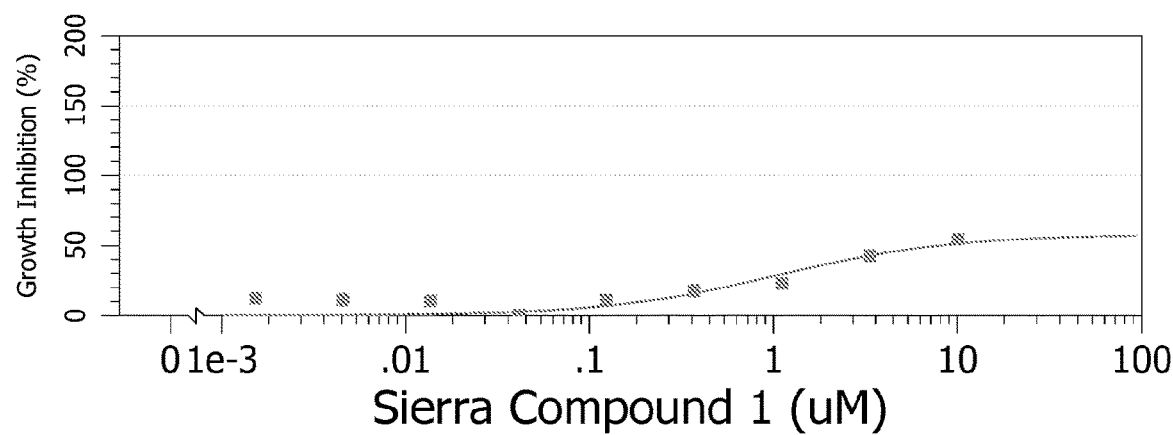
Figure 4:
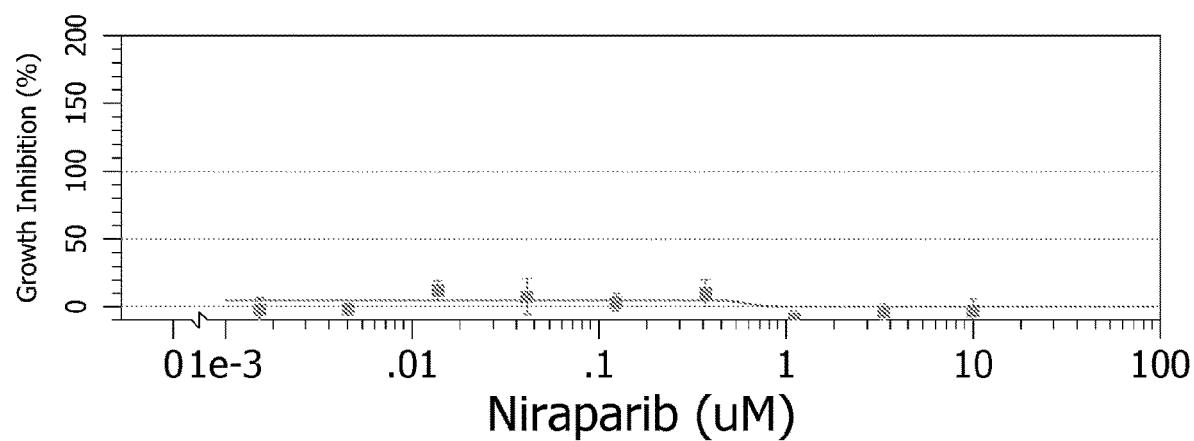
Figure 4:
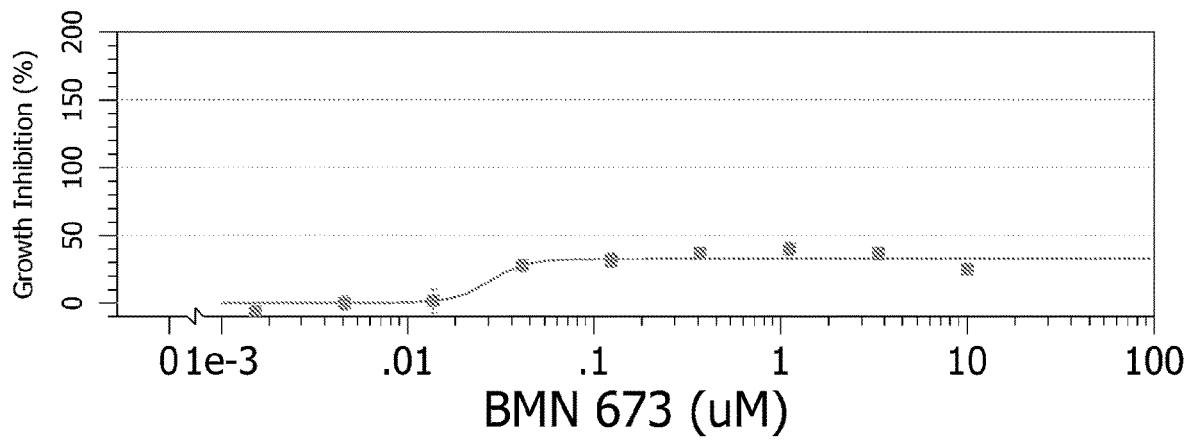
Figure 4:
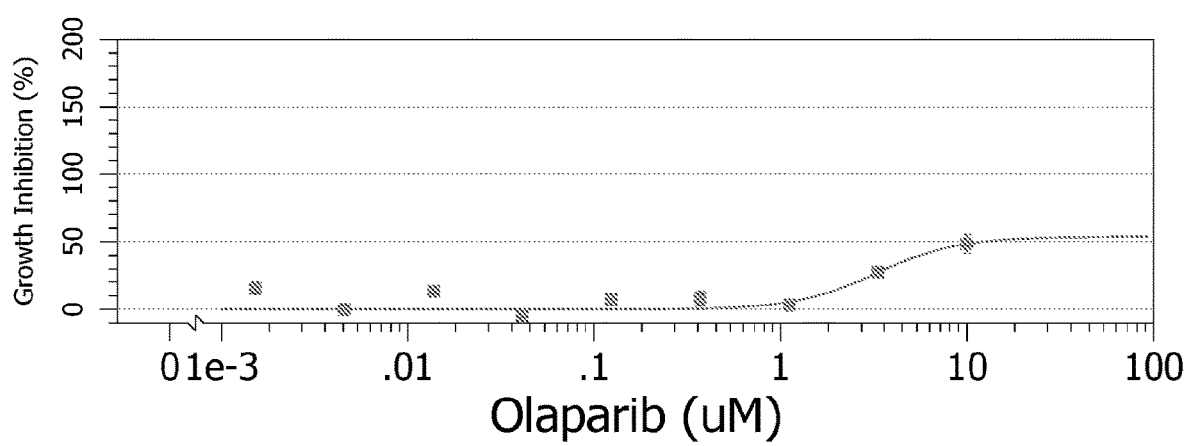
Figure 4:
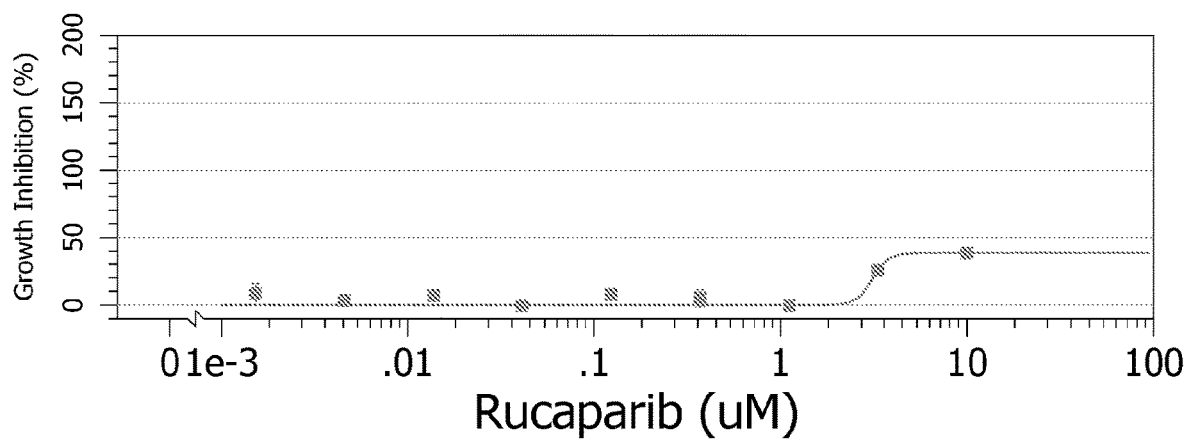
Figure 4:
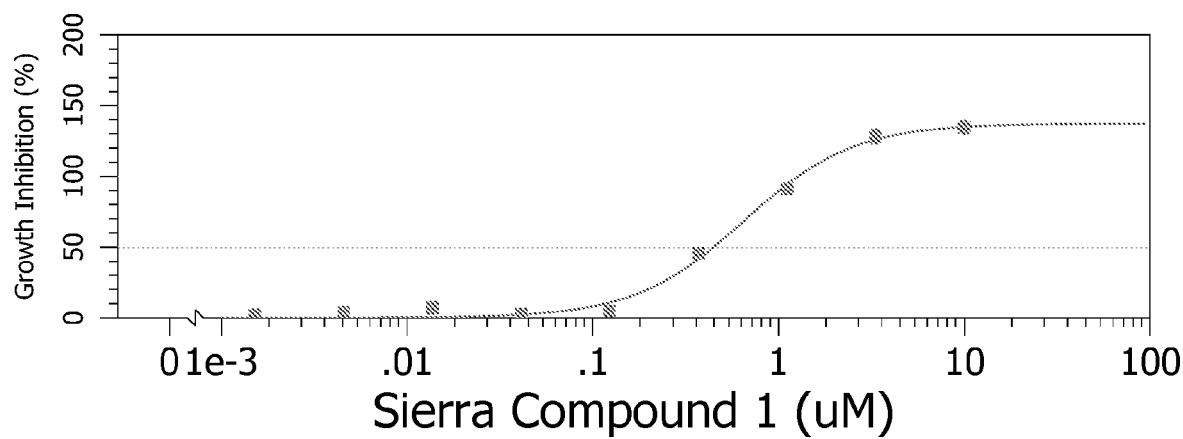
Figure 4:
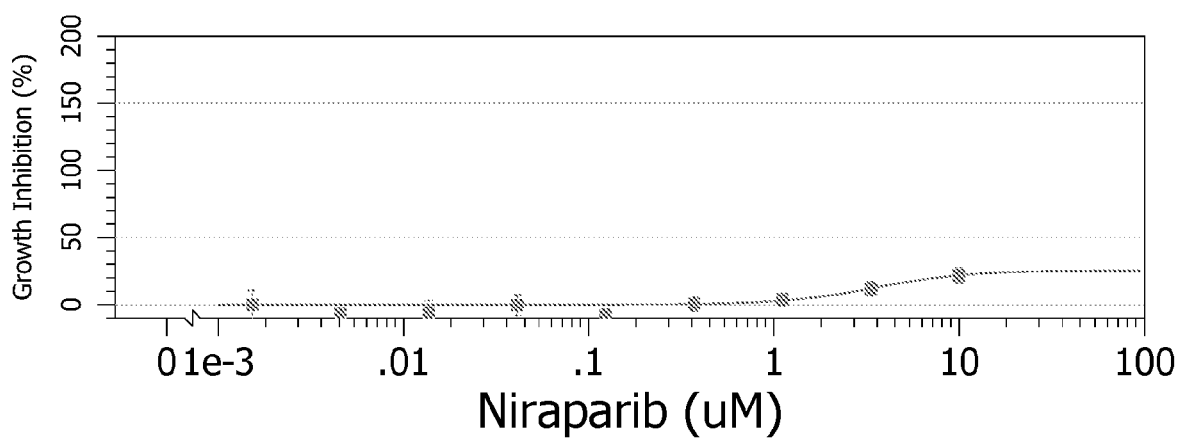
Figure 4:
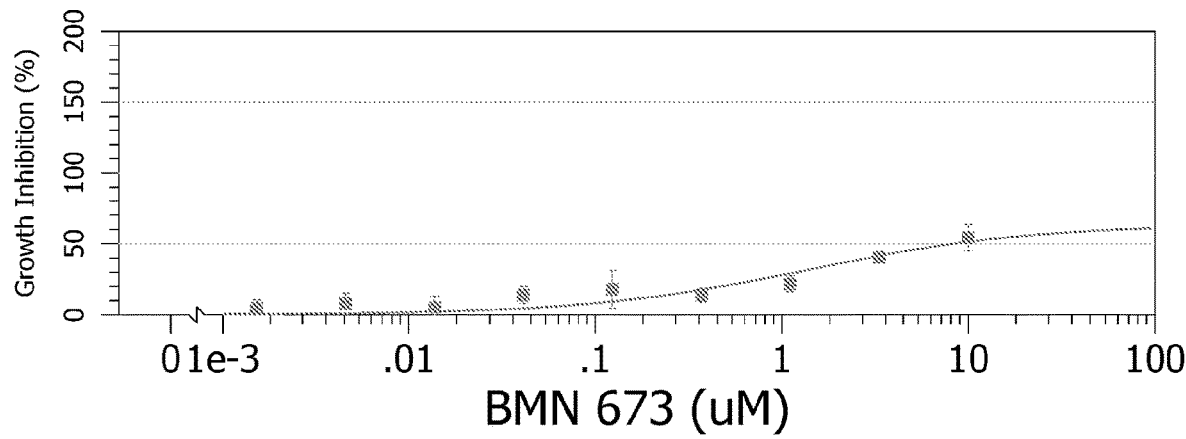
Figure 4:
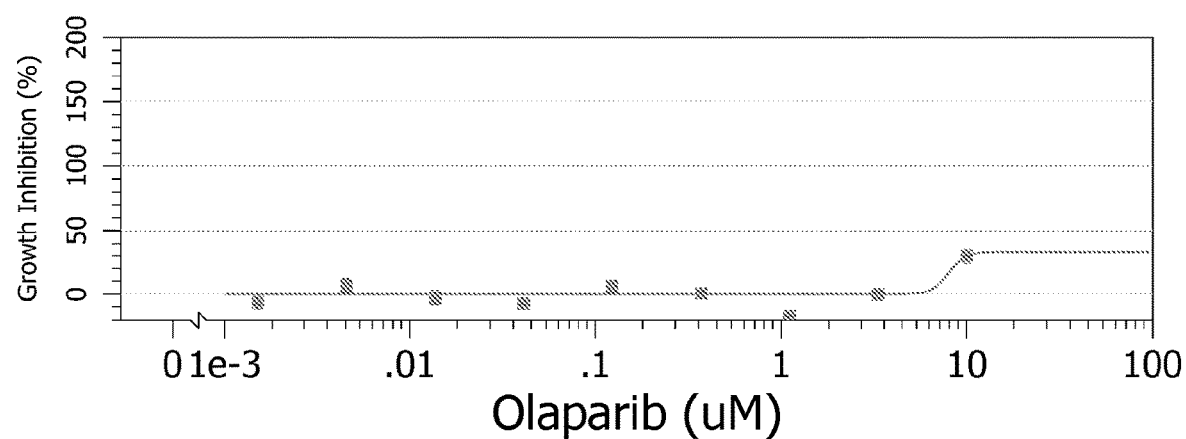
Figure 4:
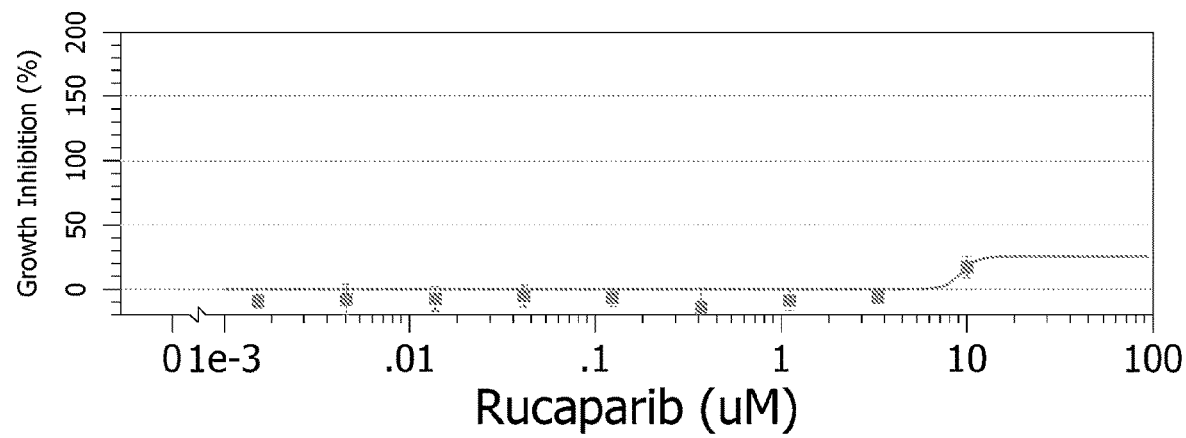

Activity observed in excess of Loewe additivity identifies synergistic interaction. For the present analysis, empirically derived combination matrices were compared to their respective Loewe additivity models constructed from experimentally collected single agent dose response curves. Summation of this excess additivity across the dose response matrix is referred to as Loewe Volume. Positive Loewe Volume suggests synergy, while negative Loewe Volume suggests antagonism (FIG. 2). As mentioned above, Synergy Score is a positively gated value and cannot be used to gauge potential antagonism Example 1: Single Agent Assessment Single agent activity of SRA737 and four PARP inhibitors in each of 10 cancer cell lines comprising breast, ovarian, prostate sarcoma and head and neck cancer cells was assessed (FIGS. 3-9). The 10 cancer cell lines examined were: A673, B-474, CAL-27, DU-145, MDA-MB-231, OVCAR-3, OVCAR-5, PC-3, HT-29 and SK-BR-3. The cell lines were screened with a 72 hour treatment schedule. Cell viability was measured by detection of ATP metabolism using an ATP monitoring luminescence detection assay (ATPLite™) GI50, IC50, Maximum Response Observed (Max Response) were calculated (FIG. 5).

Figure 6:
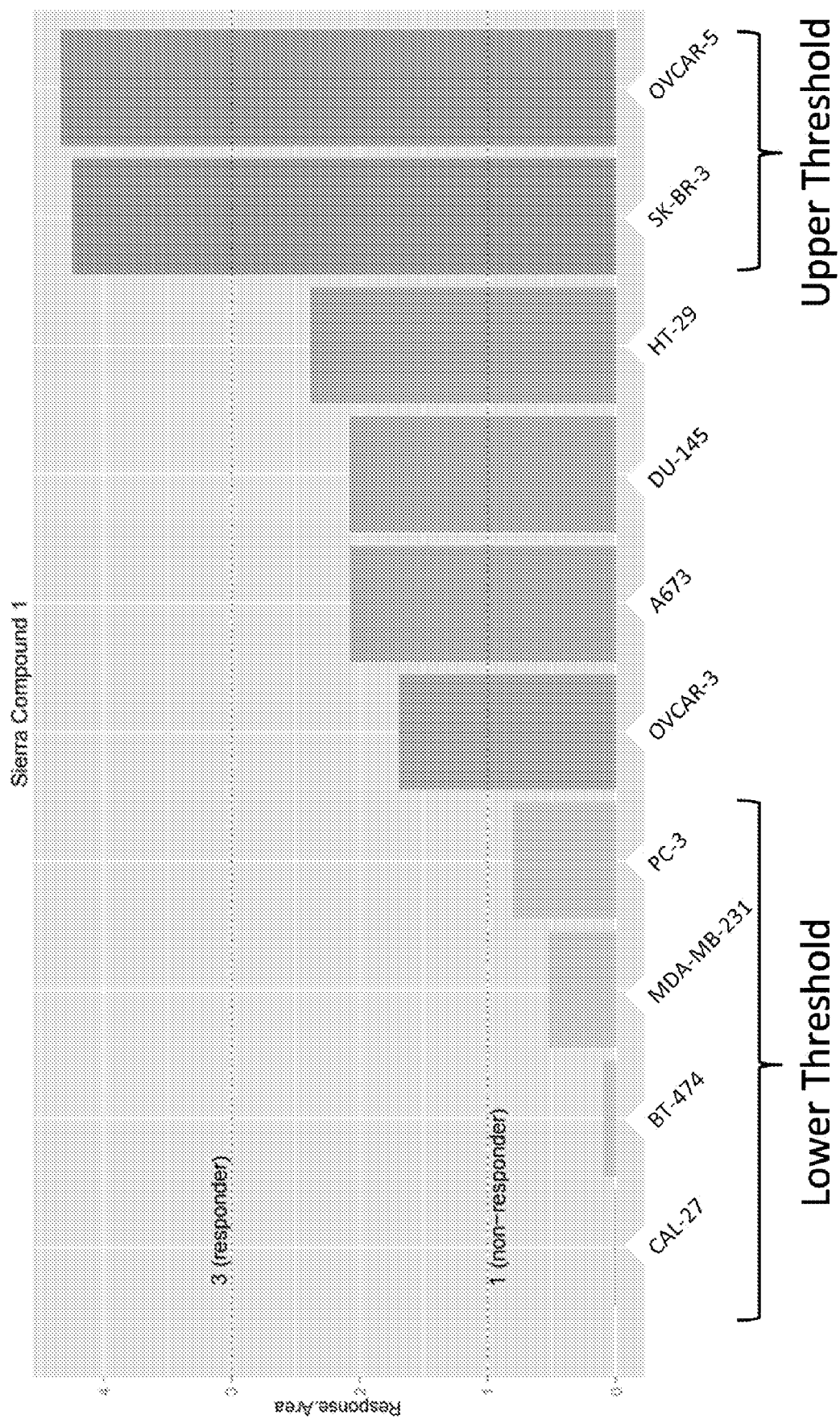
FIG. 6 shows sensitivity of cell lines to Sierra Compound 1 (SRA737) treatment.
Figure 7:
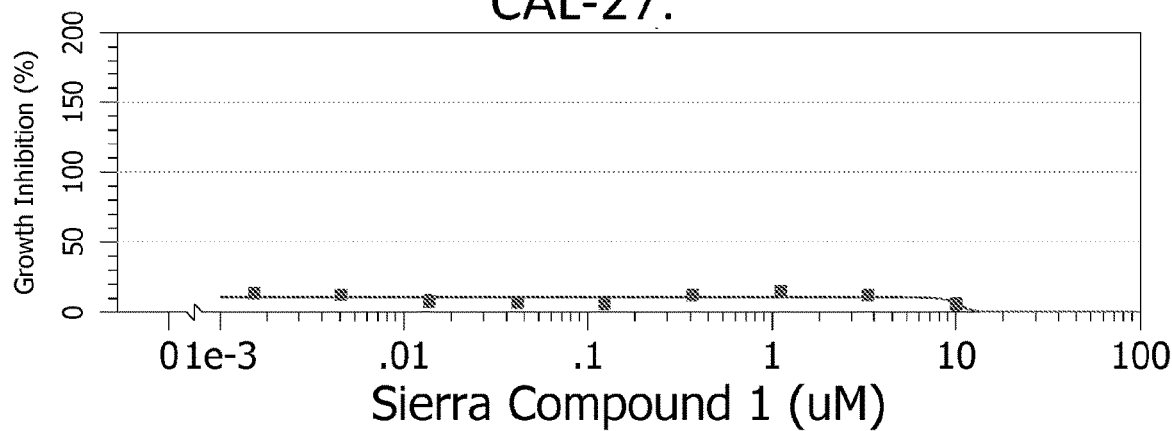
FIG. 7 shows a comparison of Sierra Compound 1 (SRA 737) single agent activity results compared to a prior study in CAL-27, HT-29 and OVCAR-3 cell lines.
Figure 7:
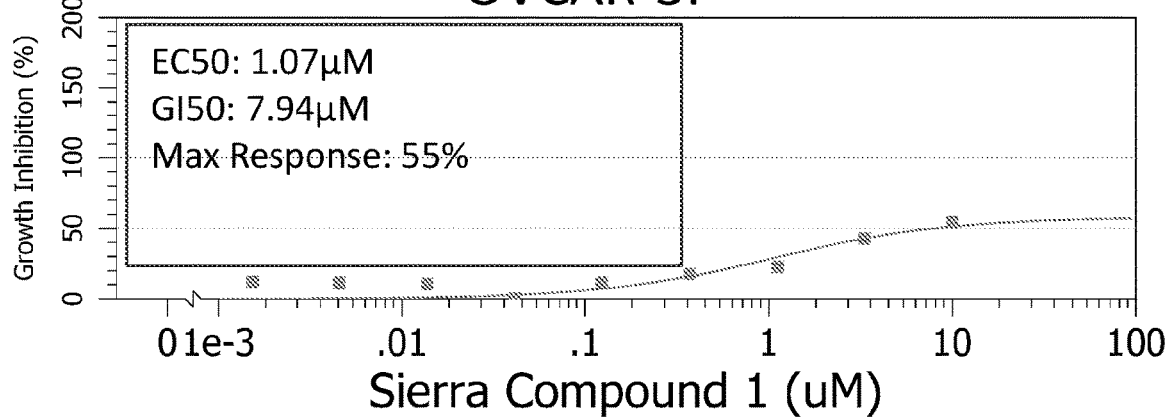
Figure 7:
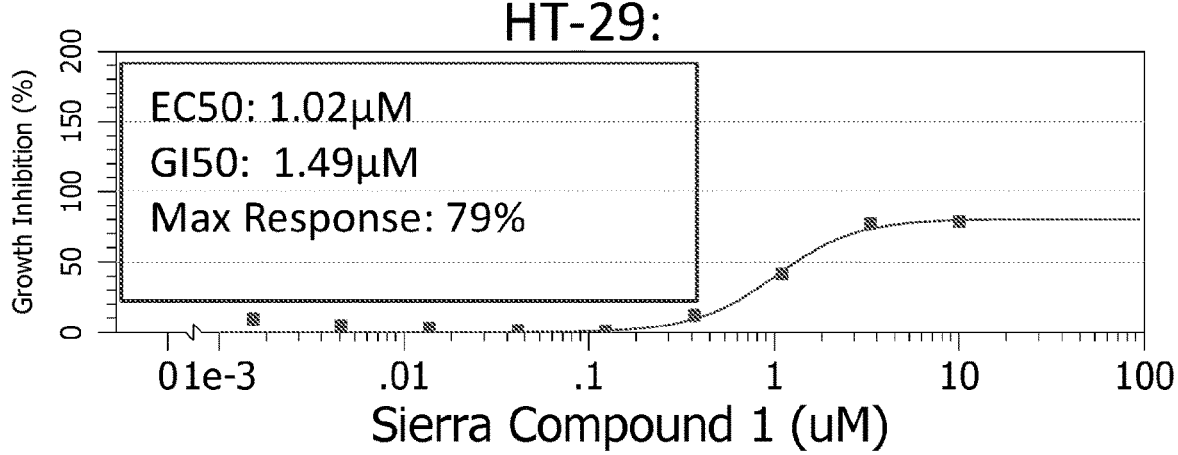
Figure 7:
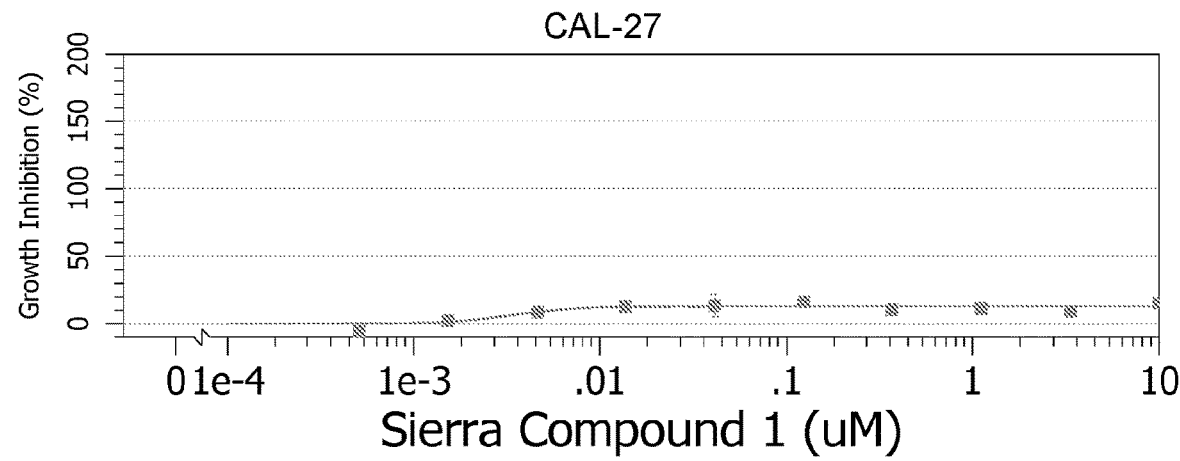
Figure 7:
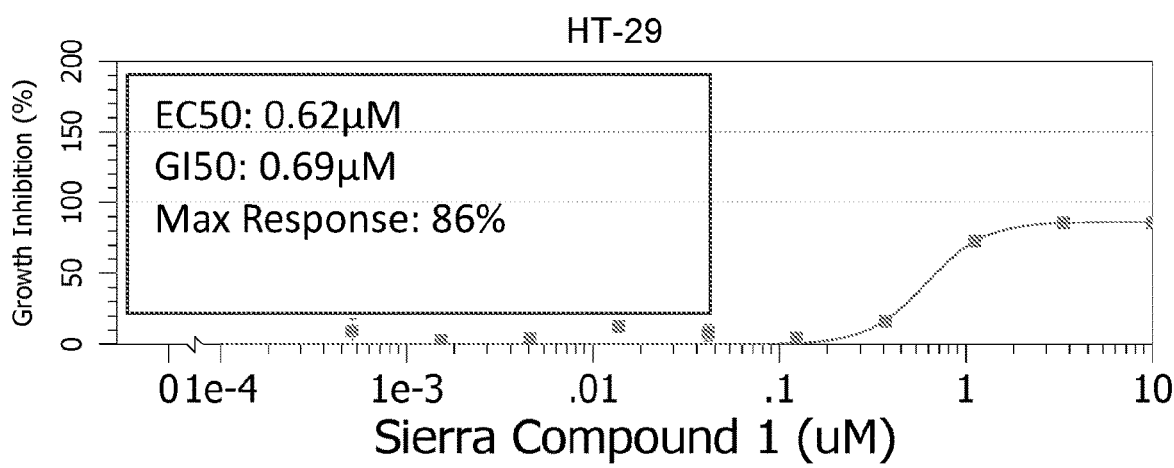
Figure 7:
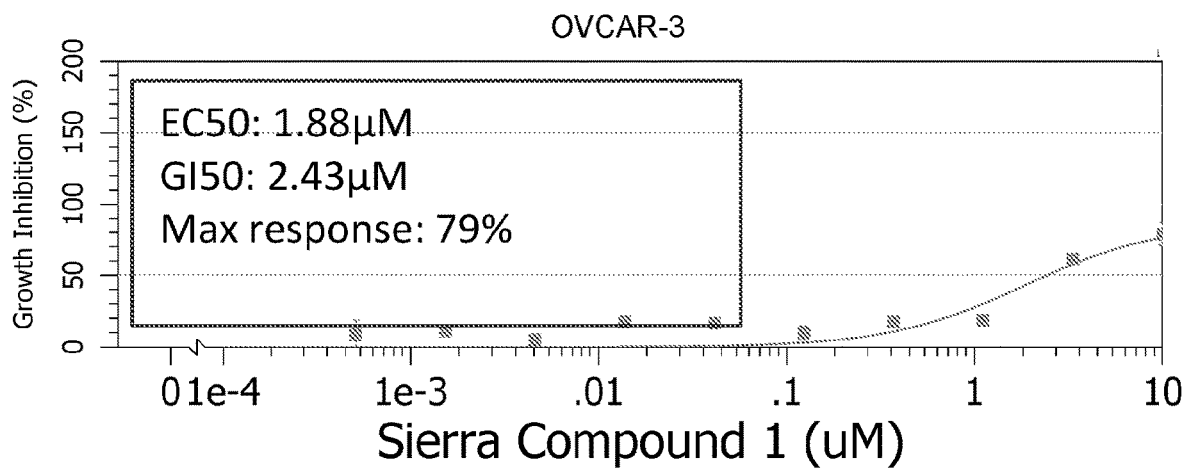

As a single agent, SRA737 demonstrated activity in 8 of the 10 cancer cell lines. SRA737 was modestly cytotoxic in the two most responsive cell lines and cytostatic in the remaining six. OVCAR-5 and SK-BR-3 cells demonstrated the highest sensitivity to SRA737. HT-29, DU145, A673 and OVCAR-3 cells demonstrated intermediate sensitivity, whereas PC-3, MDA-MB-231, BT-474 and CAL-27 cells demonstrated the least sensitivity to SRA737 (FIG. 6). The findings were consistent with a prior study for cell lines CAL-27, HT-29 and OVCAR-3 (FIG. 7).

Figure 8:
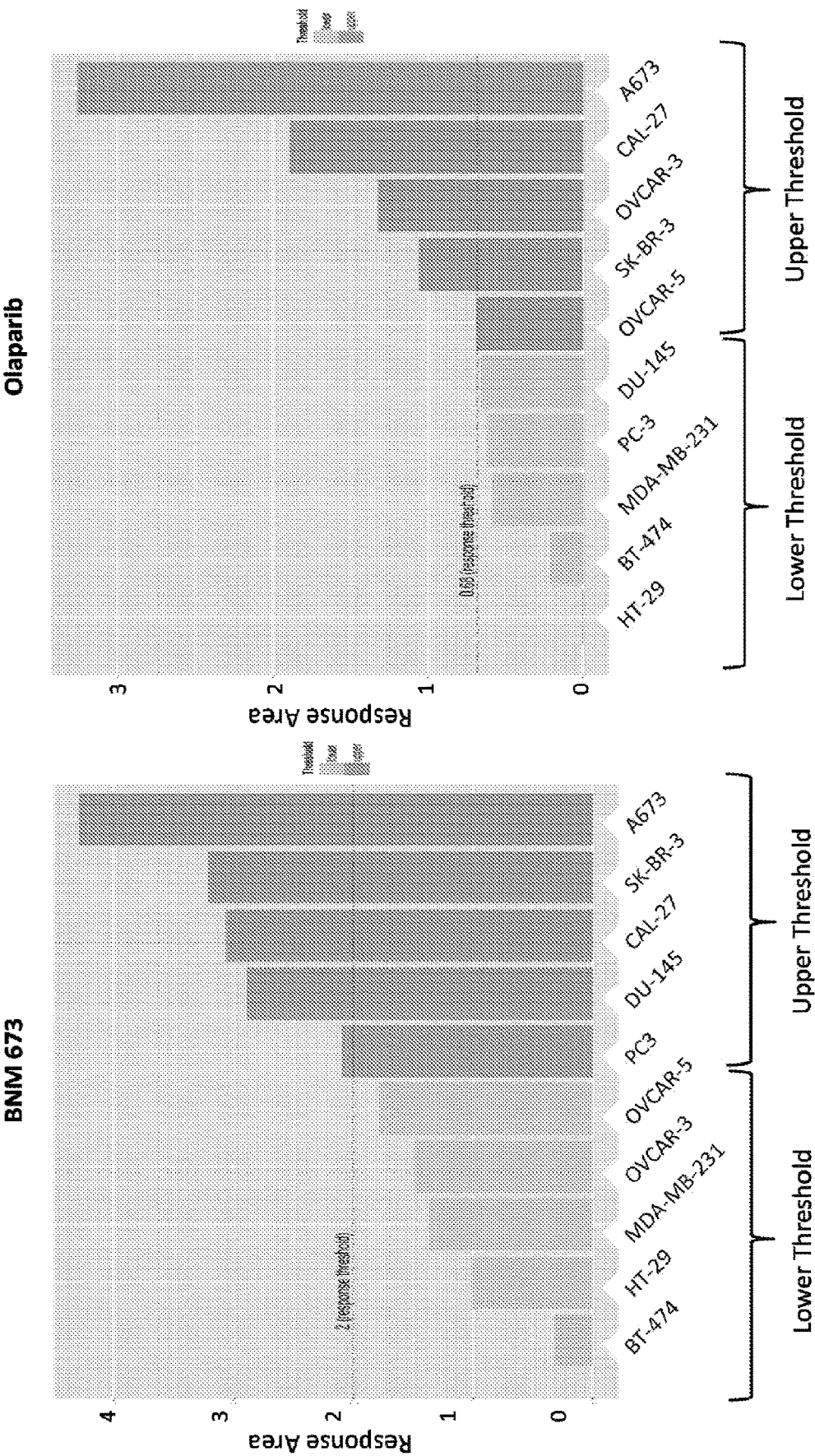
FIG. 8 shows sensitivity of the ten cell lines to each of BMN 673, Olaparib, Niraparib and Rucaparib.
Figure 8:
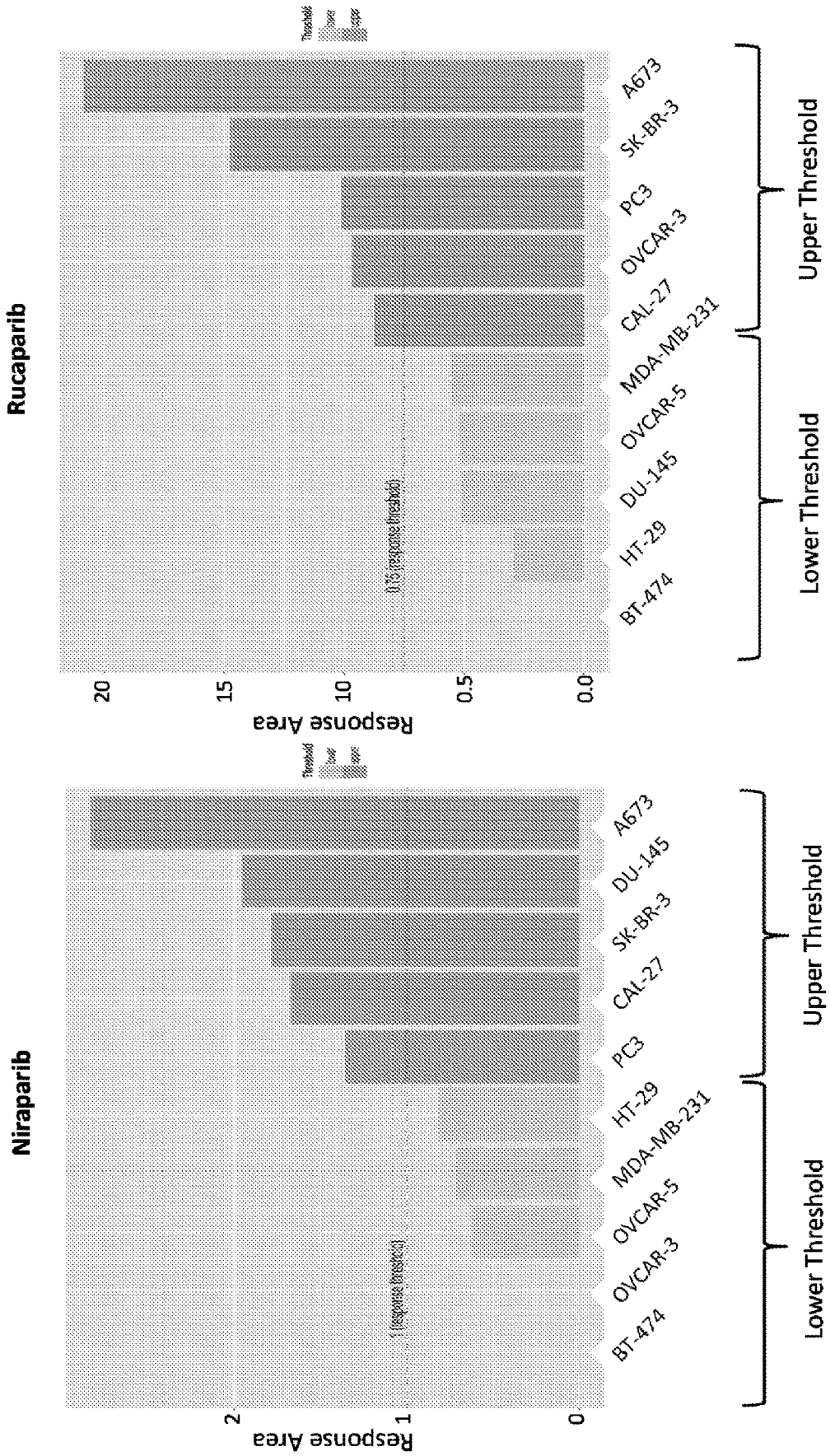
Figure 9:
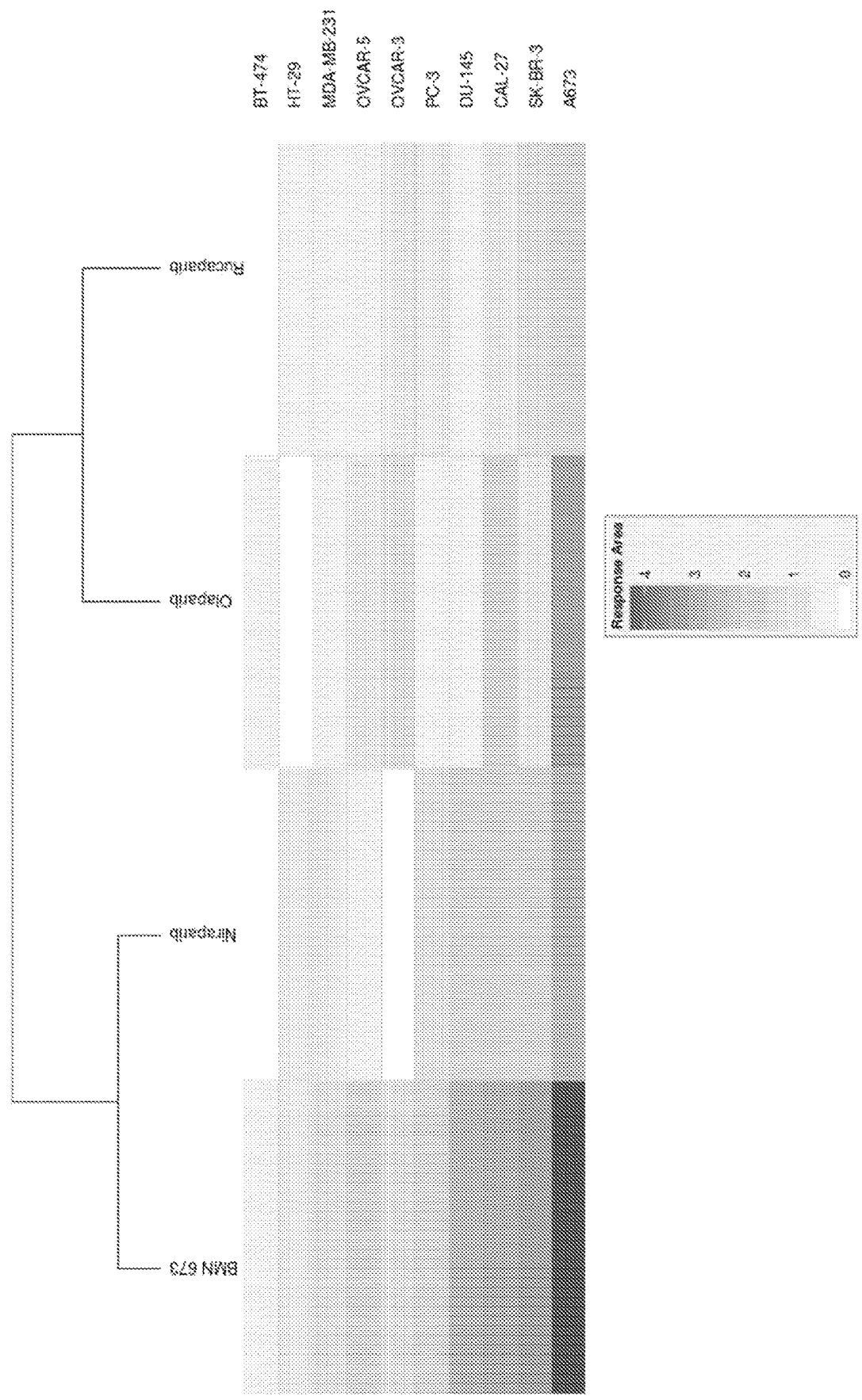
FIG. 9 illustrates results of cluster analysis of sensitively of the ten cell lines to each of BMN 673, Olaparib, Niraparib and Rucaparib. Overall sensitivity of the cell line panel to PARP inhibition was also analysed using a proprietary Heat Map tool. Response area (AUC) was used as a measure that captures both potency and efficacy. Cell lines were ranked based on the average response area across the 4 inhibitors
Figure 11:
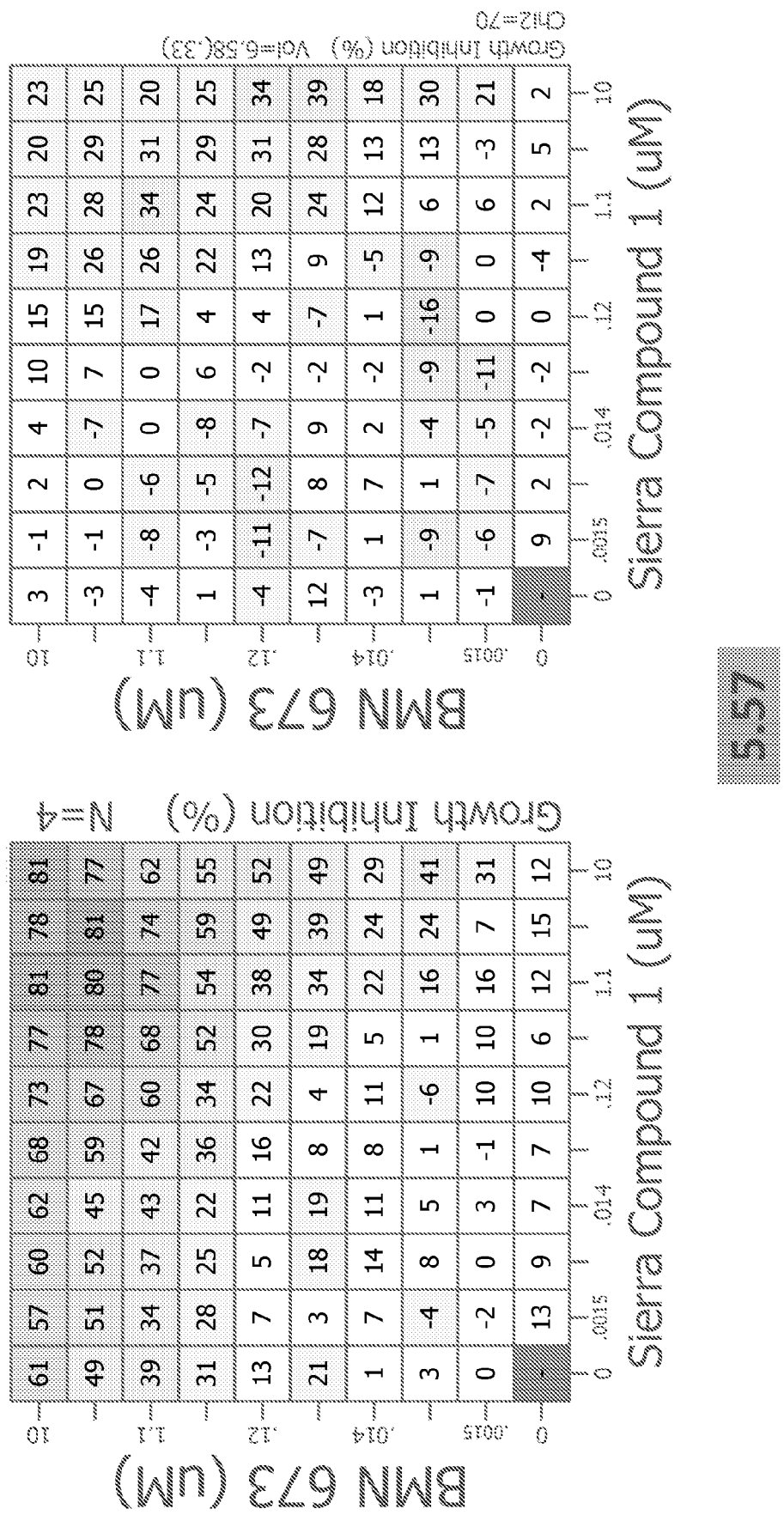
FIG. 11 shows combination activity of Sierra Compound 1 (SRA737) and BMN 673 in PC-3 cells, HT-29 cells, DU-145 cells and CAL-27 cells.
Figure 11:
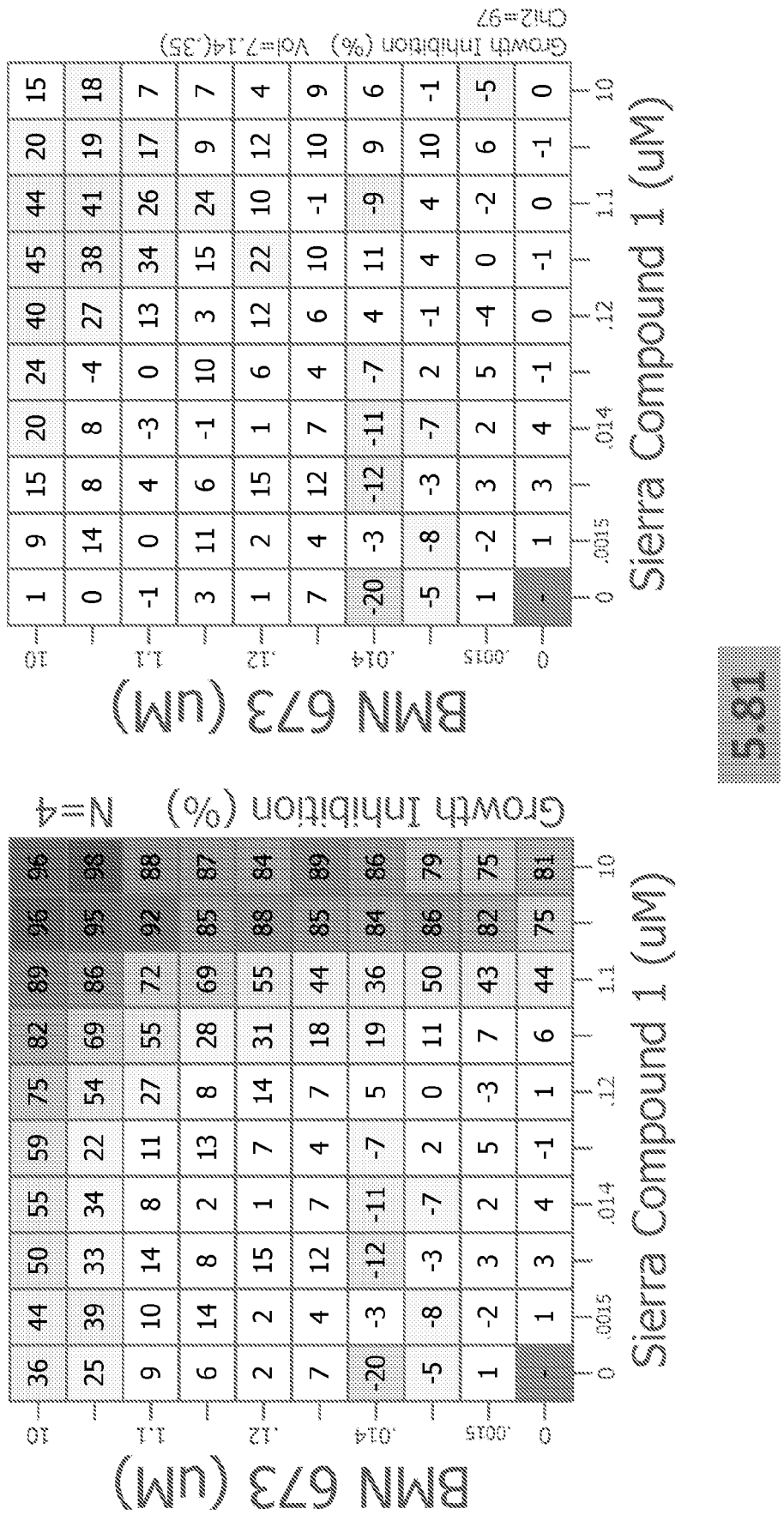
Figure 11:
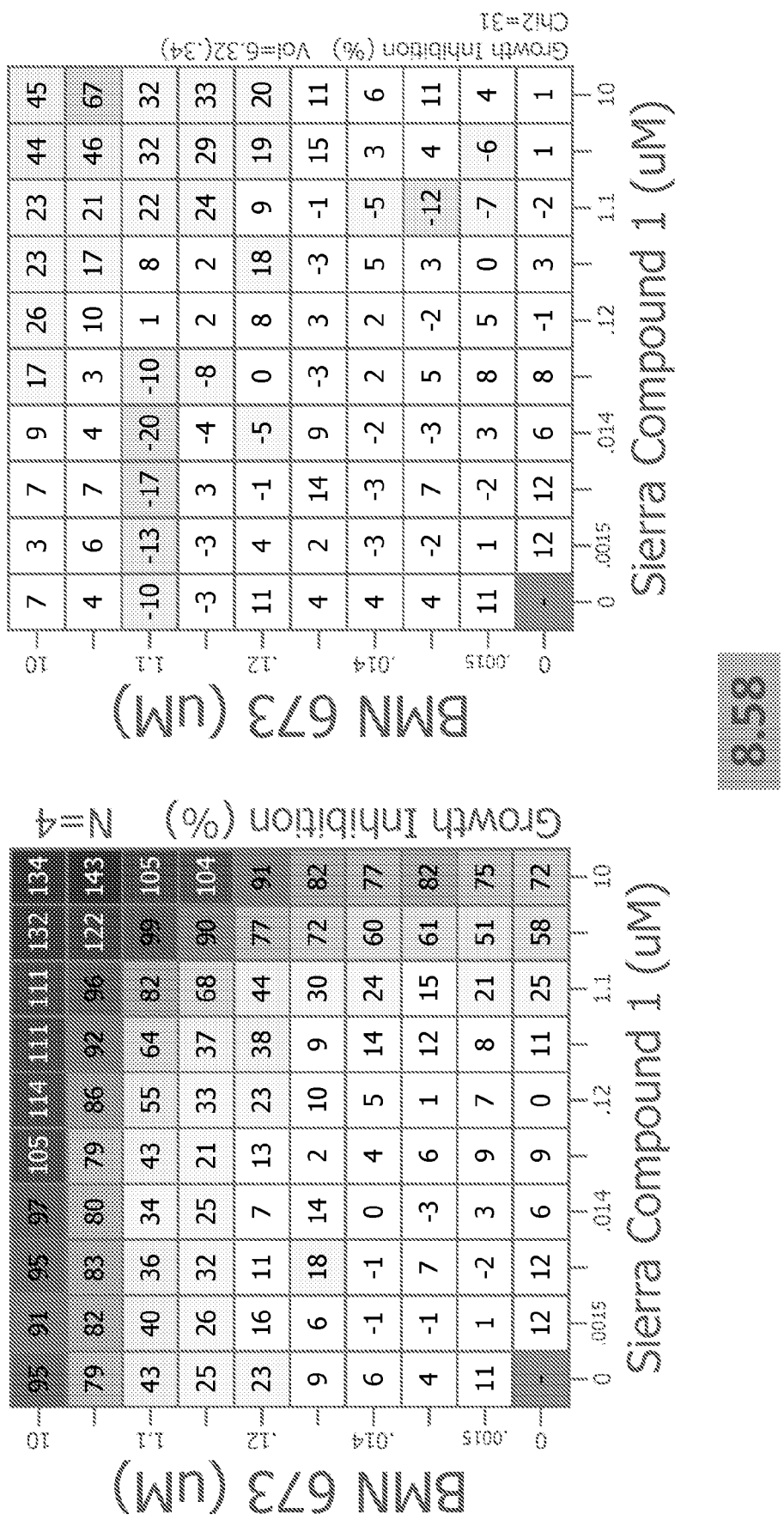
Figure 11:
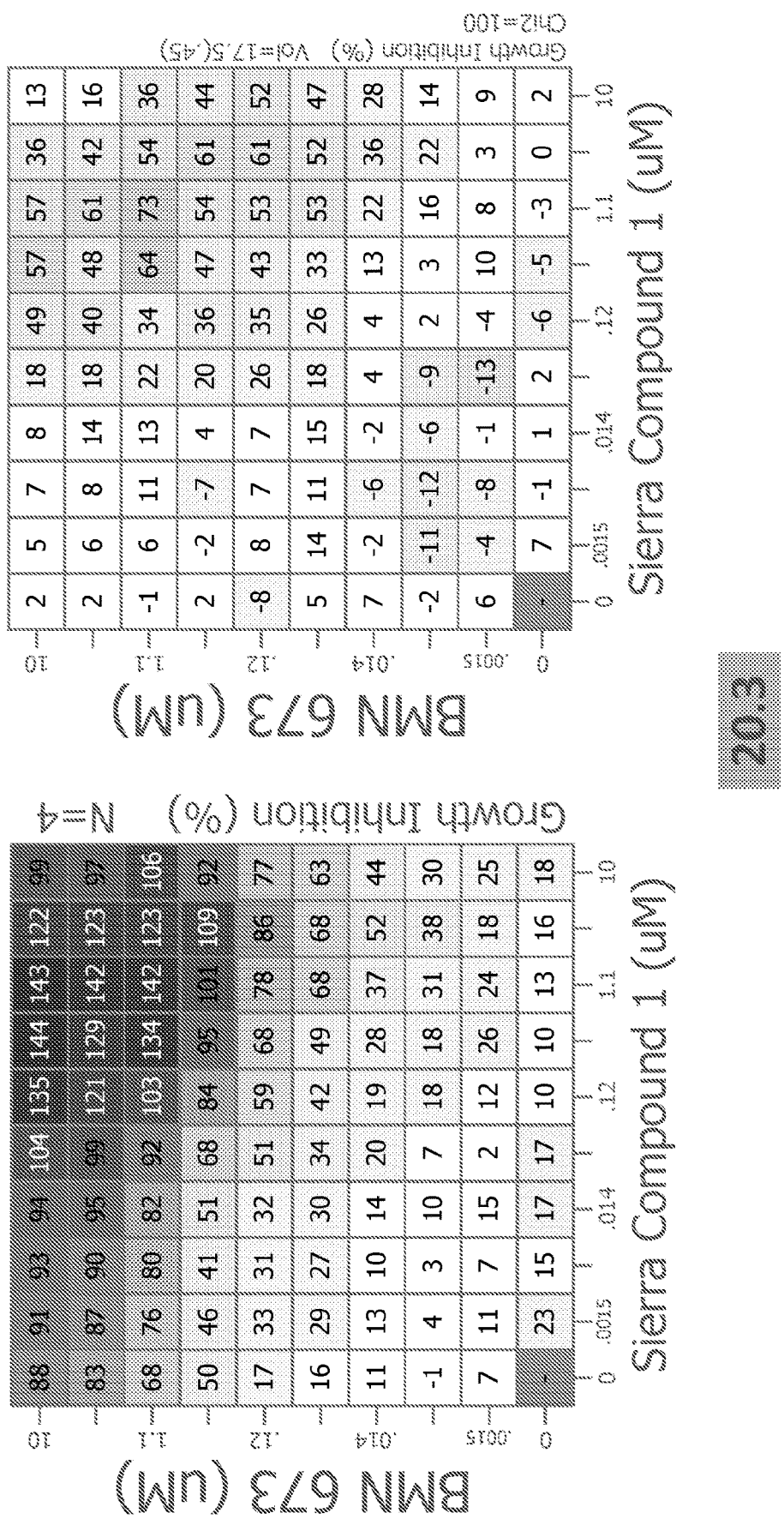
Figure 12:
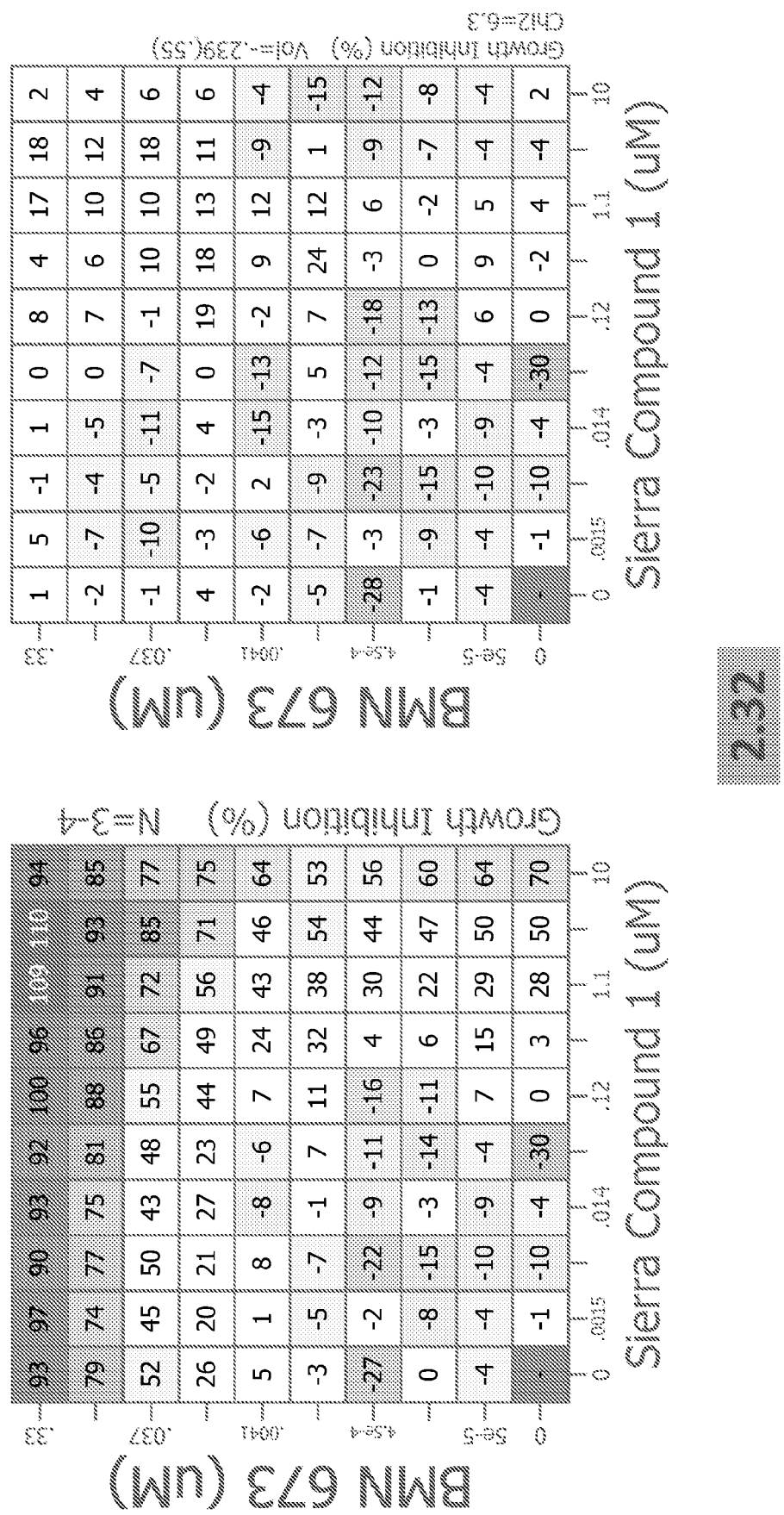
FIG. 12 shows combination activity of Sierra Compound 1 (SRA737) and BMN 673 in A673 cells, MDA-MB-231 cells, BT474 cells, and SK-BR-3 cells.
Figure 12:
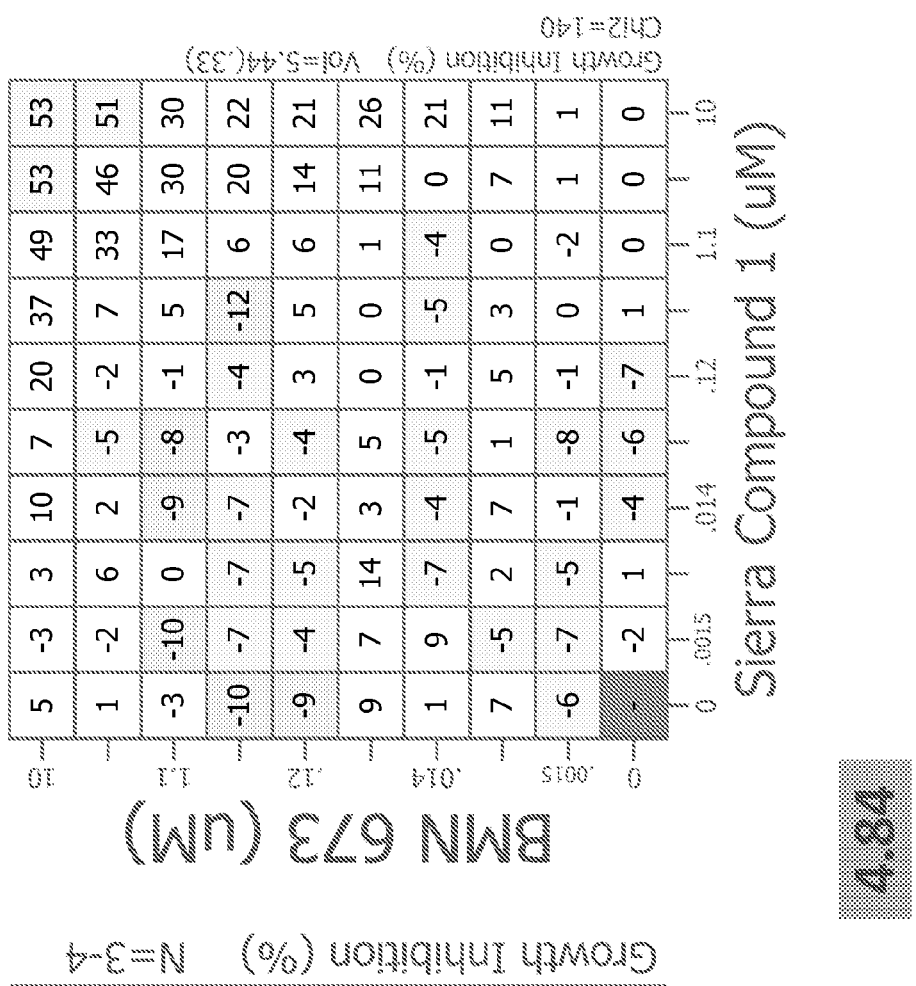
Figure 12:
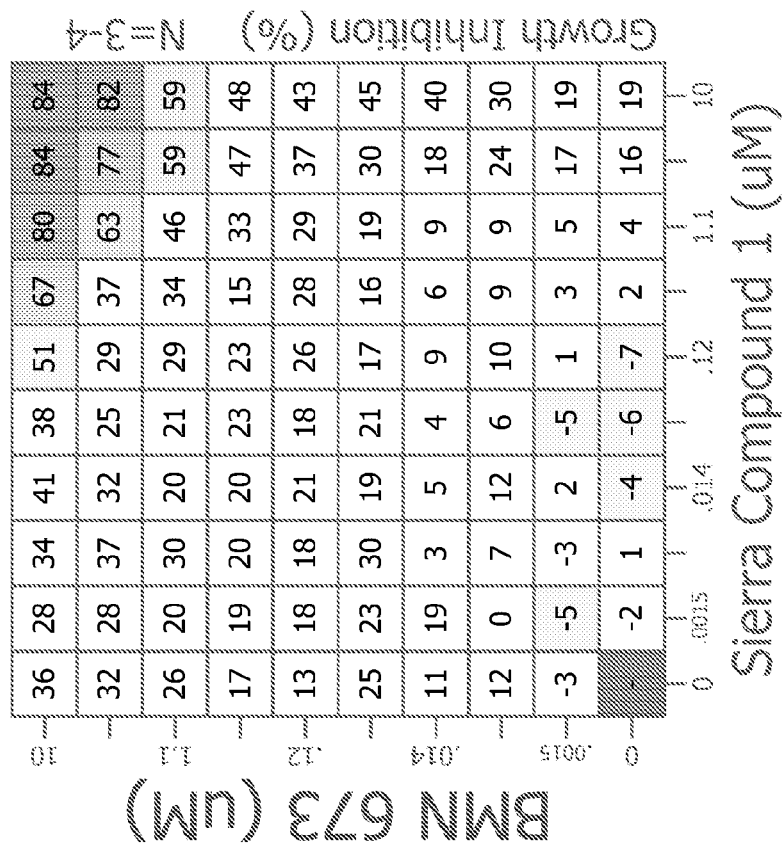
Figure 12:
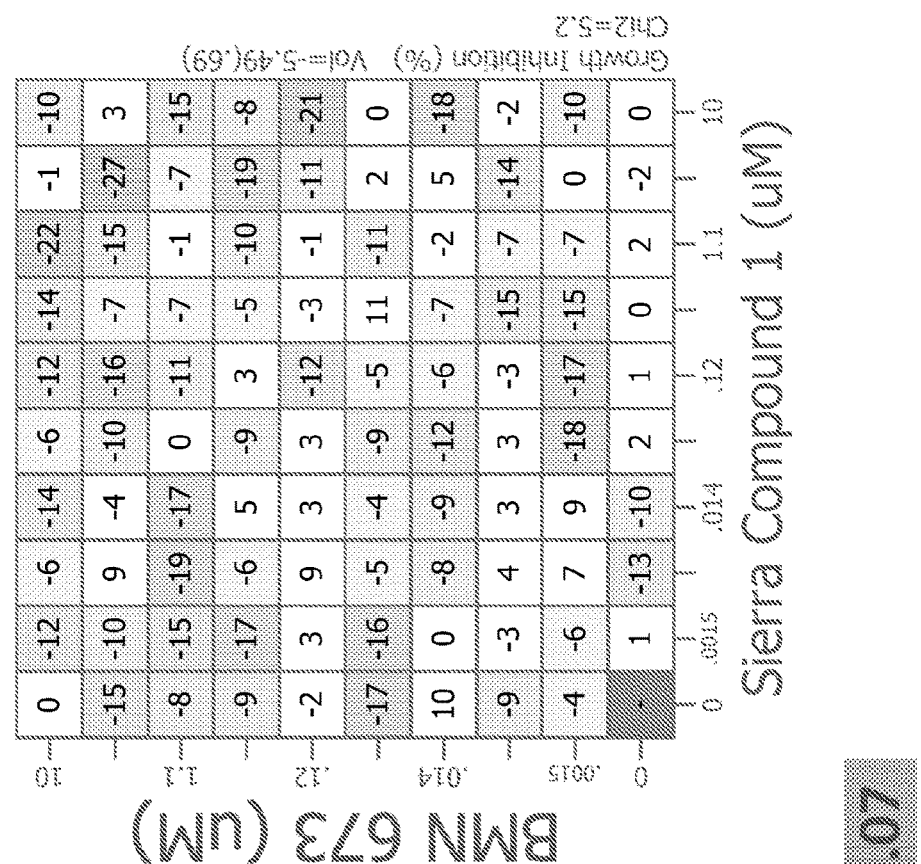
Figure 12:
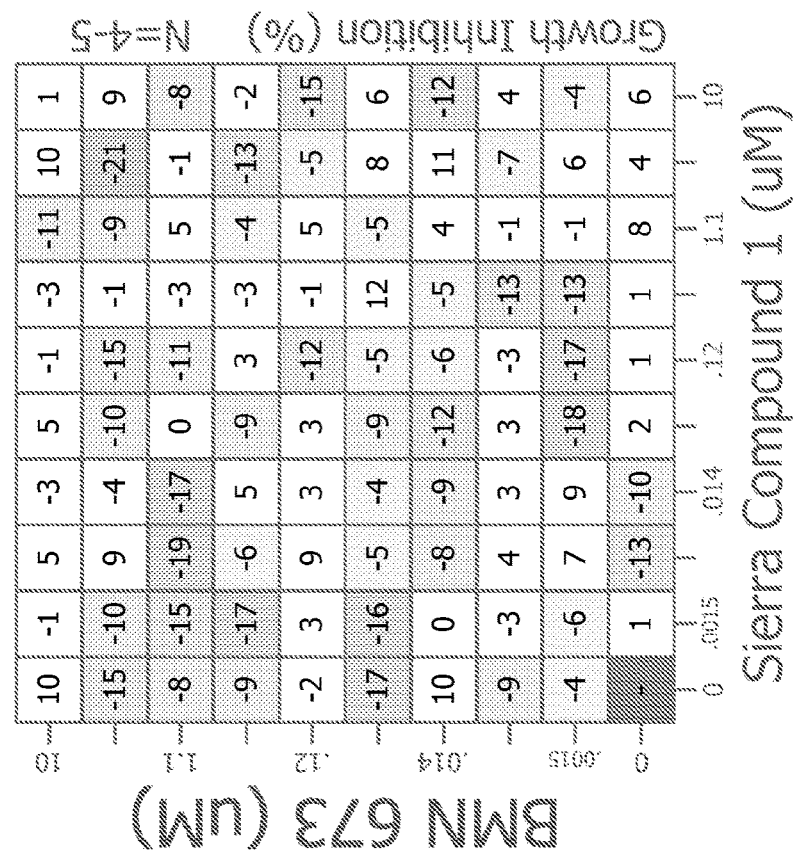
Figure 12:
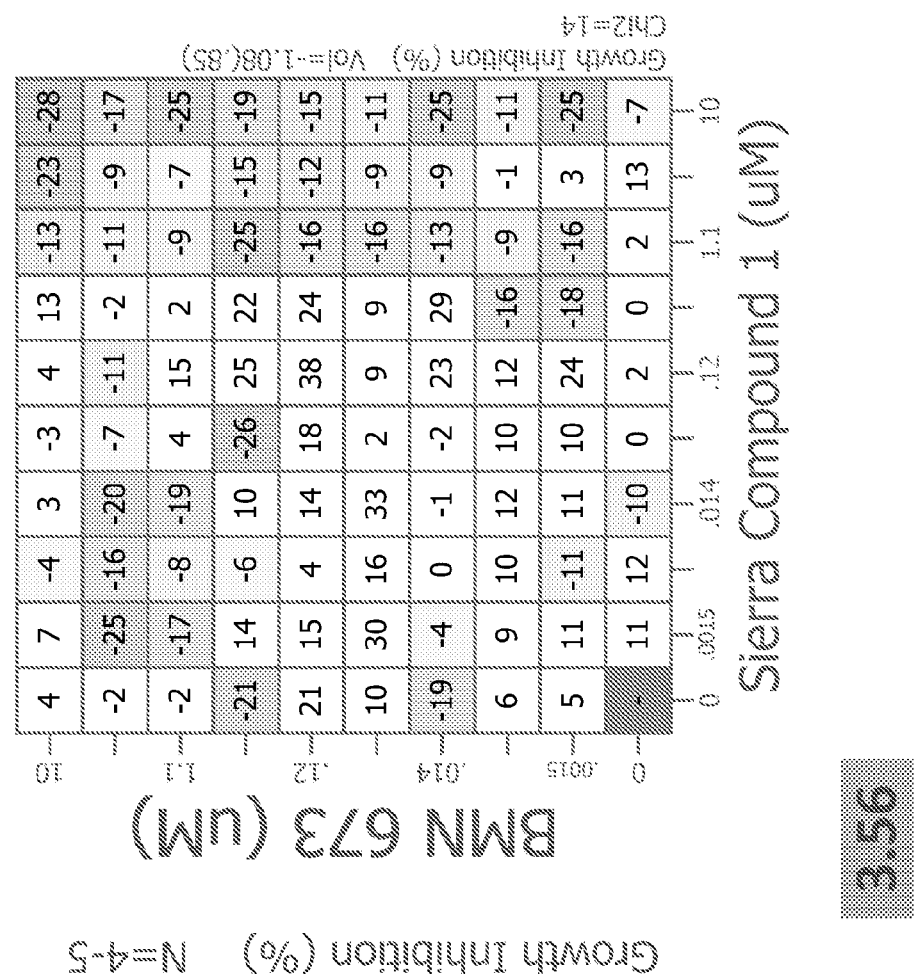
Figure 13:
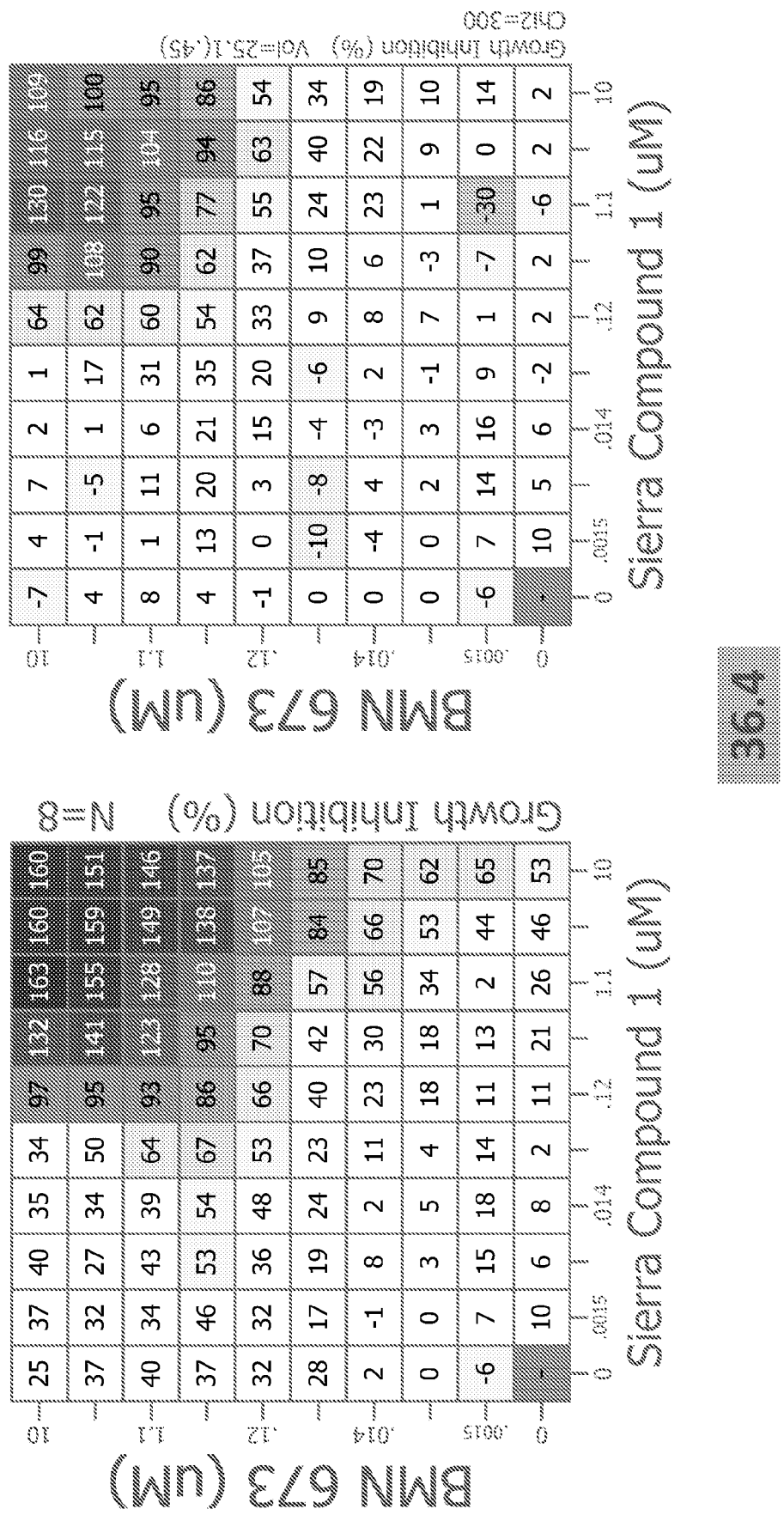
FIG. 13 shows combination activity of Sierra Compound 1 (SRA737) and BMN 673 in OVCAR-3 cells and OVCAR-5 cells.
Figure 13:
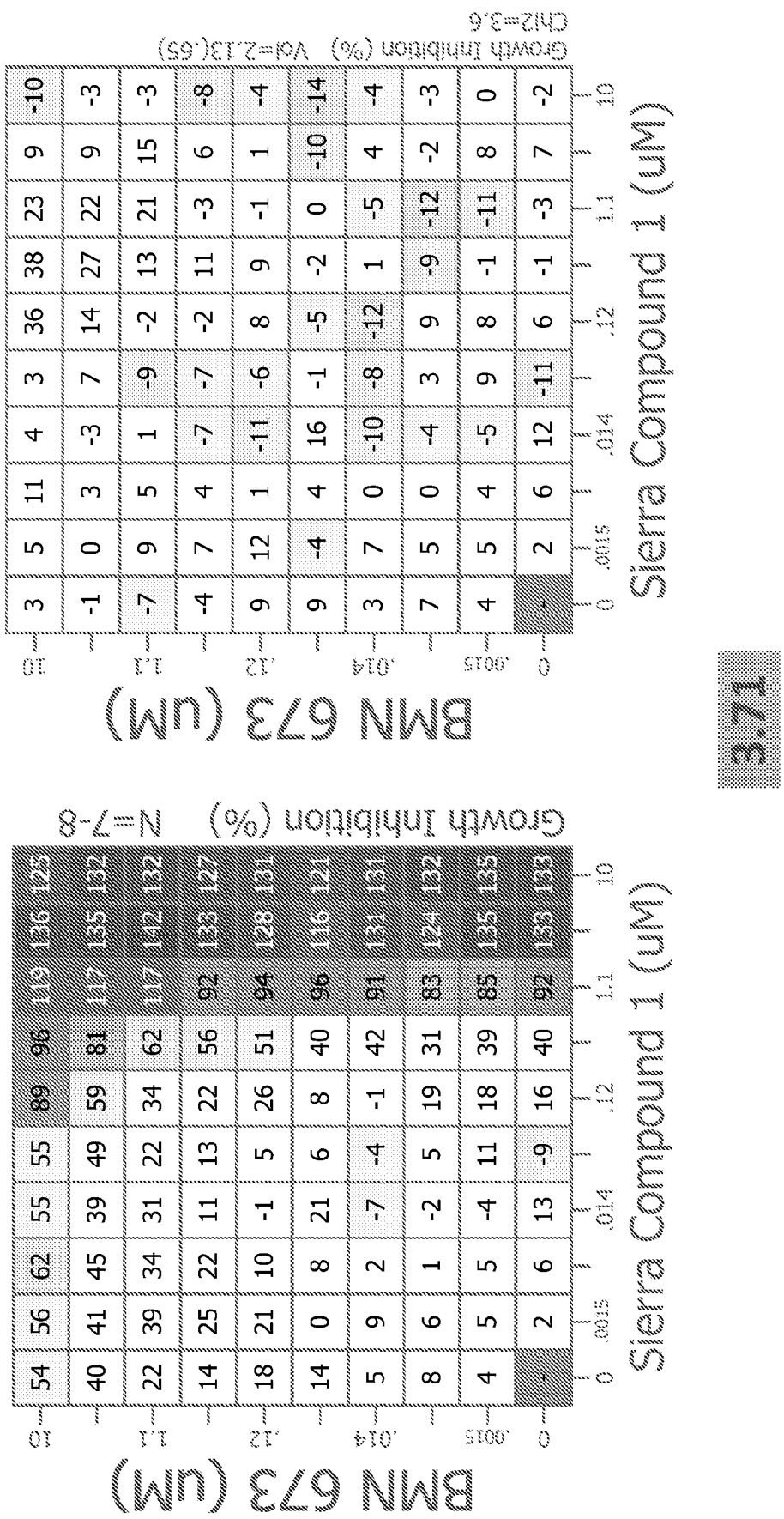
Figure 14:
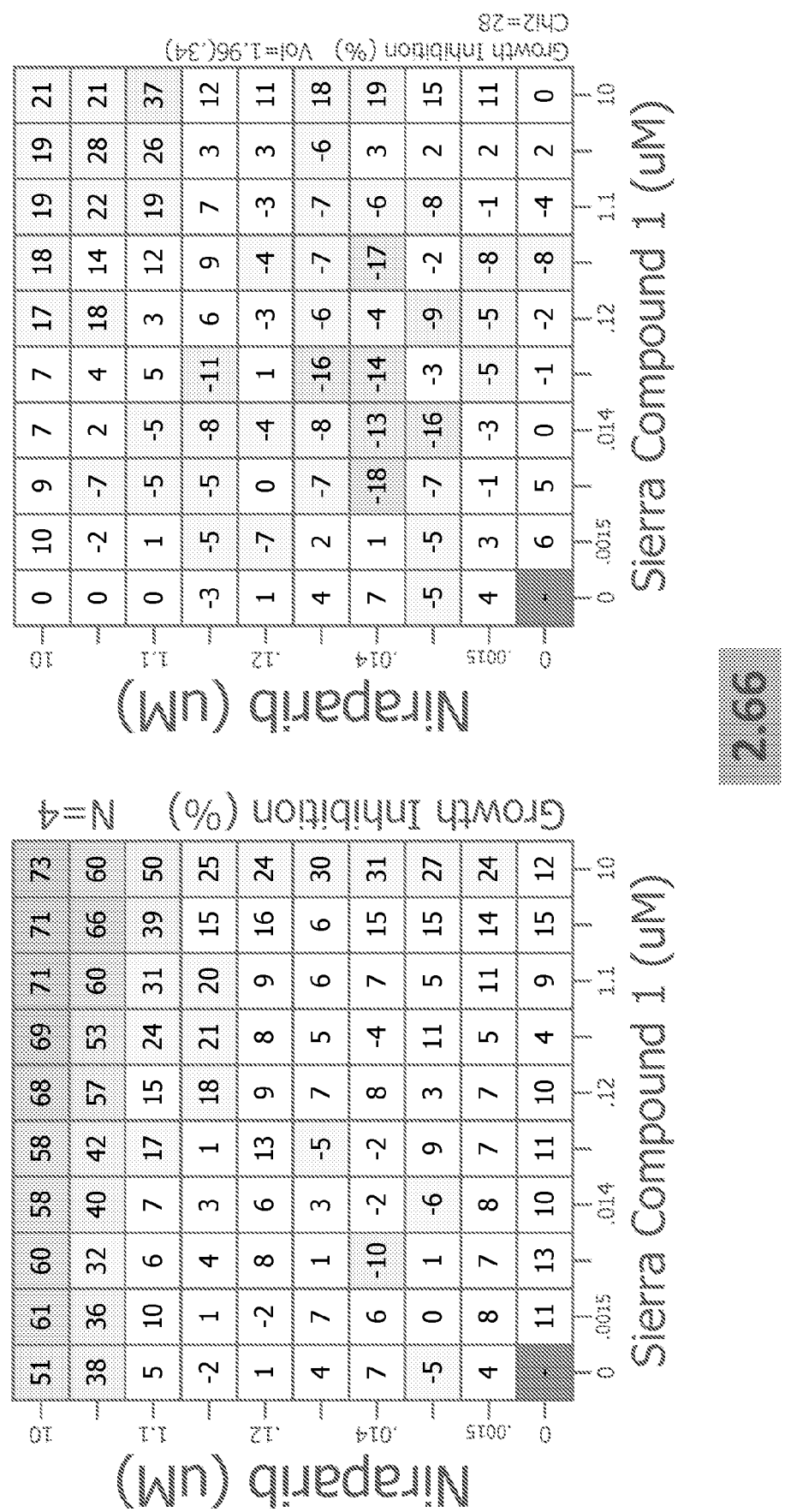
FIG. 14 shows combination activity of Sierra Compound 1 (SRA737) and Niraparib in PC-3 cells, HT-29 cells, DU-145 cells and CAL-27 cells.
Figure 14:
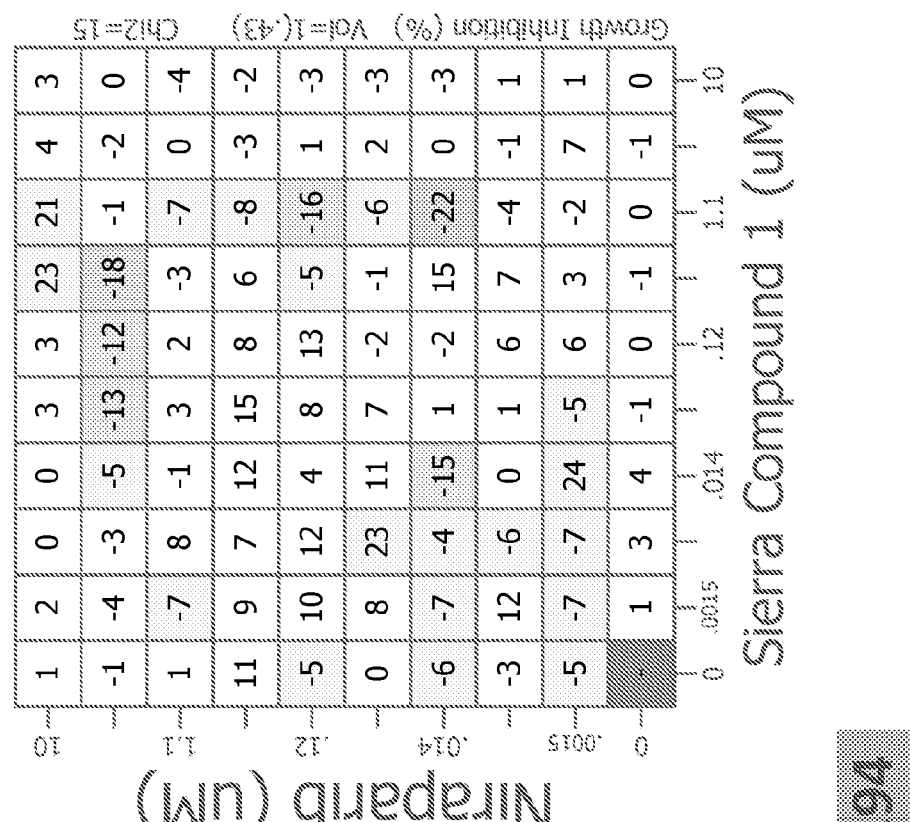
Figure 14:
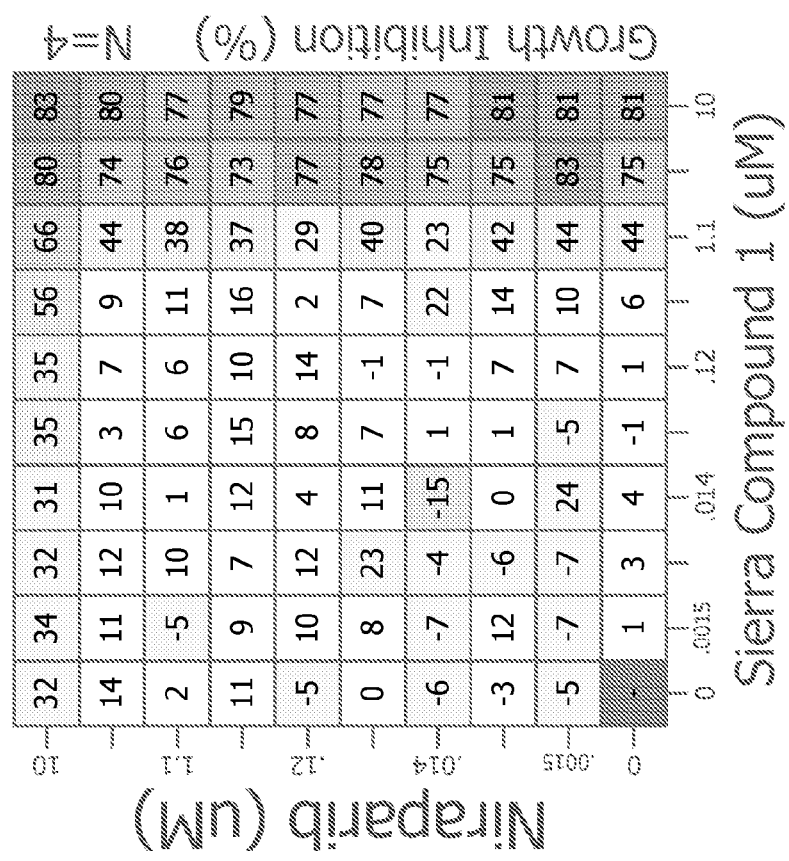
Figure 14:
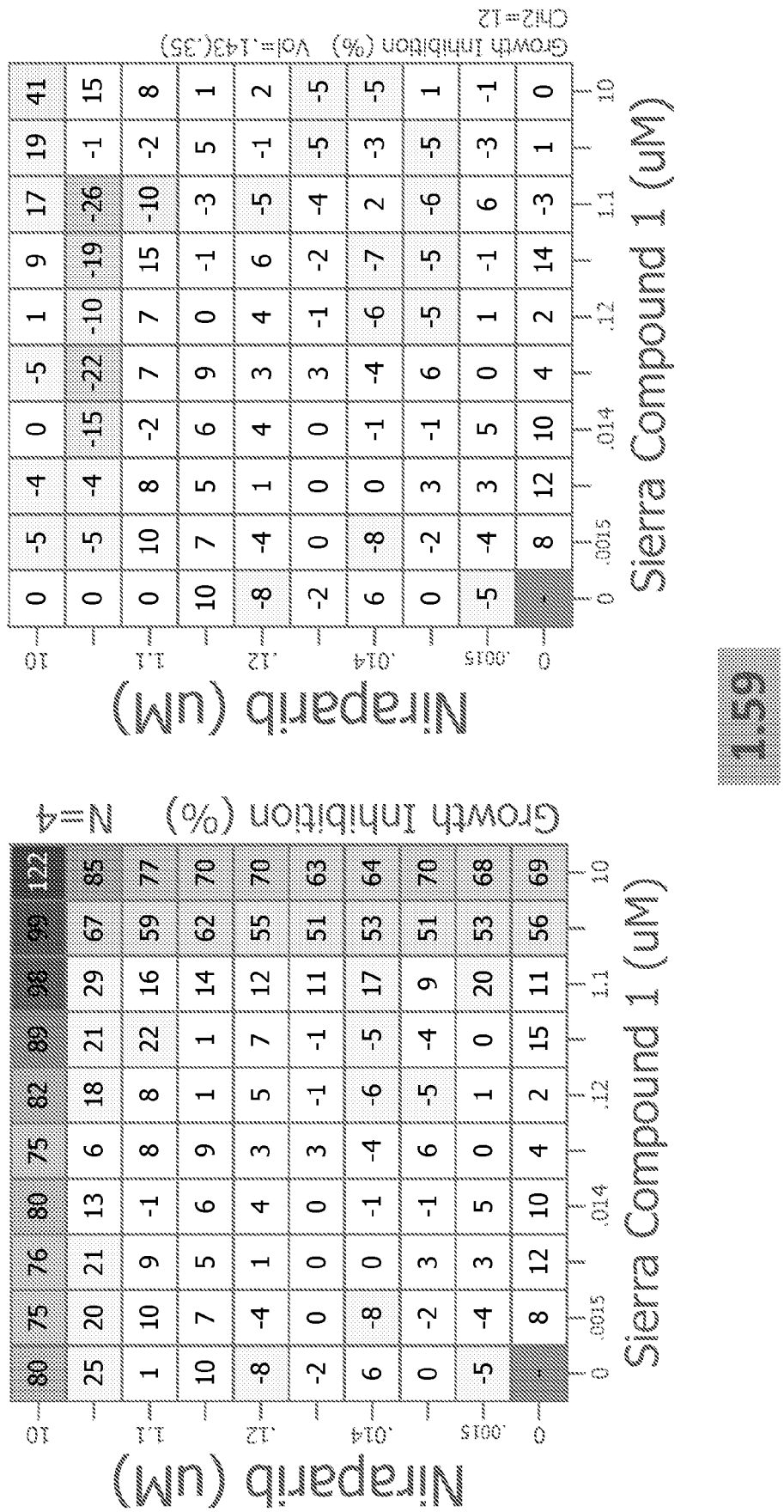
Figure 14:
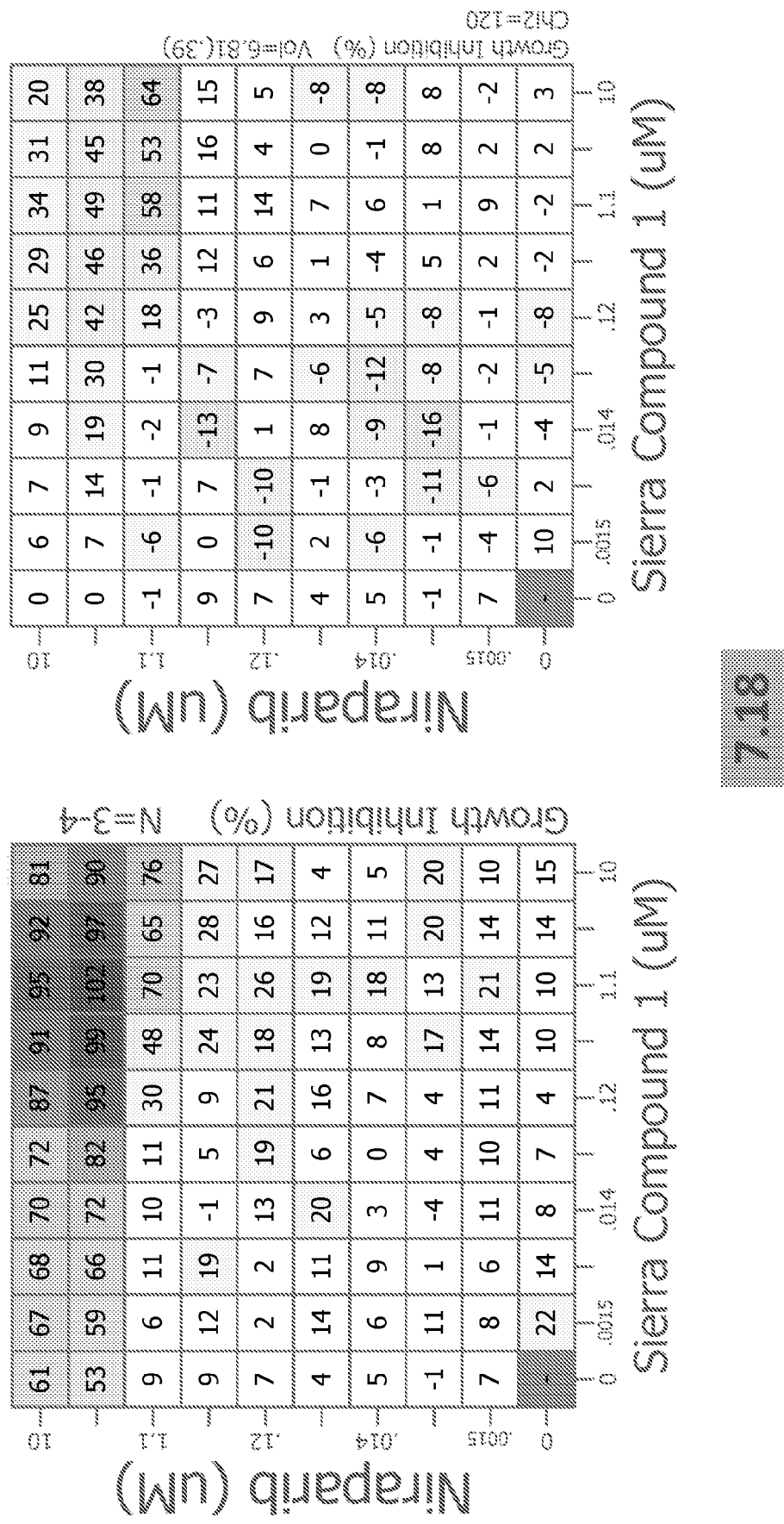
Figure 15:
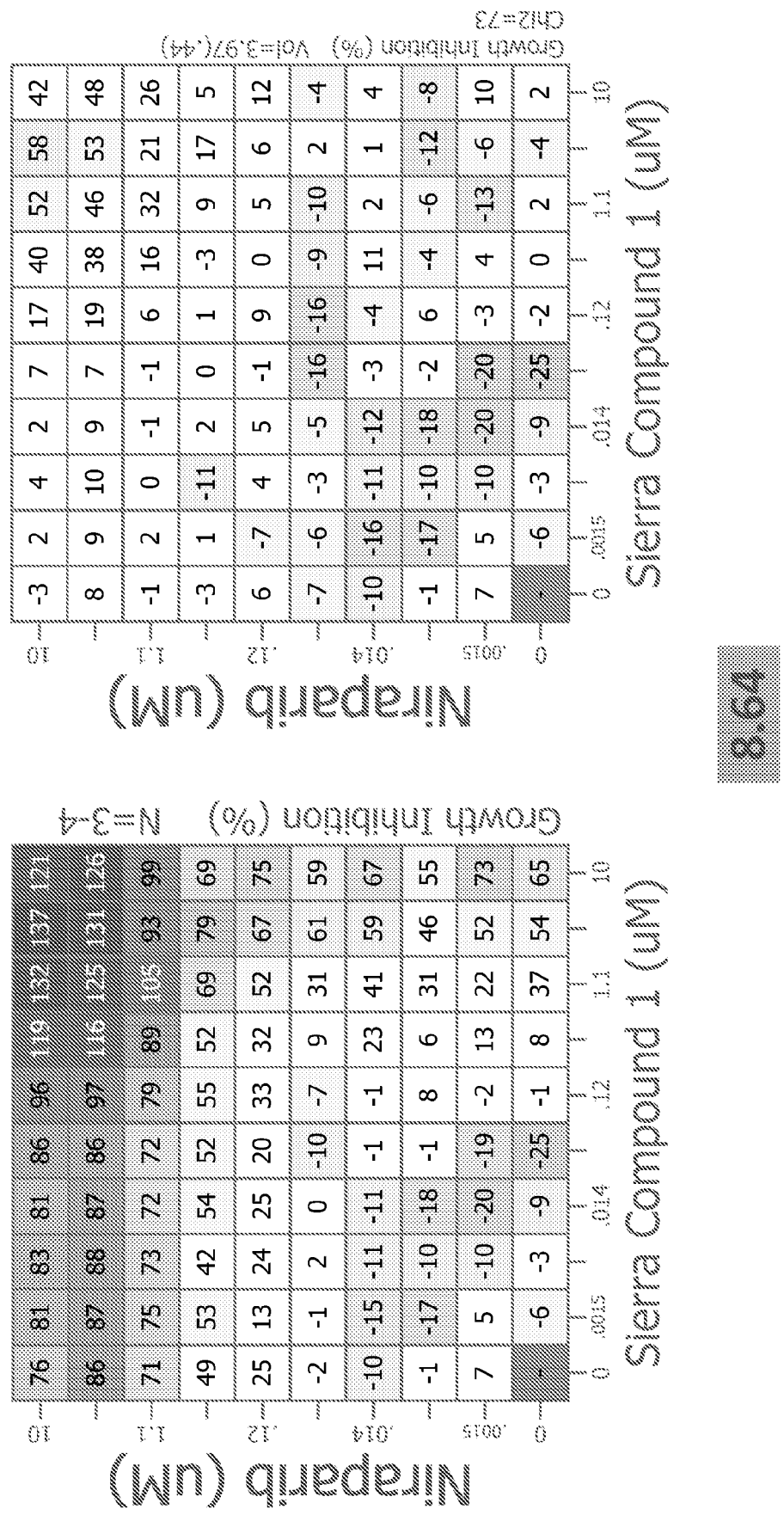
FIG. 15 shows combination activity of Sierra Compound 1 (SRA737) and Niraparib in A673 cells, MDA-MB-231 cells, BT474 cells, and SK-BR-3 cells.
Figure 15:
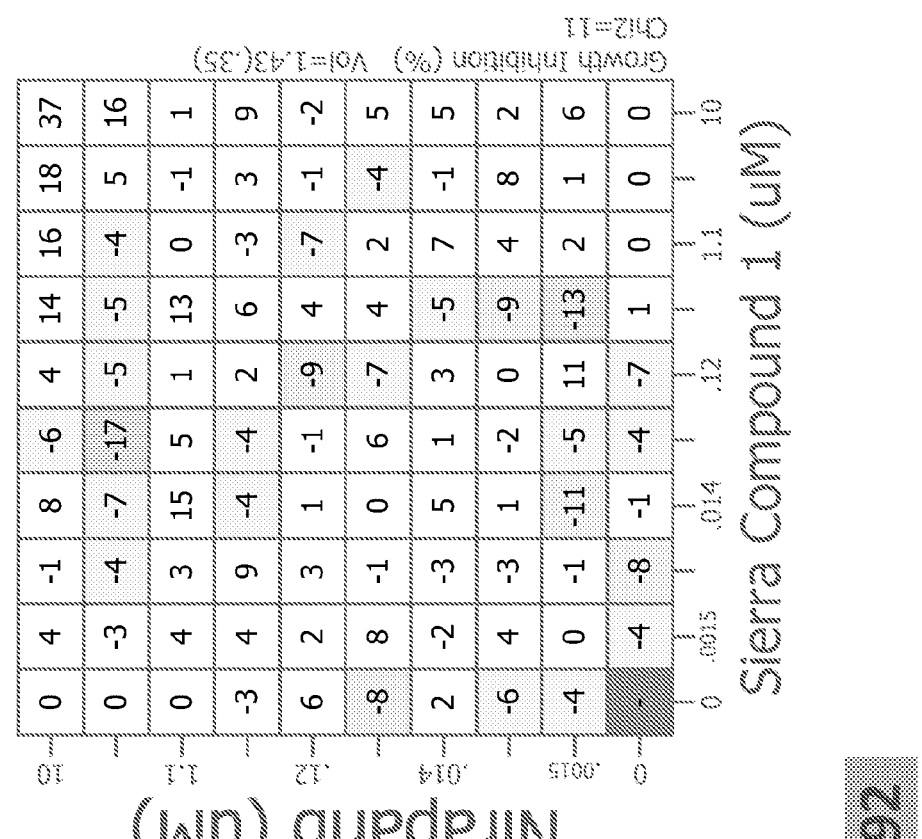
Figure 15:
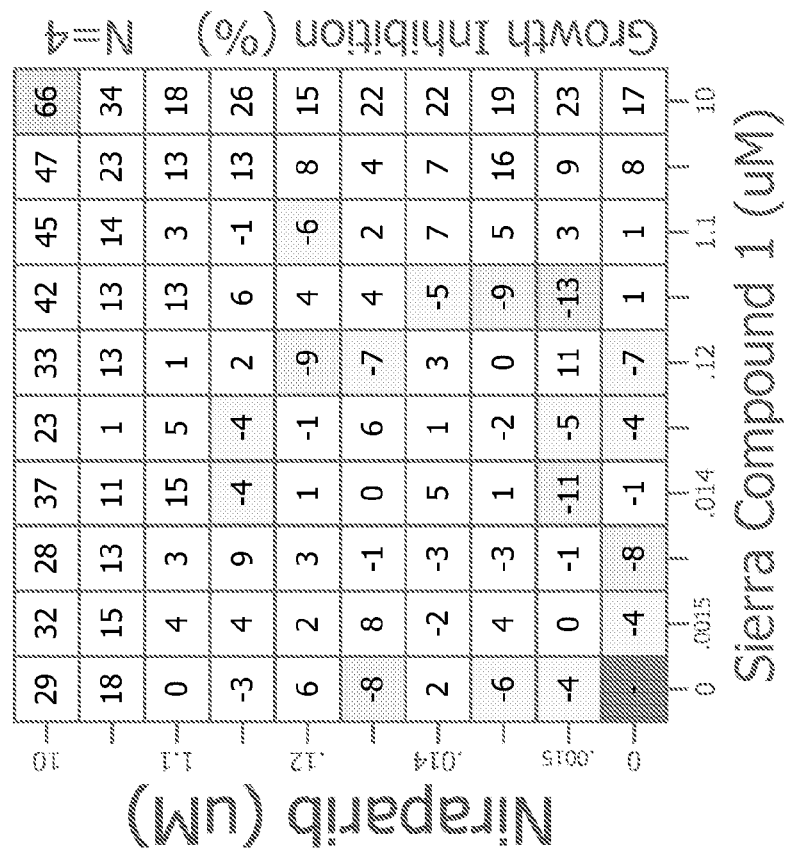
Figure 15:
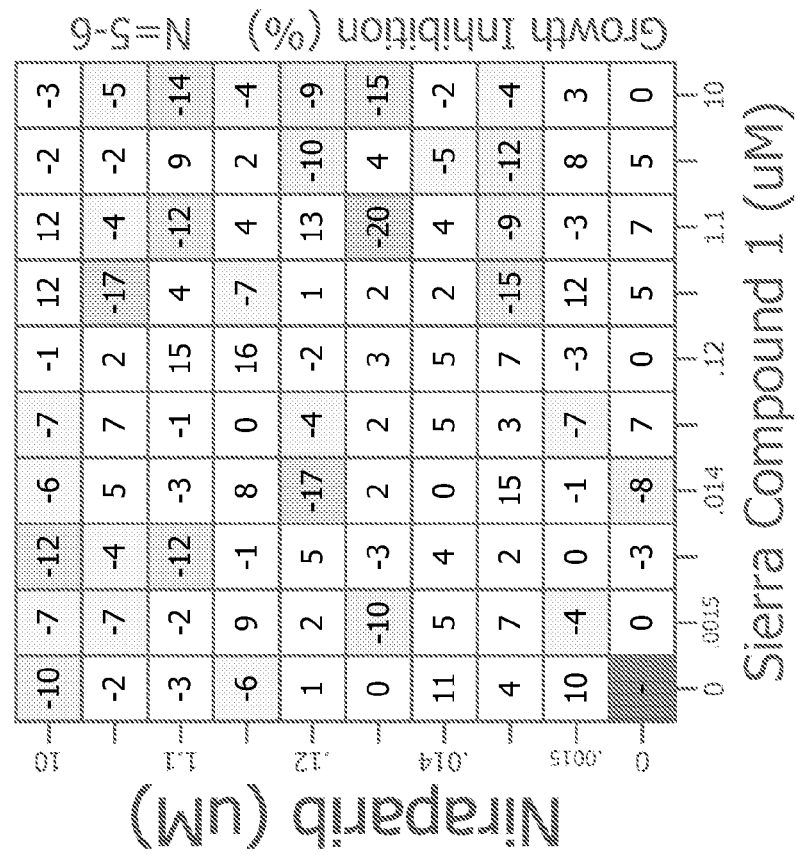
Figure 15:
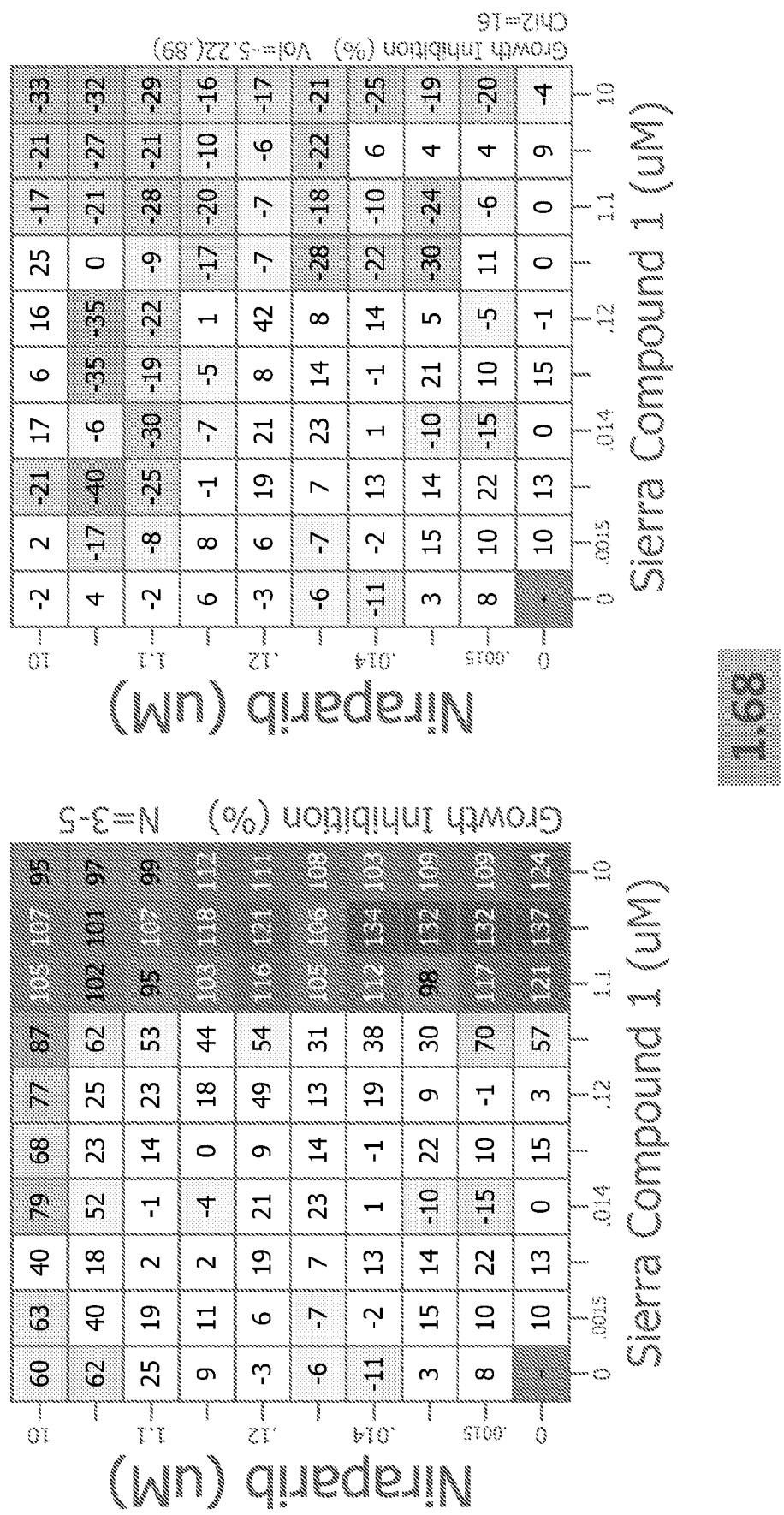
Figure 16:
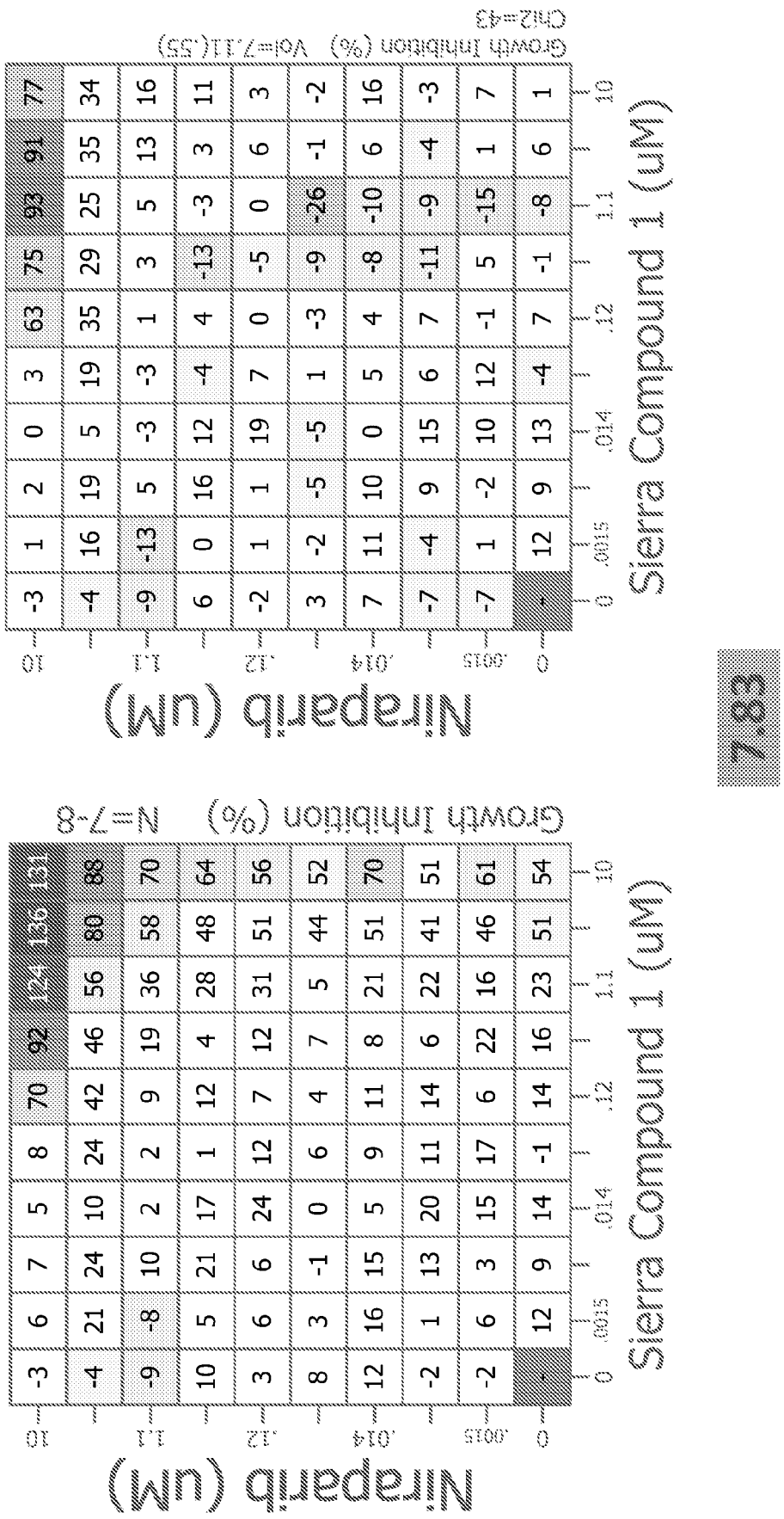
FIG. 16 shows combination activity of Sierra Compound 1 (SRA737) and Niraparib in OVCAR-3 cells and OVCAR-5 cells.
Figure 16:
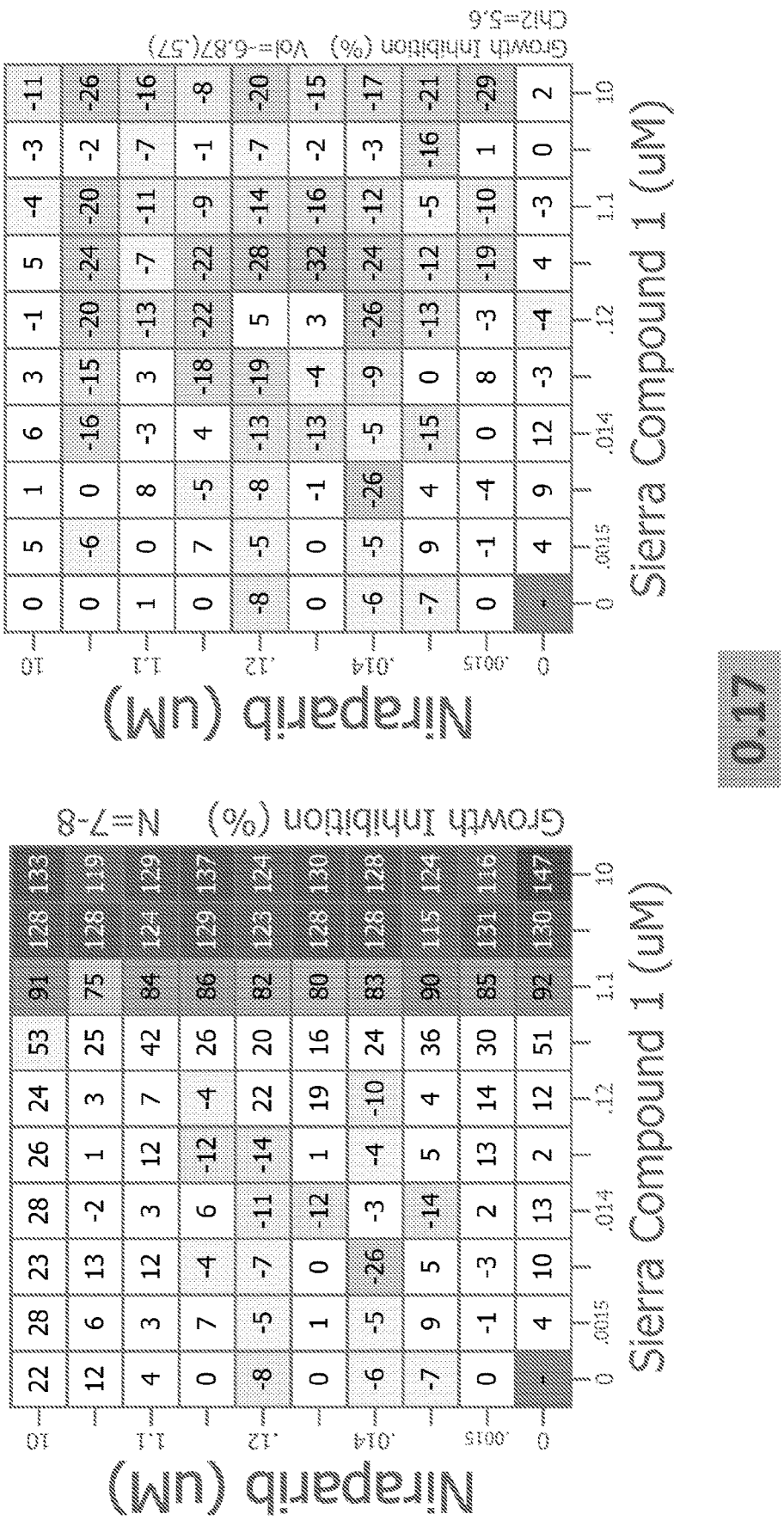
Figure 17:
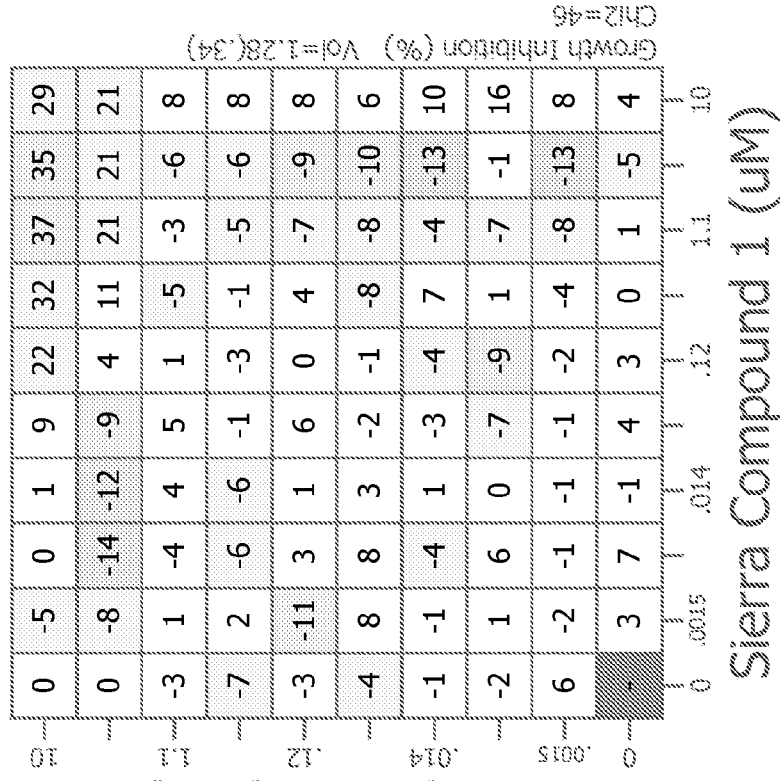
FIG. 17 shows combination activity of Sierra Compound 1 (SRA737) and Olaparib in PC-3 cells, HT-29 cells, DU-145 cells and CAL-27 cells.
Figure 17:
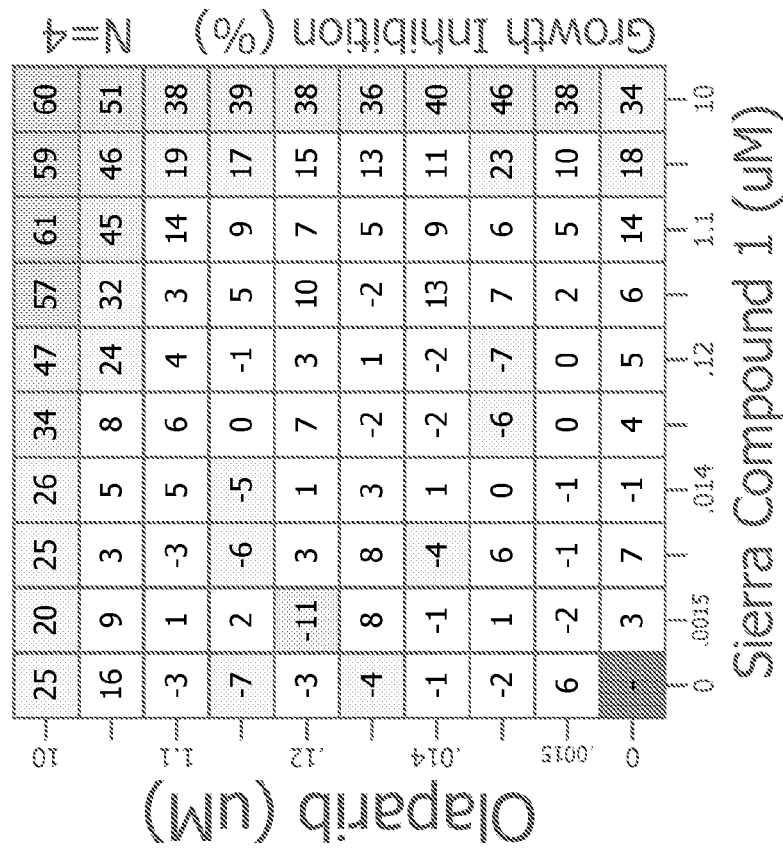
Figure 17:
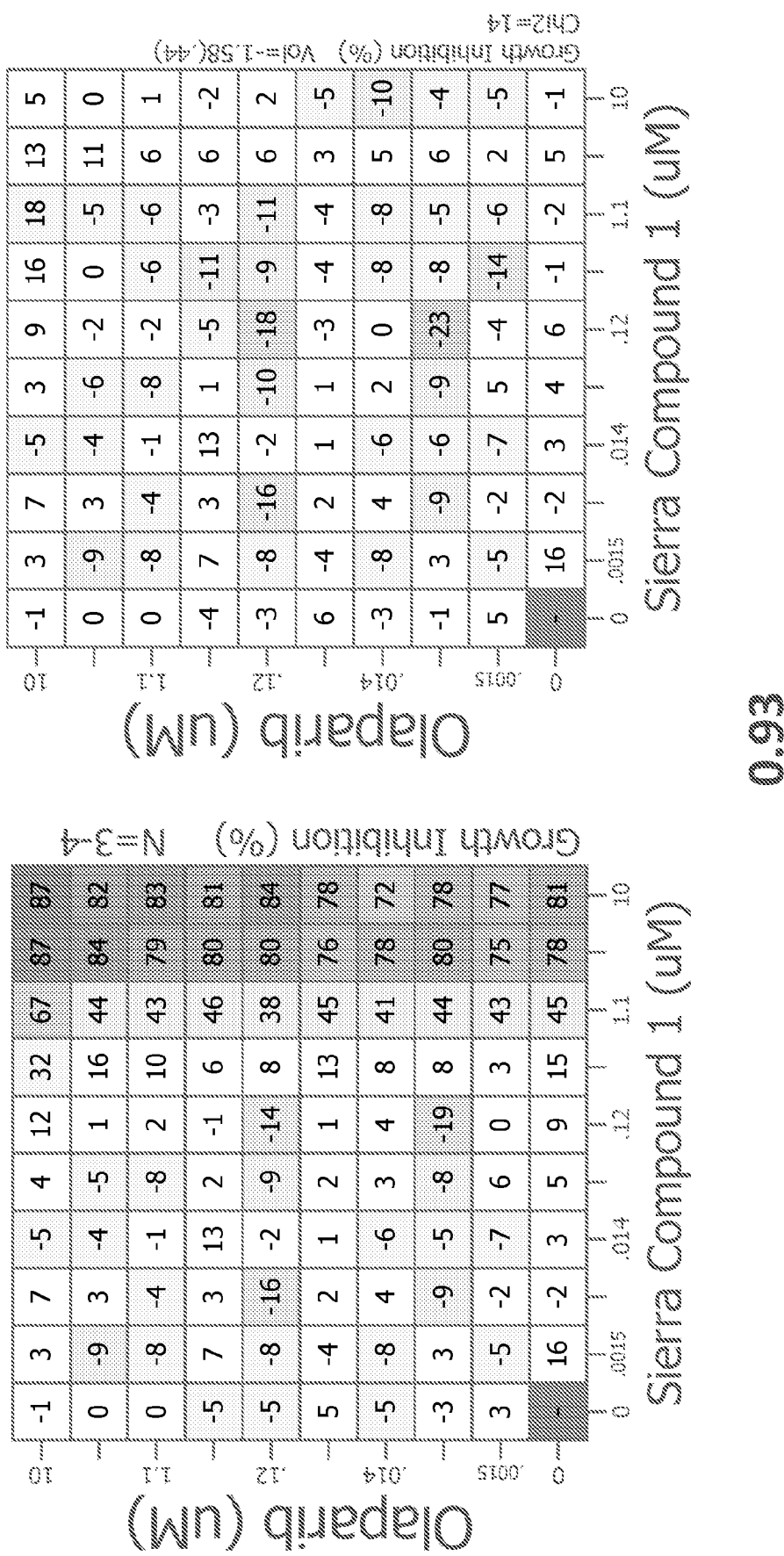
Figure 17:
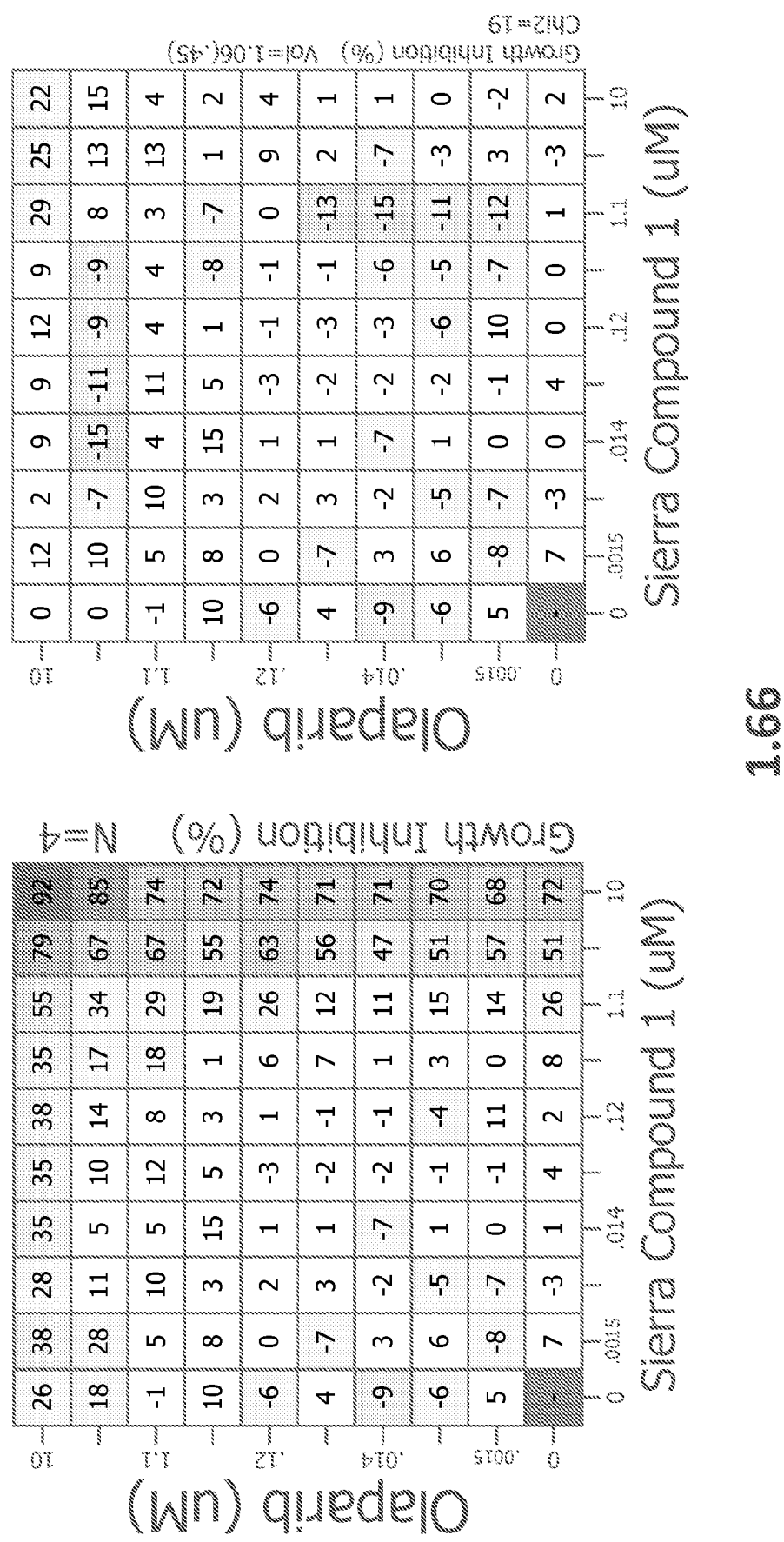
Figure 17:
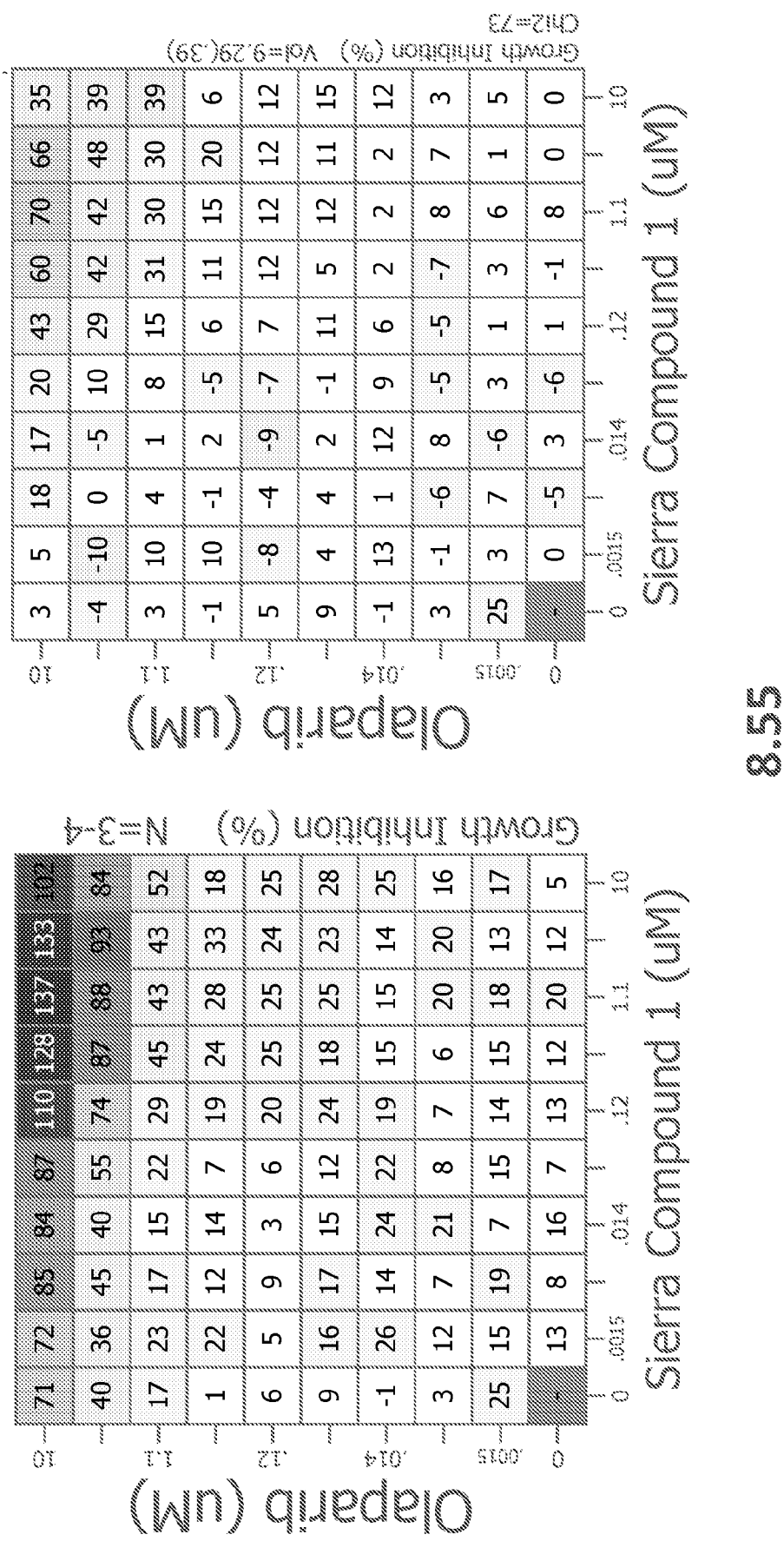
Figure 18:
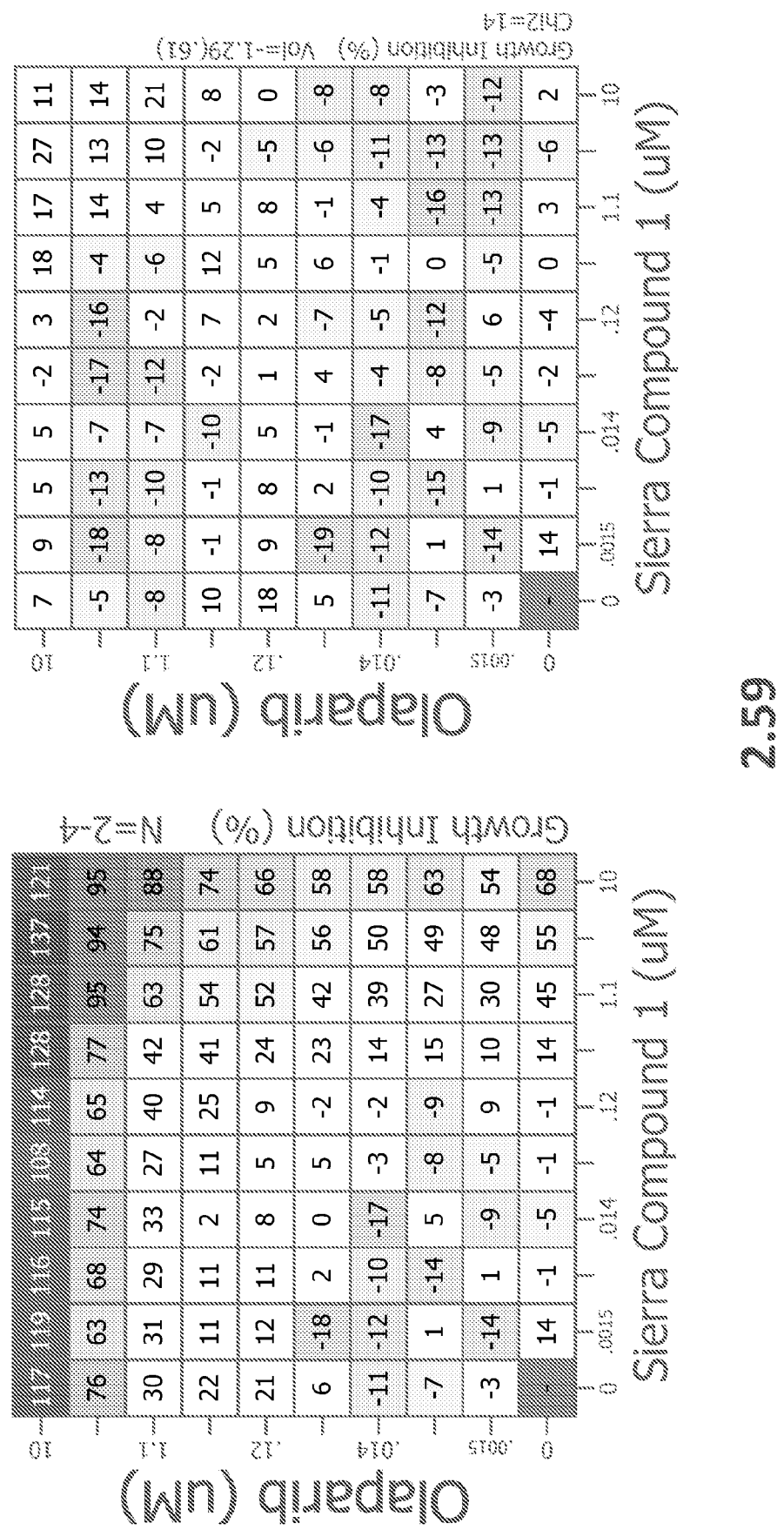
FIG. 18 shows combination activity of Sierra Compound 1 (SRA737) and Olaparib in A673 cells, MDA-MB-231 cells, BT474 cells, and SK-BR-3 cells.
Figure 18:
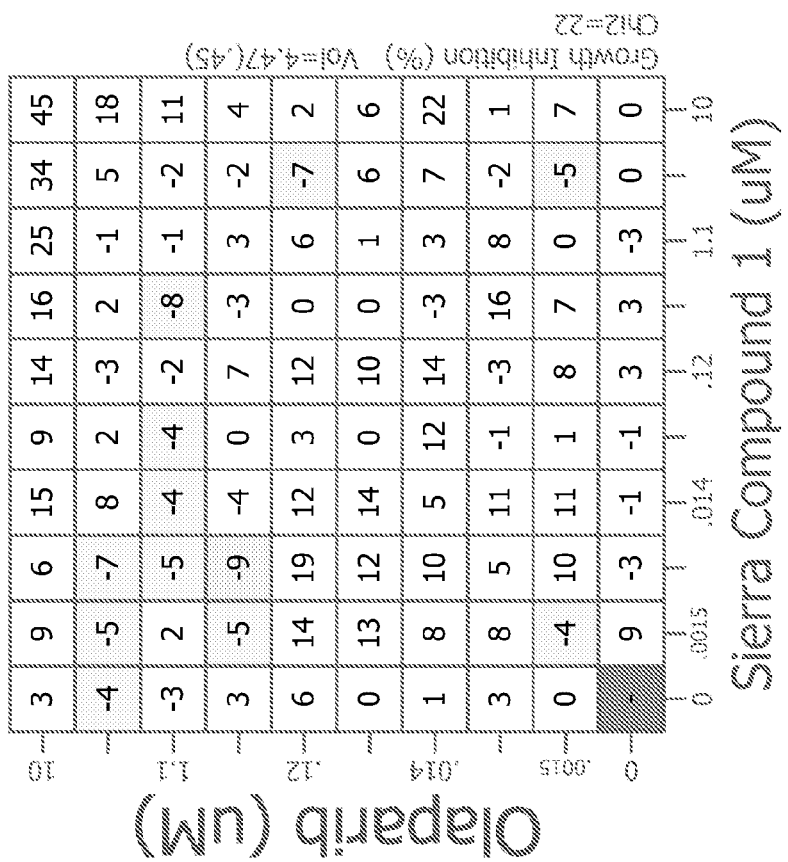
Figure 18:
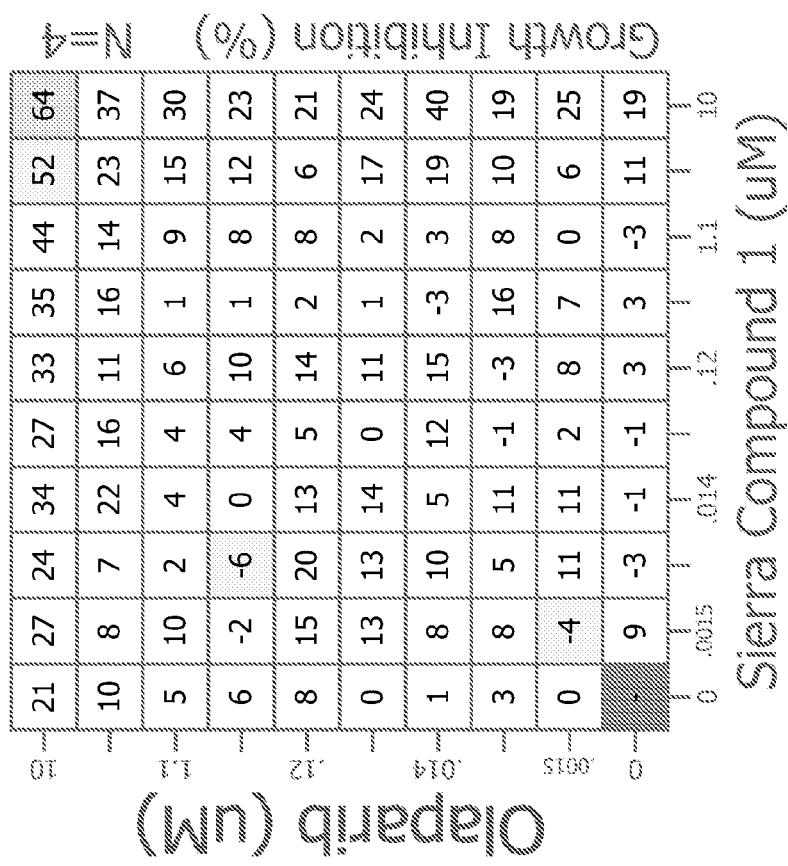
Figure 18:
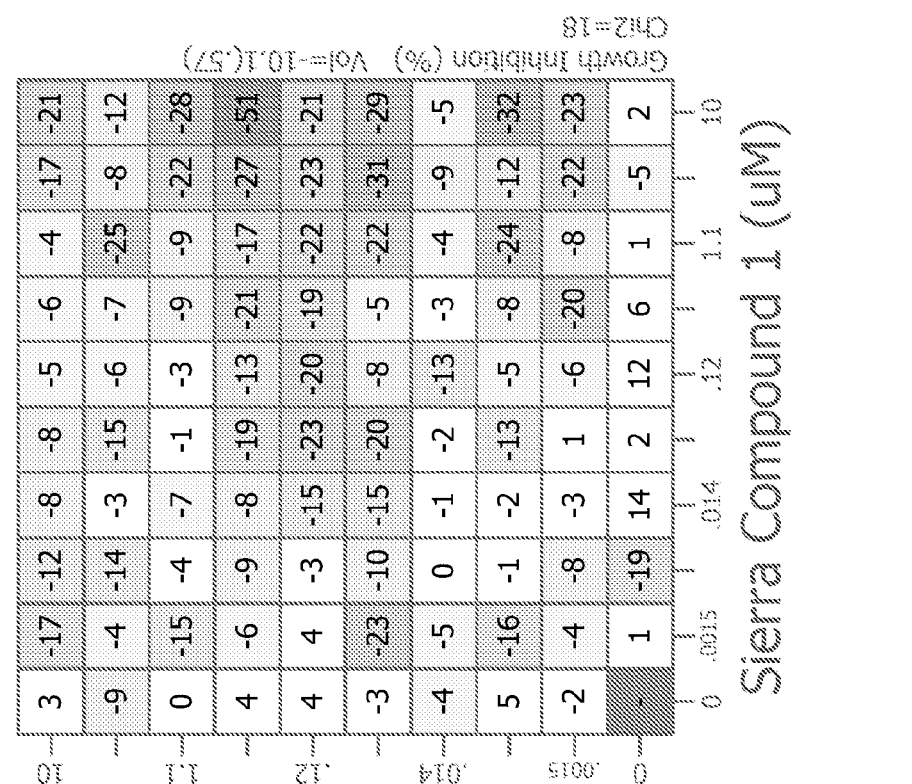
Figure 18:
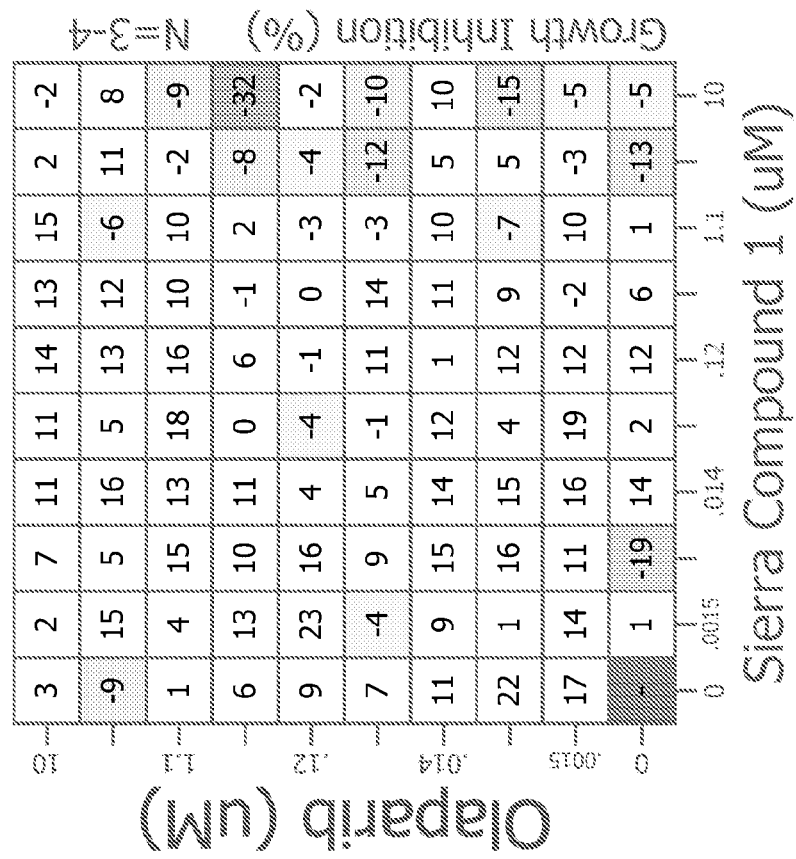
Figure 18:
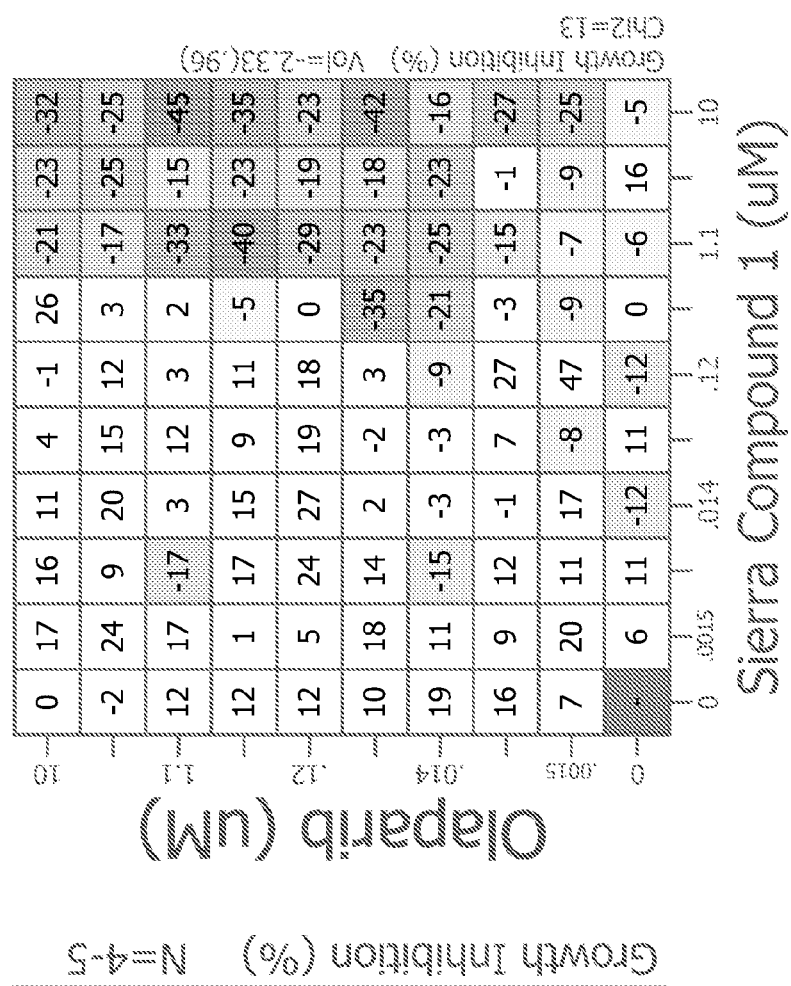
Figure 18:
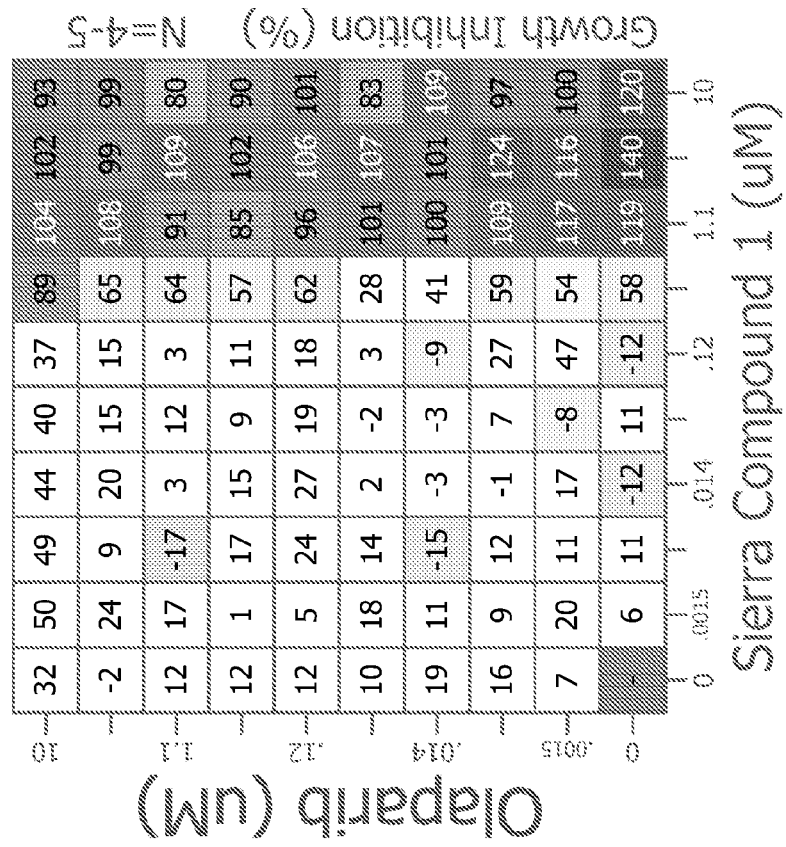
Figure 19:
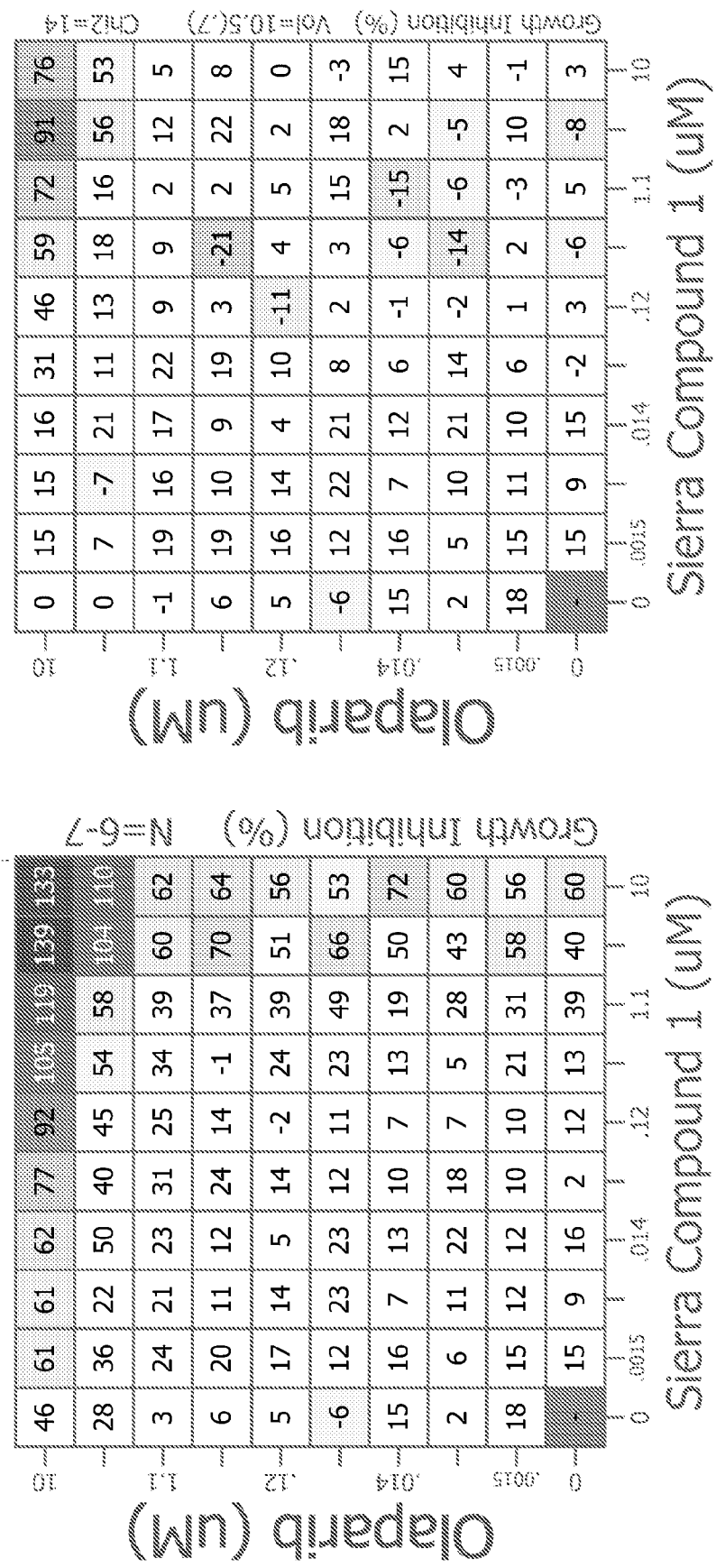
FIG. 19 shows combination activity of Sierra Compound 1 (SRA737) and Olaparib in OVCAR-3 cells and OVCAR-5 cells.
Figure 19:
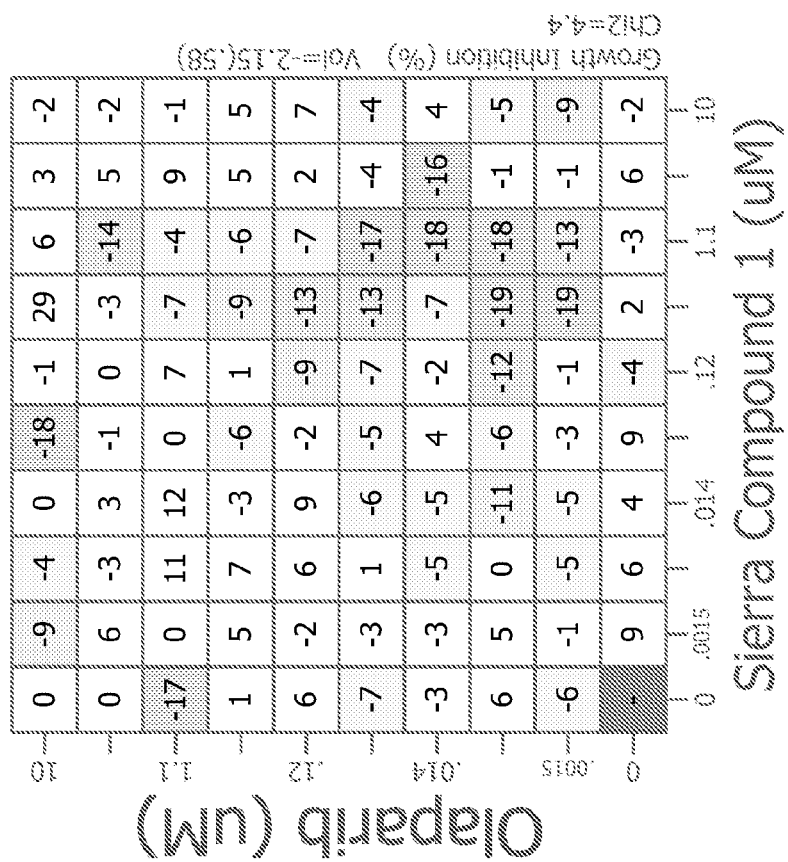
Figure 19:
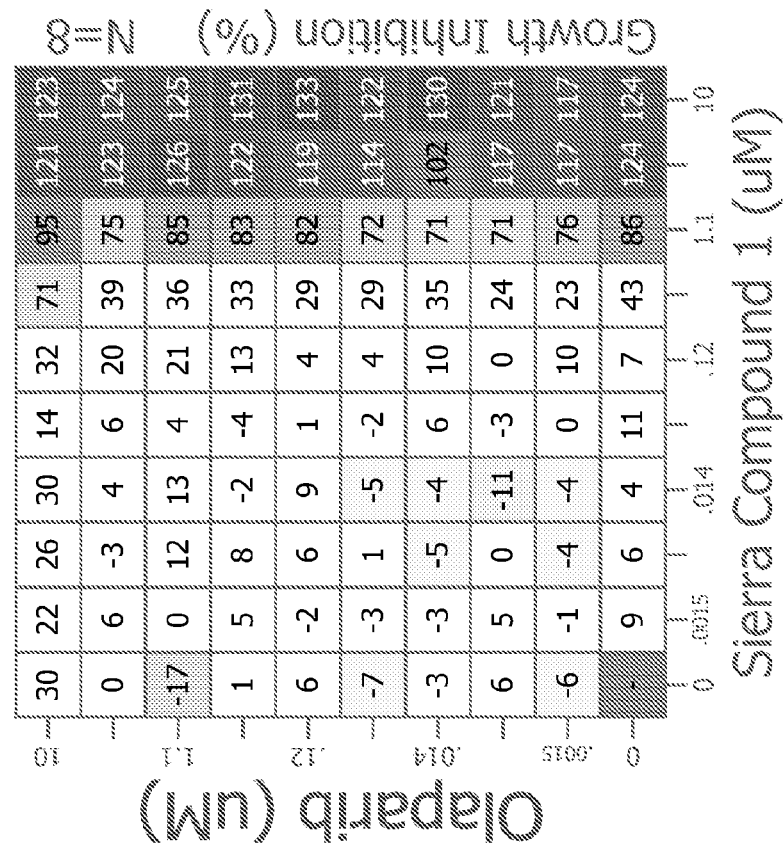
Figure 20:
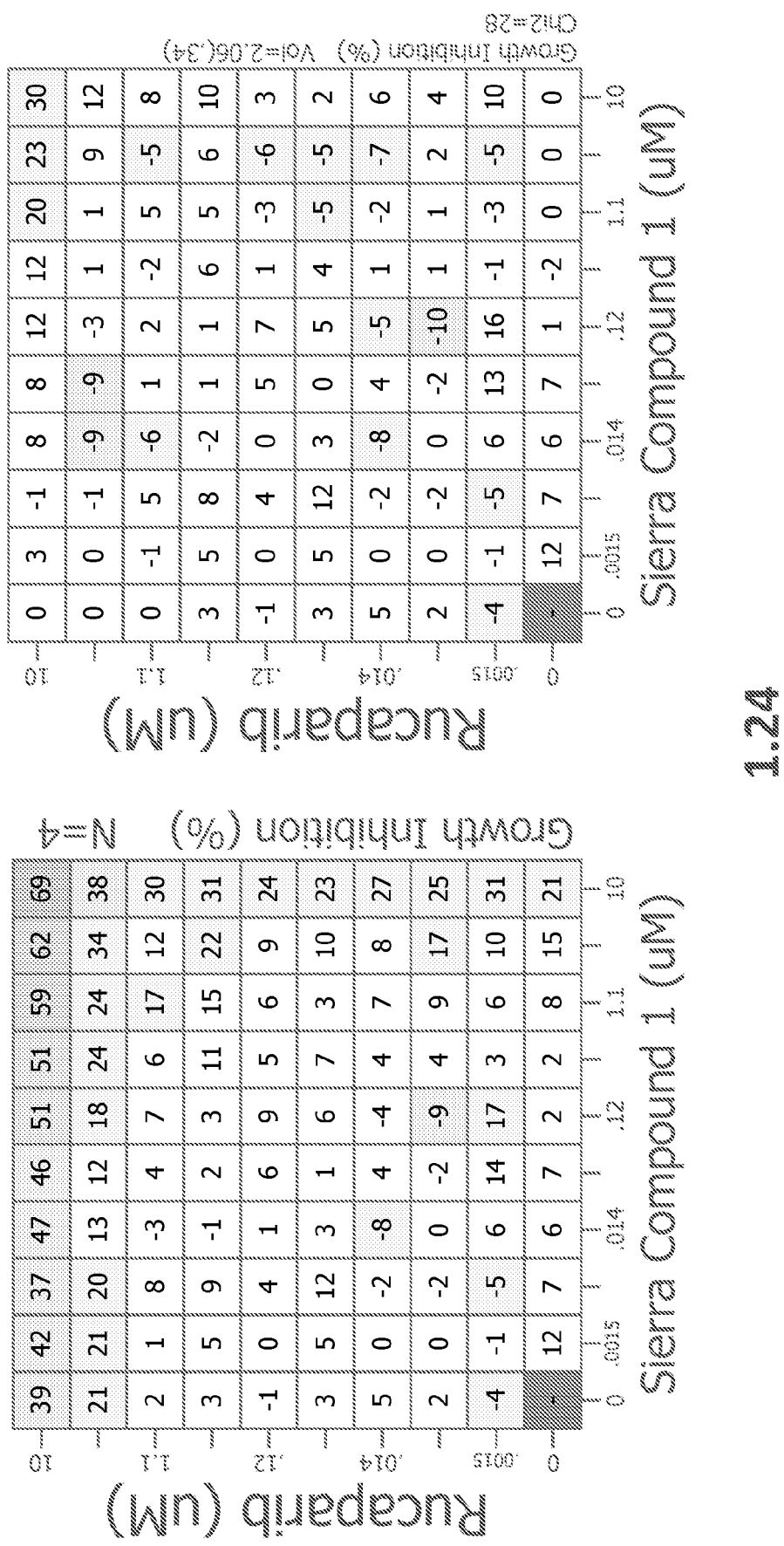
FIG. 20 shows combination activity of Sierra Compound 1 (SRA737) and Rucaparib in PC-3 cells, HT-29 cells, DU-145 cells and CAL-27 cells.
Figure 20:
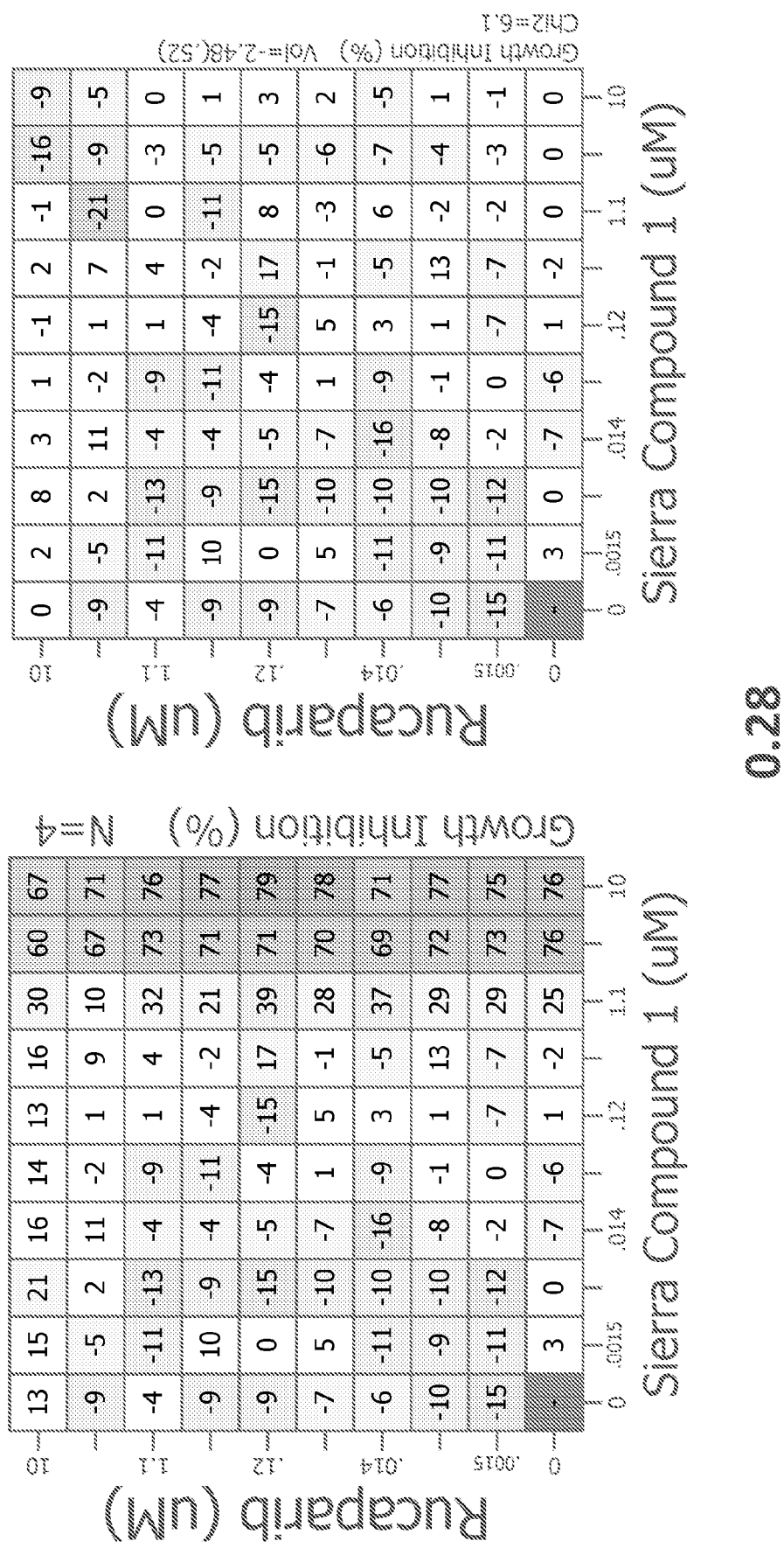
Figure 20:
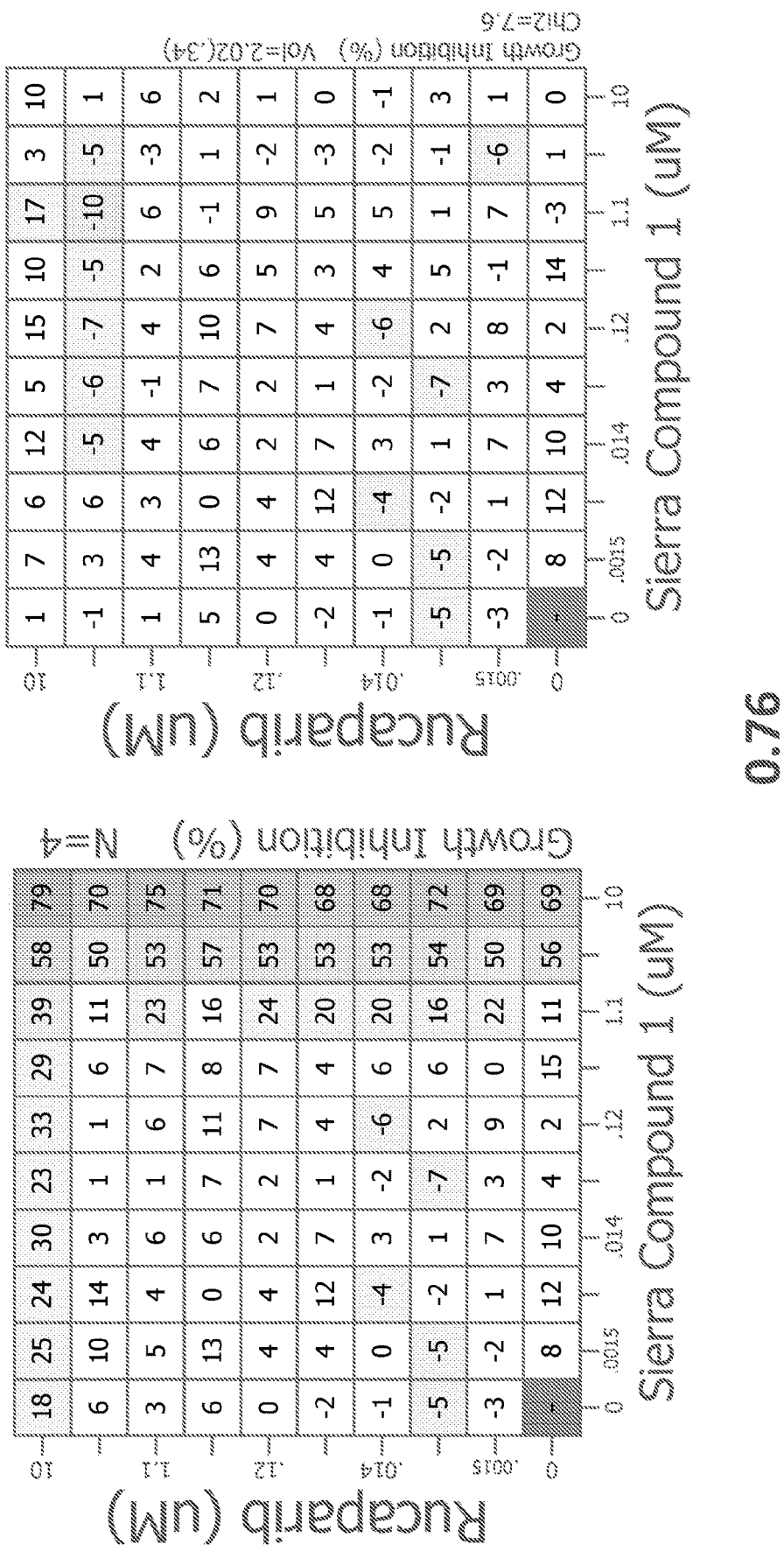
Figure 20:
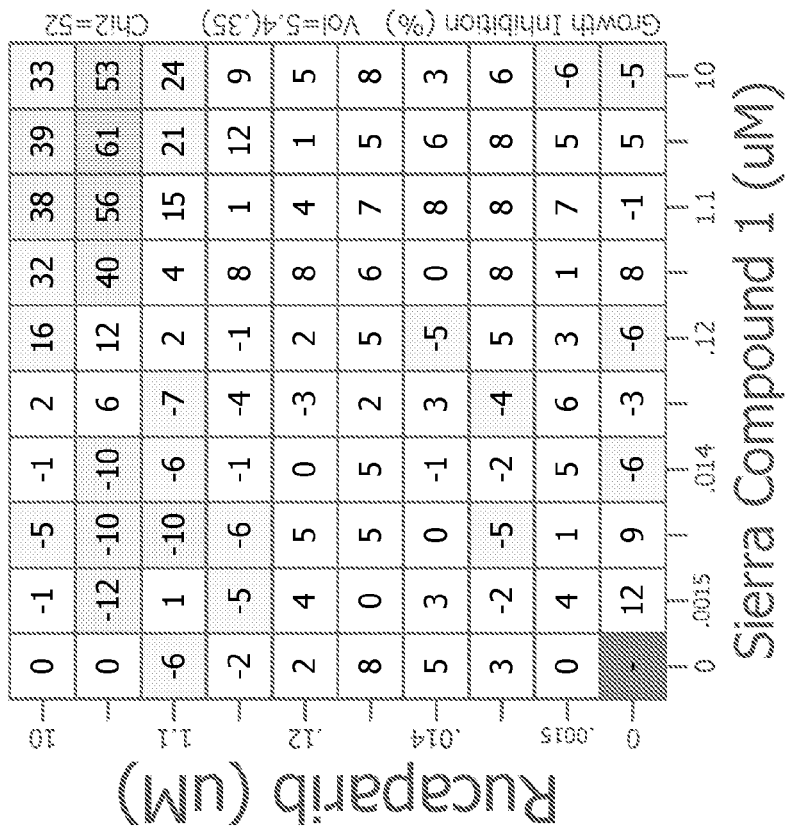
Figure 20:
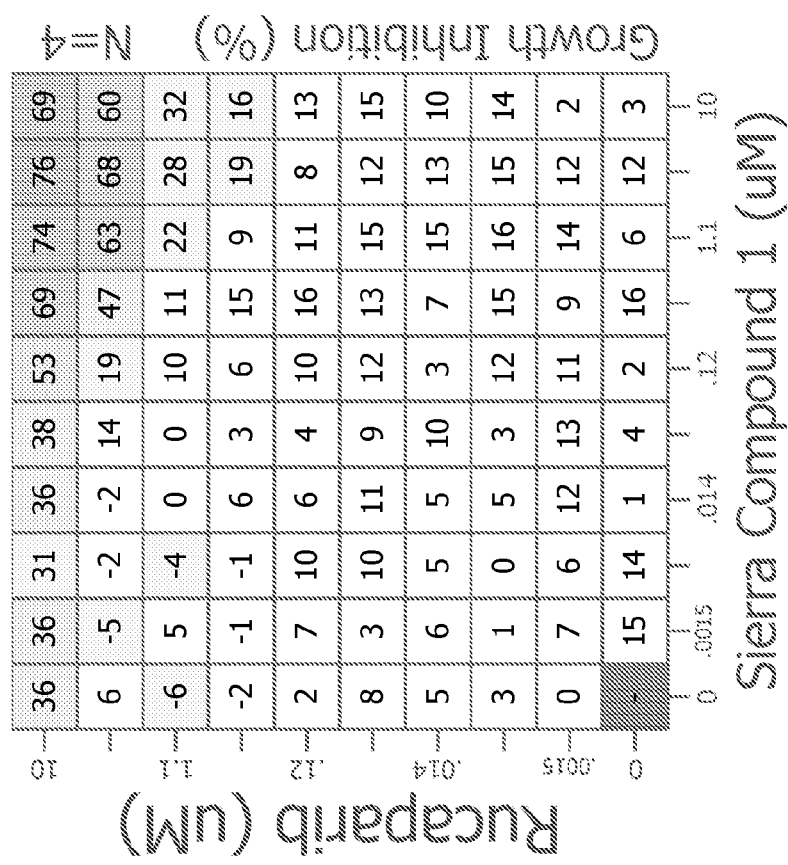
Figure 21:
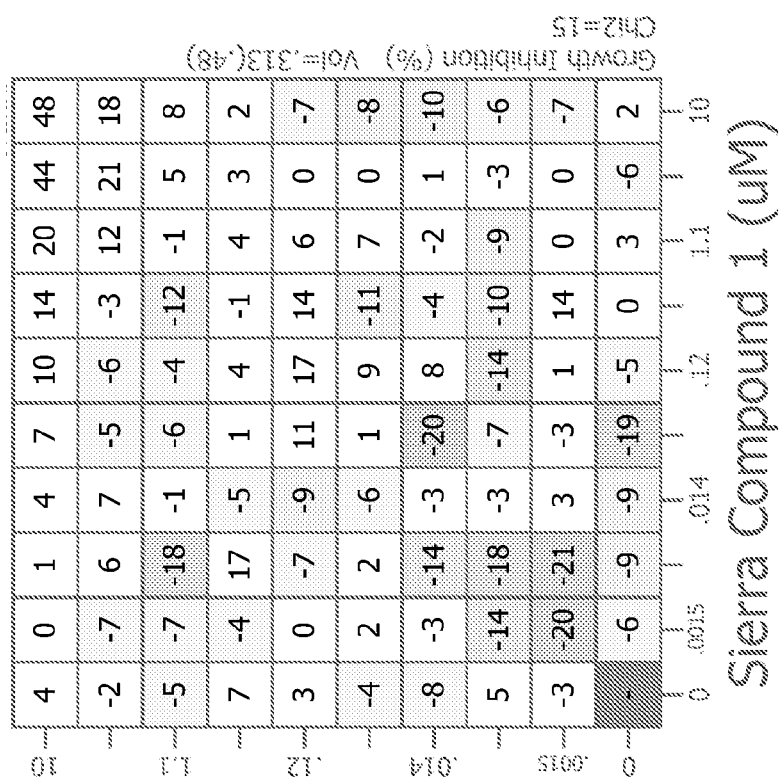
FIG. 21 shows combination activity of Sierra Compound 1 (SRA737) and Rucaparib in A673 cells, MDA-MB-231 cells, BT474 cells, and SK-BR-3 cells.
Figure 21:
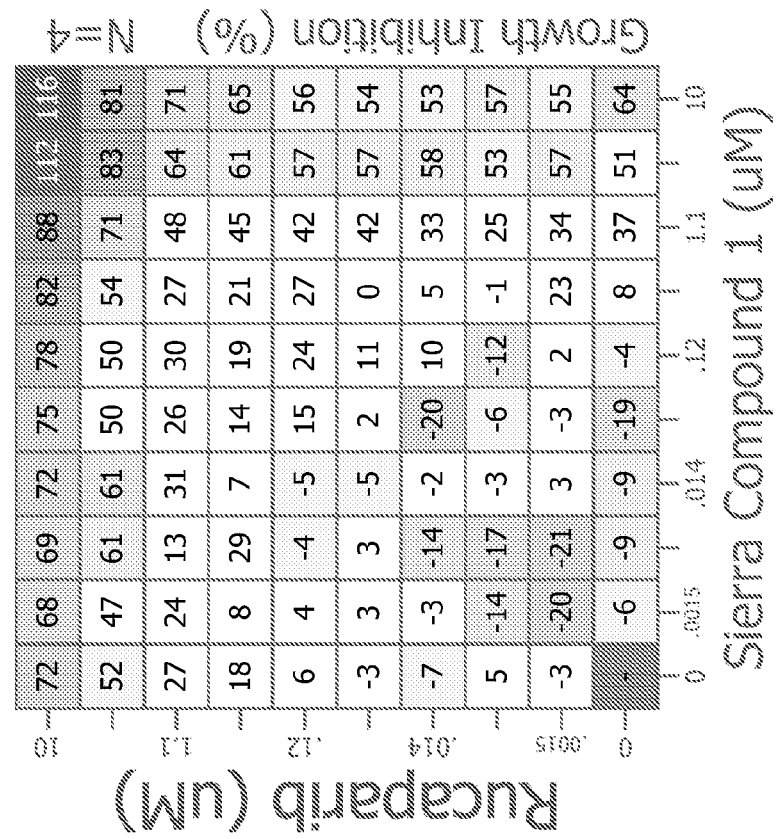
Figure 21:
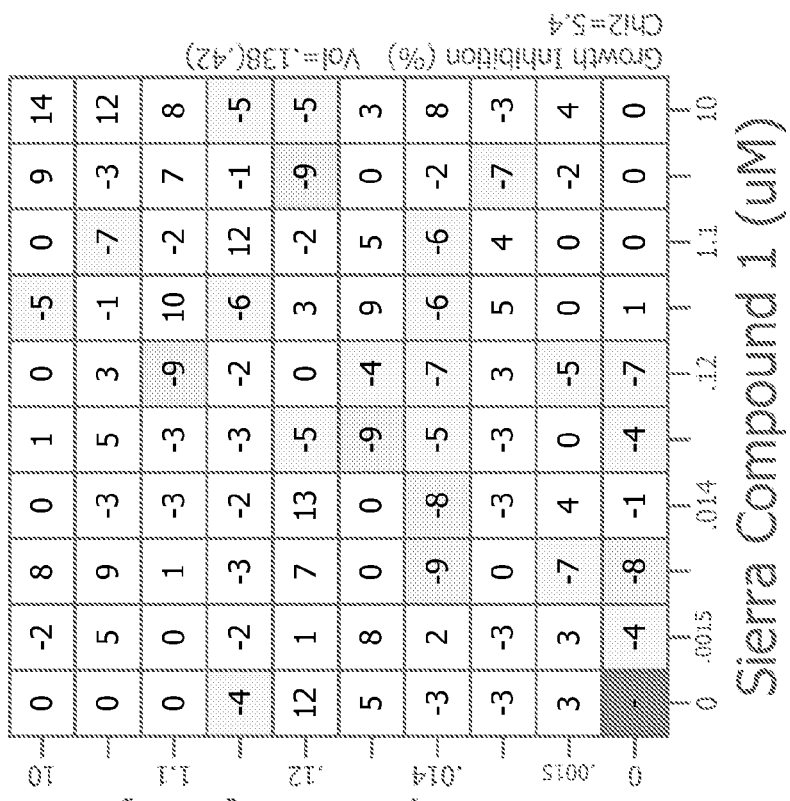
Figure 21:
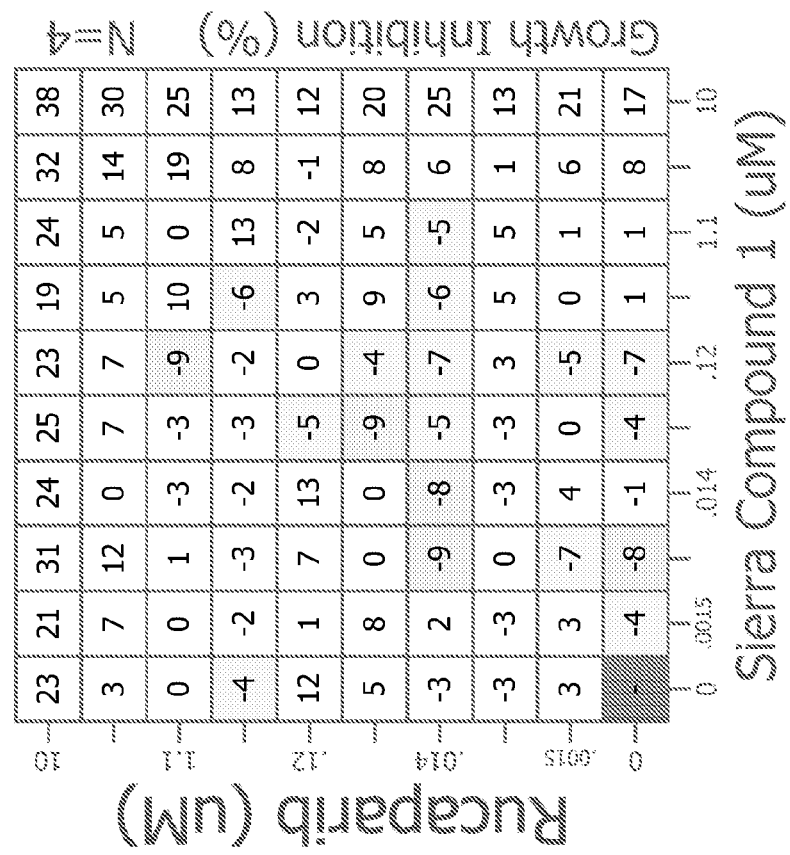
Figure 21:
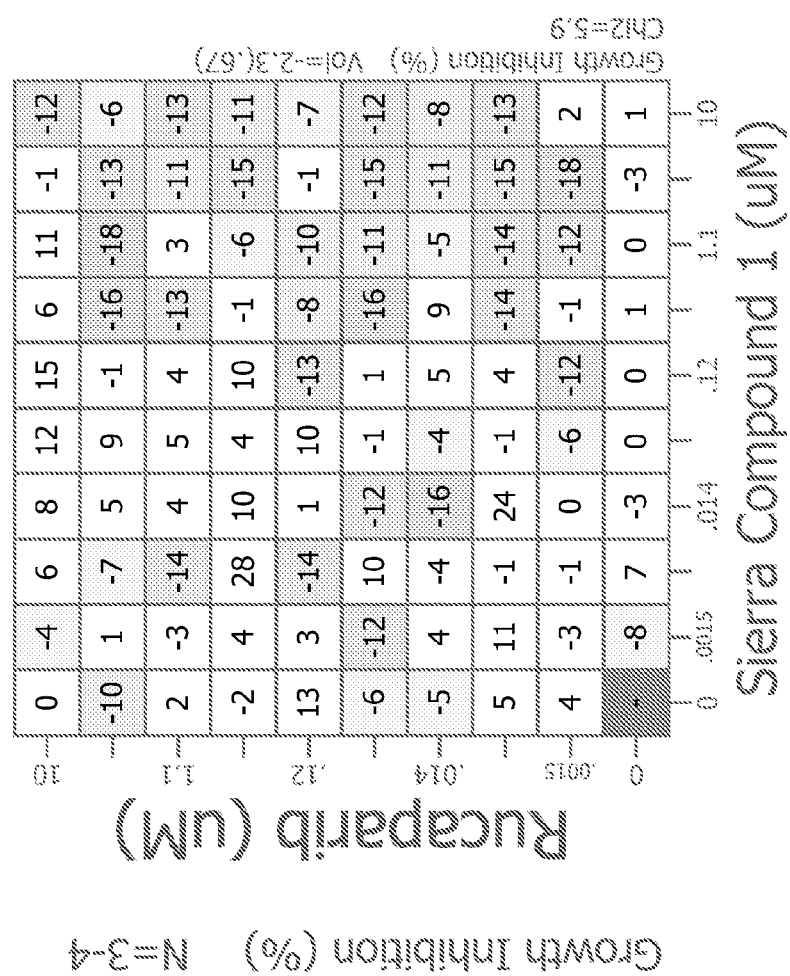
Figure 21:
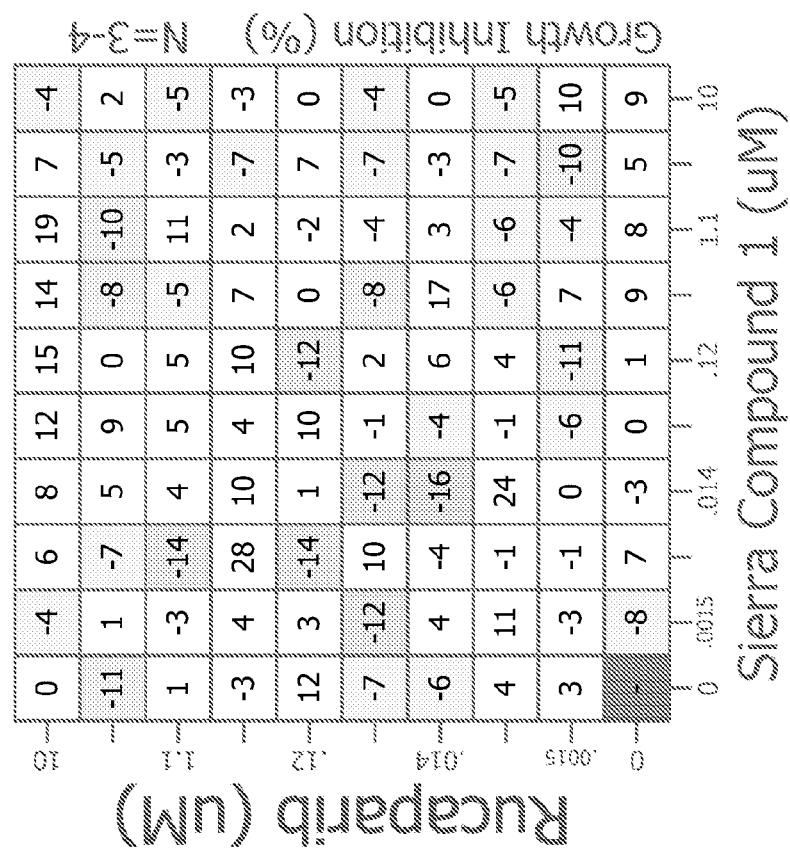
Figure 21:
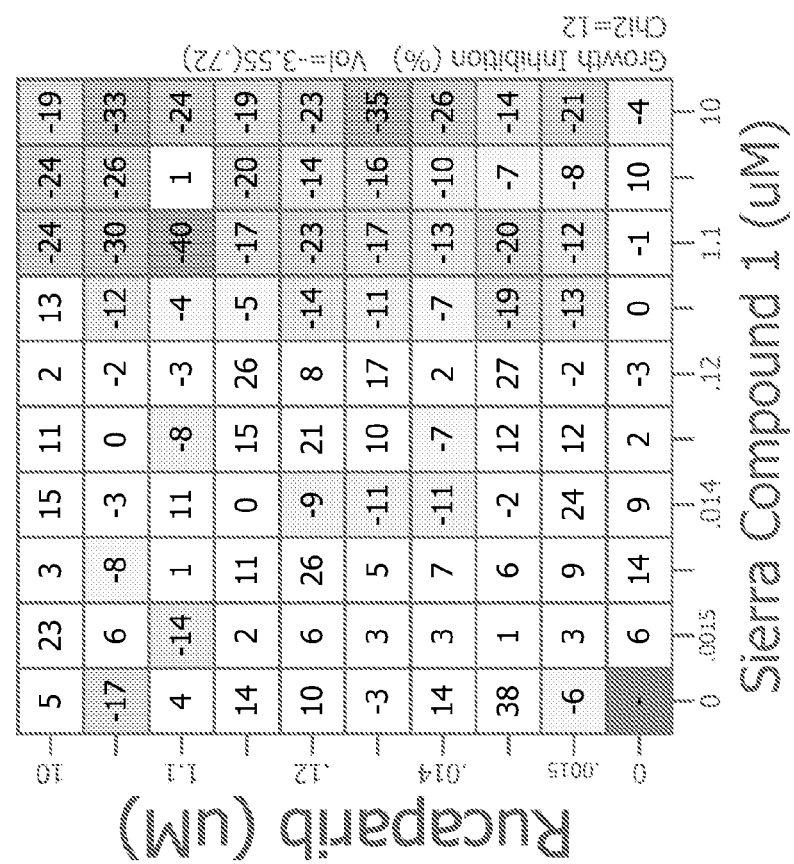
Figure 21:
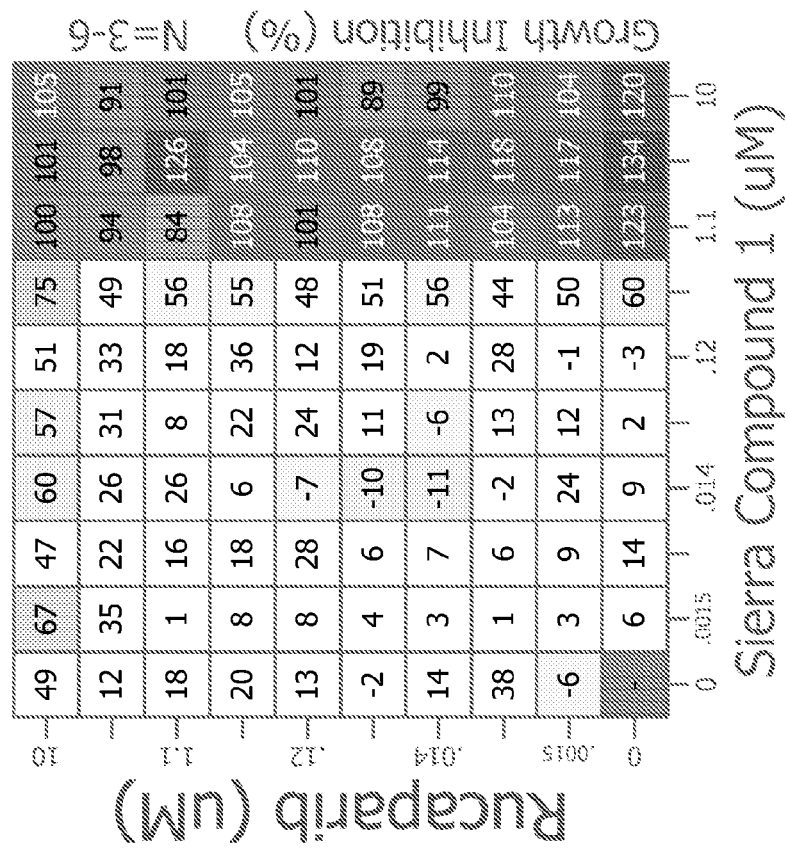
Figure 22:
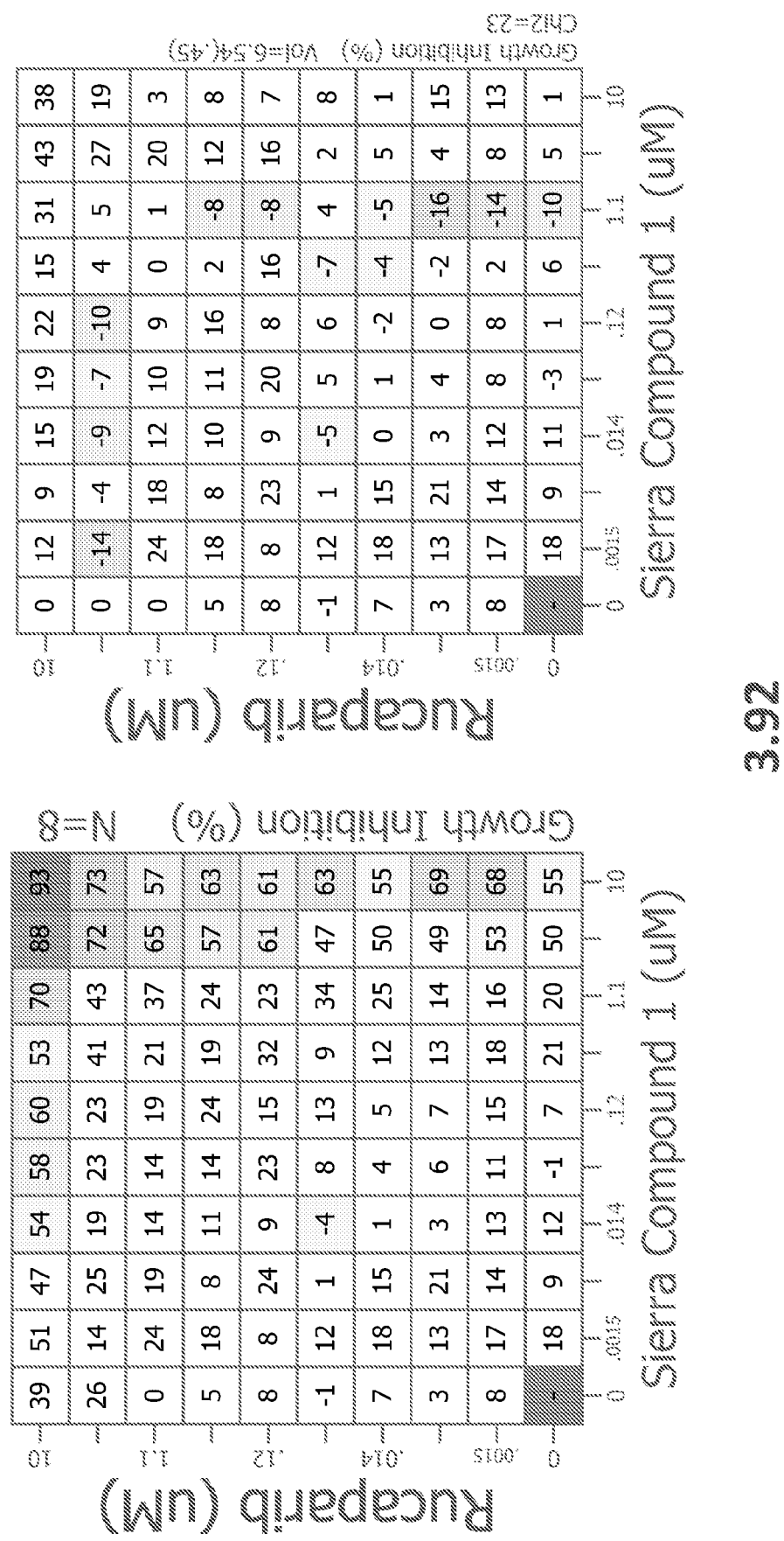
FIG. 22 shows combination activity of Sierra Compound 1 (SRA737) and Rucaparib in OVCAR-3 cells and OVCAR-5 cells.
Figure 22:
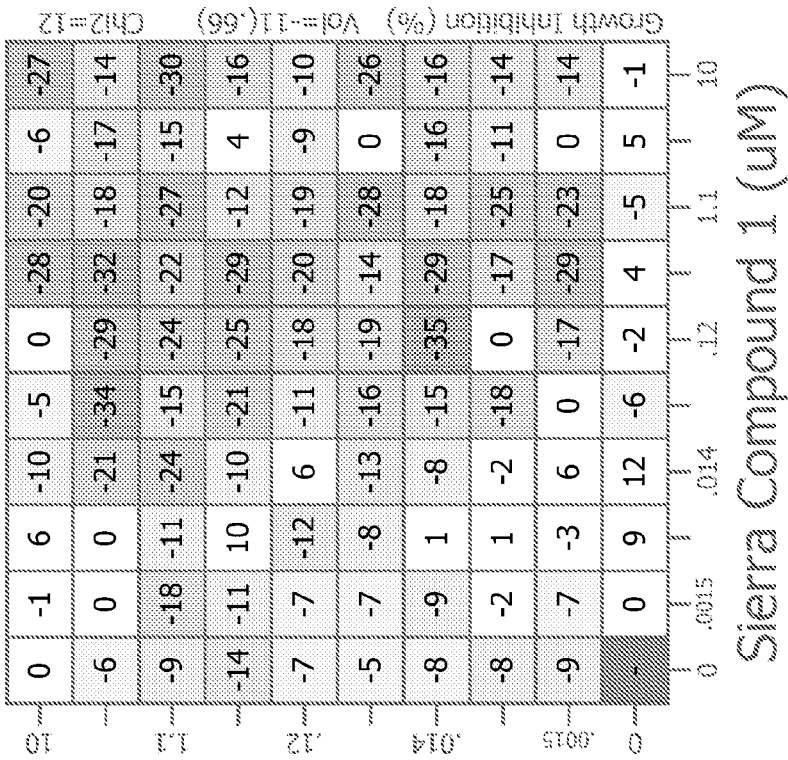
Figure 22:
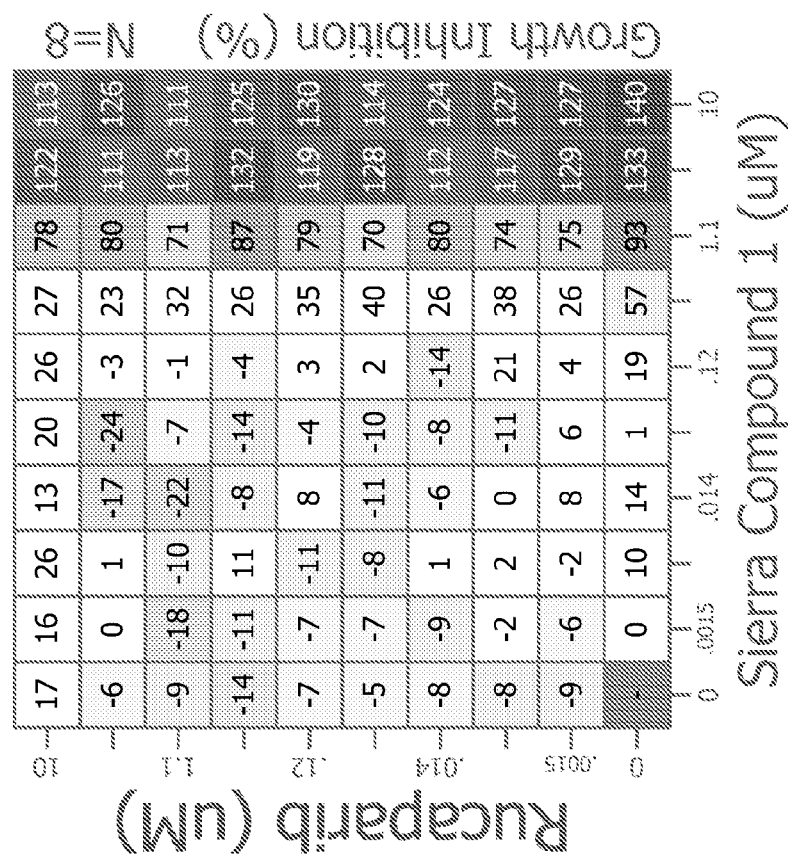

The four PARP inhibitors tested, BMN 673 (Talazoparib), Niraparib, Olaparib and Rucaparib also demonstrated activity in most of the cancer cell lines tested. In particular, cell lines A673 and SK-BR-3 were consistently sensitive to PARP inhibition (FIGS. 8 and 9).

Example 2: Combination Assessment

Cell lines were screened using a 10×10 combination matrix, with a co-treatment 72h treatment time and using ATPlite™ as an endpoint. Synergy scores and Loewe Volumes were calculated as described above (FIGS. 10-23).

Figure 23:
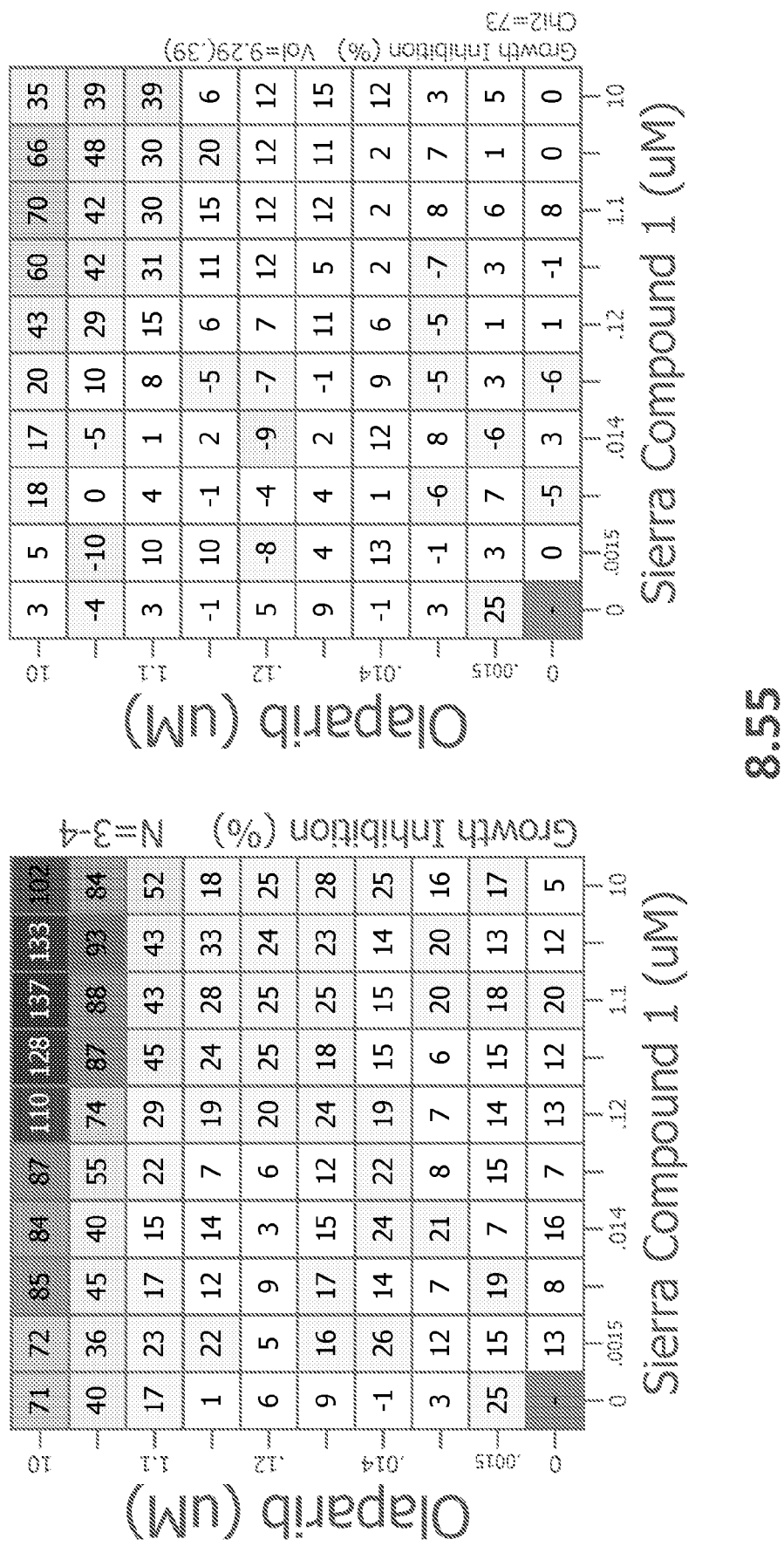
FIG. 23 shows a comparison of combination activity results of "Sierra Compound 1"/"ProNAi Compound 1" (SRA737) and Olaparib with results from a prior study in CAL-27 and OVCAR-3 cell lines.
Figure 23:
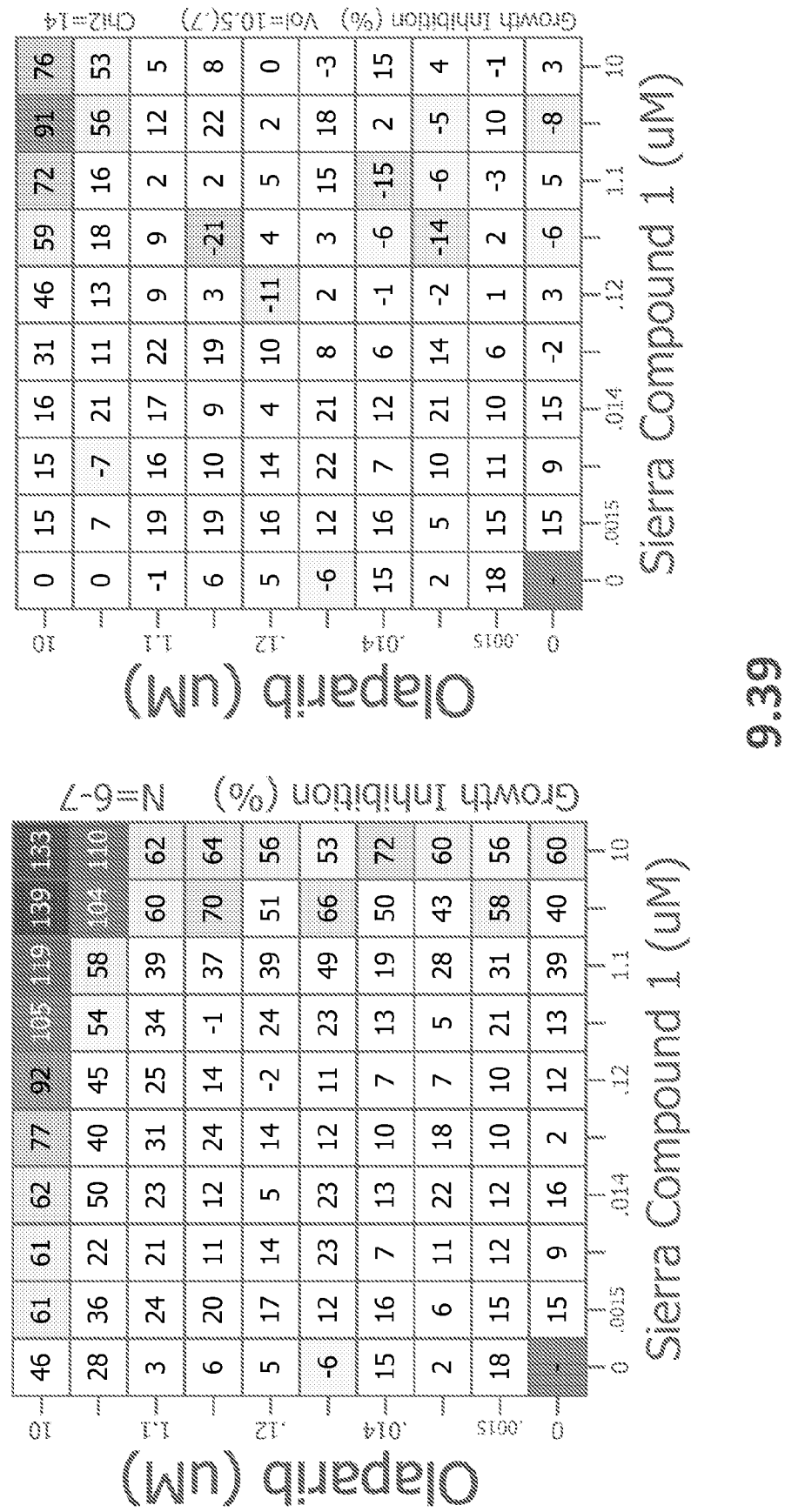
Figure 23:
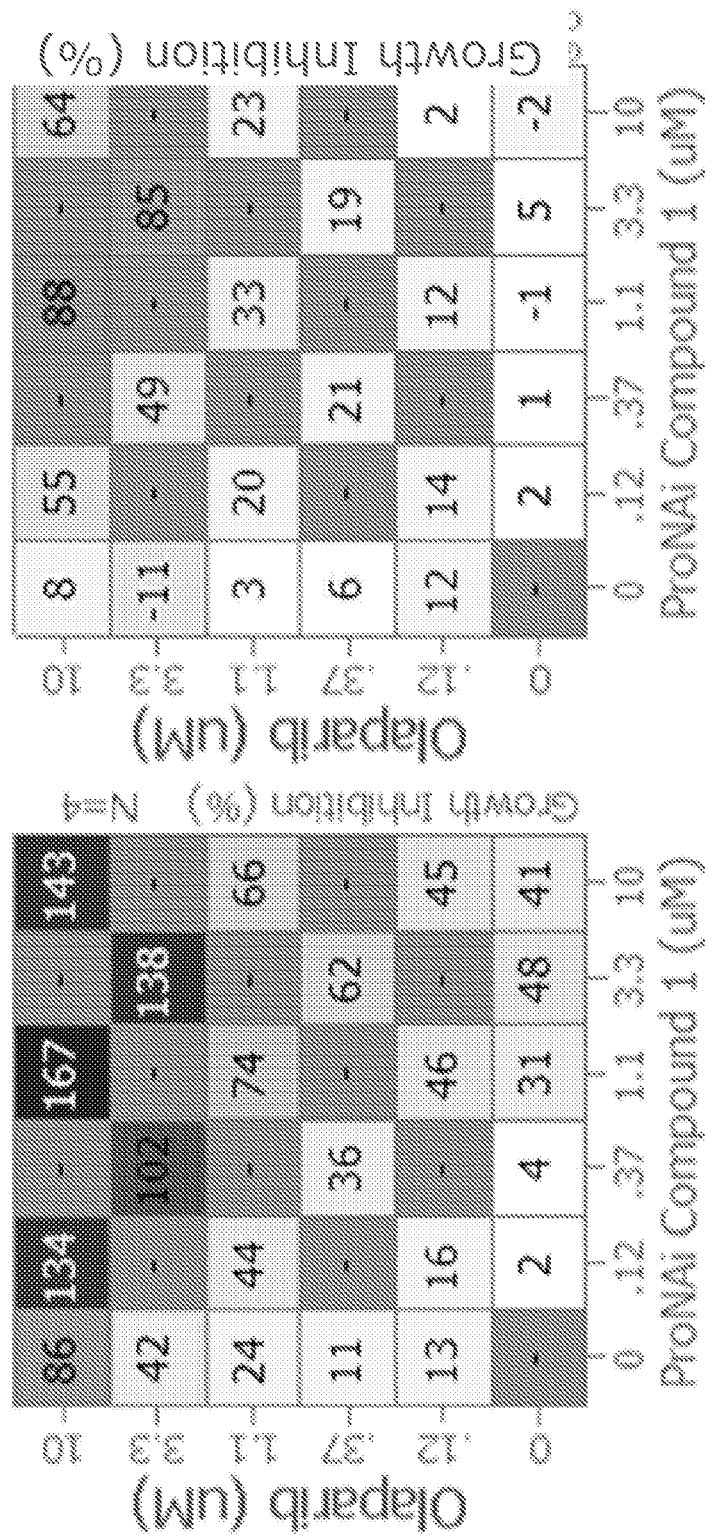
Figure 23:
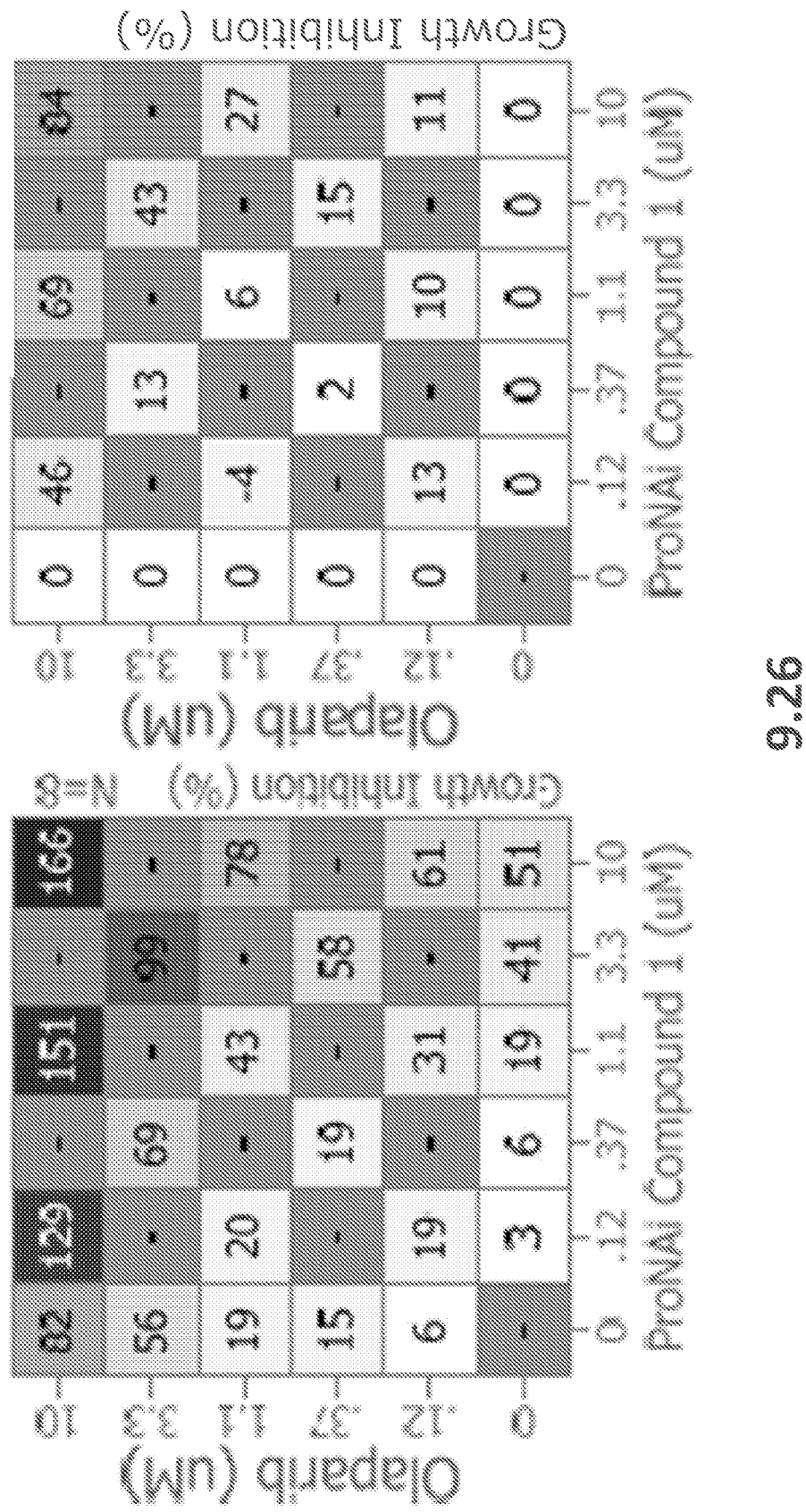

SRA737 exhibited synergistic interactions with PARP inhibitors. The strongest synergies and greatest breadth of activity was observed with BMN 673 (Talazoparib) in 8 out of 10 cell lines, which included cell lines that were insensitive to single agent PARP inhibition (FIGS. 10-13). Although the lower synergy scores were lower relative to BMN 763, synergies were also observed in combination with Niraparib, Olaparib and Rucaparib. Synergistic interaction results with Olaparib in the CAL-27 and OVCAR-3 cell lines were consistent with prior study (FIG. 23).

Example 3: Combination Assessment of Chk1 Inhibitors

Synergistic activity of structurally distinct Chk1 inhibitors with PARP inhibitors is confirmed by assessing the single agent activity of individual Chk1 inhibitors in 10 cancer cell lines (A673, B-474, CAL-27, DU-145, MDA-MB-231, OVCAR-3, OVCAR-5, PC-3 and SK-BR-3) as described above, followed by assessing combination activity of each Chk1 inhibitor with each of four PARP inhibitors: BMN 673 (Talazoparib), Niraparib, Olaparib and Rucaparib. Synergy score analysis and Loewe volume score analysis is performed as described above. Structurally distinct Chk1 inhibitors include, but are not limited to: SRA737, Prexasertib (LY2606368), PF-477736, AZD7762, Rabusertib (LY2603618), MK-8776 (SCH 900776), CHIR-124, SAR-020106 or CCT245737.

Example 4: Combination Methods of Treating Tumor Growth in Humans

A human subject with a tumor is treated with a combination of a Chk1 inhibitor and a PARP inhibitor resulting in a reduction of tumor growth.

A subject in need of treatment is selected or identified. The identification of the subject can occur in a clinical setting. The subject has a tumor resulting from a cancer, e.g., the subject has bladder cancer, breast cancer, colorectal cancer, esophageal cancer, gastric cancer, head and neck cancer, hepatocellular cancer, leukemia, lung cancer, lymphoma, mesothelioma, melanoma, myeloma, ovarian cancer, prostate cancer, pancreatic cancer, renal cell cancer, small cell lung cancer, or squamous cell carcinoma of the head and neck.

At time zero, a suitable first dose of each of a Chk1 inhibitor and a PARP inhibitor is administered to the subject, either separately or in combination. The PARP inhibitor is, e.g., Olaparib, Rucaparib, Veliparib, Niraparib, Iniparib, Talazoparib, Veliparib, Fluzoparib, BGB-290, CEP-9722, BSI-201, EZ449, PF-01367338, AZD2281, INO-1001, MK-4827, SC10914 or 3-aminobenzamine. The Chk1 inhibitor is, e.g., SRA737, Prexasertib (LY2606368), PF-477736, AZD7762, Rabusertib (LY2603618), MK-8776 (SCH 900776), CHIR-124, SAR-020106 or CCT245737. The Chk1 inhibitor and PARP inhibitor are formulated as described herein.

After a period of time following the first dose, the subject's condition is evaluated, e.g., by measuring tumor growth. This measurement can be accompanied by a measurement of expression of a marker gene in a cell, of inhibiting a Chk1 activity in a cell, and of inhibiting PARP activity in a cell. Other relevant clinical endpoints are also measured as described herein.

The number and strength of doses are adjusted according to the subject's needs.

After treatment, the subject's tumor growth rate is lowered relative to the rate existing prior to the treatment, or relative to the rate measured in a similarly afflicted but untreated subject.

While the invention has been particularly shown and described with reference to a preferred embodiment and various alternate embodiments, it are understood by persons skilled in the relevant art that various changes in form and details can be made therein without departing from the spirit and scope of the invention.

All references, issued patents and patent applications cited within the body of the instant specification are hereby incorporated by reference in their entirety, for all purposes

REFERENCES CITED

T. E. Creighton, *Proteins: Structures and Molecular Properties* (W.H. Freeman and Company, 1993)
A. L. Lehninger, *Biochemistry* (Worth Publishers, Inc., current addition)
Sambrook, et al., *Molecular Cloning: A Laboratory Manual* (2nd Edition, 1989)
*Methods In Enzymology* (S. Colowick and N. Kaplan eds., Academic Press, Inc.)
*Remington's Pharmaceutical Sciences,* 18th Edition (Easton, Pa.: Mack Publishing Company, 1990)
Carey and Sundberg *Advanced Organic Chemistry* $3^{rd}$ Ed. (Plenum Press) Vols A and B (1992)
U.S. Pat. No. 5,145,684
U.S. Pat. No. 4,107,288
Monga S P, Wadleigh R, Sharma A, et al. Intratumoral therapy of cisplatin/epinephrine injectable gel for palliation in patients with obstructive esophageal cancer. Am. J. Clin. Oncol. 2000; 23(4):386-392
Mary M. Tomayko C., Patrick Reynolds, 1989. Determination of subcutaneous tumor size in athymic (nude) mice. Cancer Chemotherapy and Pharmacology, Volume 24, Issue 3, pp 148-154
E Richtig, G Langmann, K Müllner, G Richtig and J Smolle, 2004. Calculated tumour volume as a prognostic parameter for survival in choroidal melanomas. Eye (2004) 18, 619-623
Jensen et al. BMC Medical Imaging 2008. 8:16
Tomayko et al. Cancer Chemotherapy and Pharmacology September 1989, Volume 24, Issue 3, pp 148-154
Faustino-Rocha et al. Lab Anim (NY). 2013 June; 42(6): 217-24

The invention claimed is:

1. A method of inhibiting a tumor growth in a subject in need thereof, comprising administering to the subject a first effective amount of SRA737 comprising a structure of

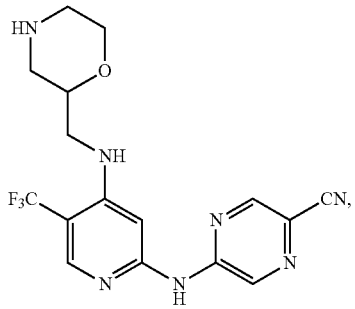

and a second effective amount of a poly ADP ribose polymerase (PARP) inhibitor (PARPi), wherein the subject has a cancer that is resistant to PARPi therapy, wherein the cancer is breast cancer, ovarian cancer, pancreatic cancer, or prostate cancer, and wherein the PARPi is talazoparib, niraparib, or rucaparib.

2. The method of claim 1, wherein the SRA737 and the PARP inhibitor (PARPi) are administered separately.

3. The method of claim 2, wherein the SRA737 is administered at least twenty-four (24) hours after the administration of the PARPi.

4. The method of claim 1, wherein after the SRA737 and the PARPi are administered, subsequently both the SRA737 and the PARPi are administered intermittently for at least twenty-four (24) hours.

5. The method of claim 1, wherein the SRA737 and the PARPi are administered on a non-overlapping every other day schedule, or wherein the SRA737 and the PARPi are administered on a non-overlapping every 3 day alternating schedule, or wherein the SRA737 and the PARPi are administered on a non-overlapping every 7 day alternating schedule.

6. The method of claim 1, wherein the PARPi is niraparib.

7. The method of claim 1, wherein the subject has a cancer that has a mutation in at least one gene involved in the DNA Damage Response (DDR).

8. The method of claim 1, wherein the subject has a cancer that has a mutation in at least one gene selected from the group consisting of: BRIP1, HDAC2, ATM, BLM, BRCA1, BRCA2, CHEK2, FANCA, FANCC, FANCD2, FANCE, FANCF, FANCG, FANCI, FANCL, FANCM, MLH1, MSH2, MSH6, PALB2, POLD1, POLE, PMS2, POLE, RAD50, RAD51, RAD51B, RAD51C, RAD51D, RAD52, RAD54L, RPA1, SETD2 SMARCA4, TP53BP1, XRCC2, XRCC3, KMT2D and ARID1A.

9. The method of claim 1, wherein the subject has a cancer with a mutation or altered expression in REV7, SCHLFN-11, or combinations thereof.

10. The method of claim 1, wherein the subject has a cancer that does not have a mutation or altered expression in BRCA, other homologous recombination genes, or combinations thereof.

11. The method of claim 1, wherein the subject has a cancer that is proficient in the homologous recombination pathway.

12. The method of claim 1, wherein the first effective amount is 0.001 mg/kg to 15 mg/kg and the second effective amount is 0.001 mg/kg to 15 mg/kg, or wherein the first effective amount is 0.1 mg/kg to 1.5 mg/kg and the second effective amount is 0.1 mg/kg to 1.5 mg/kg.

13. The method of claim 1, wherein tumor growth is reduced in the subject.

14. The method of claim 1, wherein administration results in tumor growth of no more than 5% of the original tumor volume as measured after administration.

15. The method of claim 1, wherein the subject is human.

16. A method of reducing cellular proliferation of a cell, comprising contacting the cell with a first effective amount of SRA737 comprising a structure of

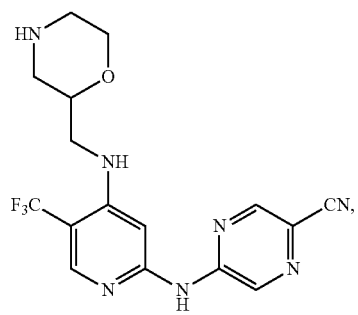 [SMILES: N#Cc1cnc(Nc2cc(NCC3CNCCO3)c(C(F)(F)F)cn2)cn1]

and a second effective amount of a poly ADP ribose polymerase inhibitor (PARPi), wherein the cell is a cancer tumor cell that is resistant to PARPi therapy, wherein the cancer cell is a breast cancer, ovarian cancer, pancreatic cancer, or prostate cancer cell, and wherein the PARPi is talazoparib, niraparib, or rucaparib.

17. The method of claim 16, wherein the method is performed in vitro.

18. The method of claim 16, wherein the SRA737 and the PARPi are administered simultaneously, or wherein the SRA737 and the PARPi are administered sequentially.

19. The method of claim 16, wherein after the SRA737 and the PARPi are administered, subsequently both SRA737 and the PARPi are administered intermittently for at least twenty-four (24) hours.

20. The method of claim 16, wherein the SRA737 and the PARPi are administered on a non-overlapping every other day schedule, or wherein the SRA737 and the PARPi are administered on a non-overlapping every 3 day alternating schedule, or wherein the SRA737 and the PARPi are administered on a non-overlapping every 7 day alternating schedule.

21. The method of claim 16, wherein the PARPi is niraparib.

* * * * *